(12) United States Patent
Yamaha et al.

(10) Patent No.: US 8,921,643 B2
(45) Date of Patent: Dec. 30, 2014

(54) METHOD FOR ACQUIRING GENETICALLY IDENTICAL GAMETE FROM LETHAL FISH HAPLOID-DERIVED GERM CELL VIA GERM LINE CHIMERA

(75) Inventors: Etsuro Yamaha, Sapporo (JP); Katsutoshi Arai, Sapporo (JP); Takafumi Fujimoto, Sapporo (JP); Taiju Saito, Sapporo (JP)

(73) Assignee: National University Corporation Hokkaido University, Sapporo-shi (JP)

( * ) Notice: Subject to any disclaimer, the term of this patent is extended or adjusted under 35 U.S.C. 154(b) by 0 days.

(21) Appl. No.: 13/577,829

(22) PCT Filed: Feb. 9, 2011

(86) PCT No.: PCT/JP2011/052772
§ 371 (c)(1),
(2), (4) Date: Aug. 8, 2012

(87) PCT Pub. No.: WO2011/099528
PCT Pub. Date: Aug. 18, 2011

(65) Prior Publication Data
US 2012/0304322 A1 Nov. 29, 2012

(30) Foreign Application Priority Data
Feb. 9, 2010 (JP) ................................ 2010-026904

(51) Int. Cl.
C12N 15/00 (2006.01)
A01K 67/027 (2006.01)
C12N 5/00 (2006.01)
C12N 5/02 (2006.01)
C12N 5/10 (2006.01)
C12N 15/09 (2006.01)

(52) U.S. Cl.
CPC ............... *C12N 5/10* (2013.01); *A01K 67/0271* (2013.01); *A01K 67/027* (2013.01); *C12N 15/09* (2013.01)
USPC ............................... 800/21; 800/20; 435/325

(58) Field of Classification Search
CPC .................................................. A01K 67/027
See application file for complete search history.

(56) References Cited

FOREIGN PATENT DOCUMENTS

WO WO 2006/040926 A1 4/2006

OTHER PUBLICATIONS

Saito et al, Int. J Dev Biol, 2010, 54:1481-1486.*
Saito, Biology of Reproduction 2008, 78:159-166.*
Schulz, General and Comparative Endocrinology, 2010, 165:390-411.*
Arai, "Current Status of Chromosome Manipulation and Contact Point between Naturally Occuring Polyploids and Clones," Mini-Symposium—Current Status and Prospects of Developmental Engineering in Fish, Nippon Suisan Gakkaishi, vol. 72, No. 5, 2006, pp. 952-953, with partial English translation.
Arai, "DNA of Fish," Chromosome Manipulation, Kouseisya Kousikaku, Tokyo, 1997, pp. 32-62 with partial English translation (8 pages).
Itono et al., "Cytological Mechanisms of Gynogenesis and Sperm Incorporation in Unreduced Diploid Eggs of the Clonal Loach, *Misgurnus anguillicaudatus* (Teleostei: Cobitidae)," Journal of Experimental Zoology, vol. 307A, 2007, pp. 35-50.
Itono et al., Premeiotic Endomitosis Produces Diploid Eggs in the Natural Clone Loach, *Misgurnus anguillicaudatus* (Teleostei: Cobitidae), Journal of Experimental Zoology, vol. 305A, 2006, pp. 513-523.
Morishima et al., "A Cryptic Clonal Line of the Loach *Misgurnus anguillicaudatus* (Teleostei: Cobitidae) Evidenced by Induced Gynogenesis, Interspecific Hybridization, Microsatellite Genotyping and Multilocus DNA Fingerprinting," Zoological Science, vol. 19, 2002, pp. 565-575.
Morishima et al., "Clonal Diploid Sperm of the Diploid-Triploid Mosaic Loach, *Misgurnus anguillicaudatus* (Teleostei:Cobitidae)," Journal of Experimental Zoology, vol. 301A, 2004, pp. 502-511.
Morishima et al., "Meiotic hybridogenesis in triploid Misgurnus loach derived from a clonal lineage," Heredity, vol. 100, 2008, pp. 581-586.
Sakao et al., "Artificially induced tetraploid masu salmon have the ability to form primordial germ cells," Fish Science, vol. 75, 2009, pp. 993-1000.
Streisinger et al., "Production of clones of homozygous diploid zebra fish (*Brachydanio rerio*)," Nature, vol. 291, May 28, 1981, pp. 293-296.
Tanaka et al., "Survival Capacity of Haploid-Diploid Goldfish Chimeras," Journal of Experimental Zoology, vol. 301A, 2004, pp. 491-501.
Yamaki et al., "Live Haploid-diploid Mosaic Charr Salvelinus Leucomaenis," Fisheries Science, vol. 65, No.5, 1999, pp. 736-741.
Yamaki et al., "Progeny of the Diploid-Tetraploid Mosaic Amago Salmon," Nippon Suisan Gakkaishi, vol. 65, No. 6, 1999, pp. 1084-1089, with English abstract.
Yi et al., "Generation of Medaka Fish Haploid Embryonic Stem Cells," Science, vol. 326, Oct. 16, 2009, pp. 430-433.
Yoshikawa et al., "Chromosome Doubling in Early Spermatogonia Produces Diploid Spermatozoa in a Natural Clonal Fish," Biology of Reproduction, vol. 80, 2009, pp. 973-979.
Yoshikawa et al., "Diploid Sperm Produced by Artificially Sex-Reversed Clone Loaches," Journal of Experimental Zoology, vol. 307A, 2007, pp. 75-83.
Extended European Search Report for European Patent Application No. 11742271.7, dated Sep. 3, 2013.
Komen et al, "Androgenesis, gynogenesis and the production of clones in fishes: A review", Aquaculture, 2007, 269:150-173.
Wills et al.,"Reduced reproductive capacity in diploid and triploid hybrid sunfish", Transactions of the American Fisheries Society, 2000, vol. 129, No. 1, pp. 30-40.
Yingxia et al., "The mechanism of tetragametic chimerism in a true hermaphroditism with 46, XX/46, XY", National Journal of Andrology, 2004, 10:107-112.

* cited by examiner

*Primary Examiner* — Valarie Bertoglio
(74) *Attorney, Agent, or Firm* — Birch, Stewart, Kolasch & Birch, LLP

(57) ABSTRACT

Disclosed are a method for acquiring a germ line chimeric fish having fish haploid germ cells, a germ line chimeric fish having haploid germ cells obtained by the aforesaid method, and a genetically identical gamete, said gamete having been derived from a donor haploid germ cell, produced by a germ line chimeric fish obtained by the aforesaid method.

10 Claims, 27 Drawing Sheets

METHOD FOR ACQUIRING GENETICALLY IDENTICAL GAMETE FROM LETHAL FISH HAPLOID-DERIVED GERM CELL VIA GERM LINE CHIMERA

TECHNICAL FIELD

The present invention relates to a method for acquiring a germ line chimeric fish having fish haploid germ cells, a germ line chimeric fish having haploid germ cells obtained by the method, and genetically identical gametes derived from donor haploid germ cells, produced by a germ line chimeric fish obtained by the method.

BACKGROUND ART

The increase in the world population requires it to stably secure food. The improved technologies of breeding and aquaculture are also required in the fishing industry having previously been dependent for most of the amount of production thereof on the fishing of natural resources. Agricultural crops have been subjected to selection breeding for a long time, and further, productivity has been improved using heterosis in F1 hybrids obtained by crossing two pure lines.

One technique for plant breeding includes anther culture (pollen culture). This is a technique which involves culturing the whole anther on a medium to promote the proliferation of haploid pollen (male gametophyte) cells. If a plant remaining a haploid occurs, its genome can be doubled to homogenotize the plant, producing a pure line having fertility. If pure lines can be artificially induced, all of the gametes produced by them are expected to form genetically identical clones. Thus, the different clones can be crossed to produce a heterozygous clonal lineage having heterosis. In other words, the use of the anther culture enables the early fixation of a useful genotype and the shortening of the breeding period. Successful examples of breeding via anther culture include the breeding of Hokkaido rice varieties such as "Nanatsuboshi" and "Fukkurinko". Other successful examples thereof include breeding by anther culture in rice, tobacco, and wheat.

The haploid of a fish can be induced by artificial gynogenesis or androgenesis. The former is obtained by fertilizing a normal egg by a spermatozoon genetically inactivated with ultraviolet irradiation or the like, and the latter, by fertilizing a genetically inactivated egg by a normal spermatozoon (Non Patent Literature 1). However, most of these haploids thus obtained are susceptible to death. To produce a pure line from each of the haploids, it is necessary to double the chromosome of a haploid embryo by the first cleavage suppression. The individuals produced by this method are full homozygotes; thus, the use of genetically identical gametes produced thereby enables the production of new useful varieties or clonal lineages in a short period of time (Non Patent Literature 1). However, the rate of success in haploid doubling using this method is reported to be extremely low (Non Patent Literature 1). The reasons for this are probably a problem of side effects of the first cleavage treatment per se and death or reduced ability of reproduction due to the expression of a malignant recessive gene by homogenotization (Non Patent Literature 1). Accordingly, there is a need for a stable technique for inducing clonal gametes by a method different from the above technique. A haploid individual is generally susceptible to death for a vertebrate; however, a haploid-diploid chimera goldfish (*Carassius auratus*) is viable which was prepared by combining a haploid embryo with a normal diploid embryo (Non Patent Literature 2). A haploid-diploid mosaic adult char (*Salvelinus leucomaenis*) whose organs are formed by not only haploid cells but also diploid cells is also reported (Non Patent Literature 3). These reports show that the susceptibility of haploid to death is reduced when haploid cells are mixed with normal diploid cells to form cell organs and an individual. This indicates that although a haploid individual is susceptible to death, haploid cells can survive in a normal diploid individual.

For a loach (*Misgurnus anguillicaudatus*), a clonal diploid lineage is present in some wild populations (Non Patent Literature 4). This loach is suggested to have 2 pairs of different haploid genomes from the analysis of microsatellite marker loci of haploid eggs produced by a clone-derived triploid thereof, and deduced to be a hybrid origin (Non Patent Literature 5). A female natural clonal loach forms unreduced diploid eggs genetically identical to somatic cells of itself (Non Patent Literature 6), and maintains a clonal lineage by gynogenesis without the genetic involvement of a paternal sperm (Non Patent Literature 7). For a male, a rarely occurring clonal diploid-triploid mosaic forms a diploid sperm (Non Patent Literature 8), and a male obtained by artificially sex reversing a clone is also known to form a diploid sperm (Non Patent Literature 9). It has been demonstrated from cytological observation that the mechanism of "premeiotic endomitosis" is involved in the unreduced gamete formation seen in female and male clonal loaches (Non Patent Literatures 6 and 10). Specifically, two sister chromosomes originating from the same chromosome, produced by chromosome doubling, are replicated and paired just like homologous chromosomes to form a bivalent chromosome. Then, it continuously divides two times in the same mode as that for normal meiosis to form unreduced eggs. Although cross-over or recombination occurs, no genetic variation occurs because of the exchange of elements between originally the same sister chromosomes.

The above results suggest that when hybrid origin or the like makes the pairing of different chromosomes difficult, chromosome doubling occurs before meiosis by an unexplained molecular and cellular mechanism. Thus, it is probable that a haploid germ cell having no chromosome to be paired has the possibility of autonomously doubling its chromosome without special treatment. If this occurs, the same phenomenon as genomic doubling in the anther culture can also be expected to occur in a fish haploid germ cell.

Primordial germ cells (hereinafter referred to as "PGC" or "PGCs"), even if they are haploid, transplanted into a diploid host have the possibility of surviving in the host. In addition, if the transplanted haploid PGCs undergo endomitosis in the host before meiosis, homogenotization can probably occur as in the anther culture to produce the formation of genetically identical gametes. Thus, the above mechanism is expected to enable clonal gametes to be obtained. However, it has been not clear whether for a fish, haploid PGCs can proliferate and differentiate into functional gametes in the host.

CITATION LIST

Non Patent Literature

Non Patent Literature 1: Katsutoshi Arai (1997) Chromsome Manipulation, "Fish DNA", in Takashi Aoki, Fumio Takashima, Tetsuya Hirano (Eds.), Kouseisha-koseikaku, Tokyo, pp 32-62.

Non Patent Literature 2: Tanaka M, Yamaha E, Arai K (2004) Survival capacity of Haploid-diploid goldfish chimeras. Journal of experimental Zoology 301A: 491-501.

Non Patent Literature 3: Yamaki M, Kawakami K, Taniura K, Arai K (1999) Live haploid-diploid mosaic chary *Salvelinus leucomaenis*. Fisheries Science 65: 736-741.

Non Patent Literature 4: Morishima K, Horie 5, Yamaha E, Arai K (2002) A cryptic clonal line of the loach *Misgurnus anguillicaudatus* (Teleostei: Cobitidae) evidenced by induced gynogenesis, interspecific hybridization, microsatellite genotyping and multilocus DNA fingerprinting. Zoological Science 19: 565-575.

Non Patent Literature 5: Morishima K, Yoshikawa H, Arai K (2008) Meiotic hybridogenesis in triploid Misgurnus loach derived from a clonal lineage. Heredity 100: 581-586.

Non Patent Literature 6: Itono M, Morishima K, Fujimoto T, Bando E, Yamaha E, Arai K (2006) Premeiotic endomitosis produces diploid eggs in the natural clone loach, *Misgurnus anguillicaudatus* (Teleostei: Cobitidae). Journal of experimental Zoology 305A: 513-523.

Non Patent Literature 7: Itono M, Okabayashi N, Morishima K, Fujimoto T, Yoshikawa H, Yamaha E, Arai K (2007) Cytological mechanisms of gynogenesis and sperm incorporation in unreduced diploid eggs of the clonal loach Misgrunas anguillicaudatus (Teleostei: Cobitidae). Journal of experimental zoology 307A: 35-50.

Non Patent Literature 8: Morishima K, Oshima K, Horie S, Fujimoto T, Yamaha E, Arai K (2004) Clonal diploid sperm of the diploid-triploid mosaic loach, *Misgurnus anguillicaudatus* (Teleostei: Cobitidae). Journal of experimental Zoology 301A: 502-511.

Non Patent Literature 9: Yoshikawa H, Morishima K, Kusuda S, Yamaha E, Arai K (2007) Diploid sperm produced by artificially sex reversed clone loaches. Journal of experimental Zoology 307A: 75-83.

Non Patent Literature 10: Yoshikawa H, Morishima K, Fujimoto T, Saito T, Kobayashi T, Yamaha E, Arai K (2009) Chromosome doubling in early spermatogonia produces diploid spermatozoa in a natural clonal fish. Biology of Reproduction 80: 973-979.

SUMMARY OF INVENTION

Technical Problem

In fish breeding, it is necessary to establish a technique for obtaining genetically clonal gametes without producing side effects due to cleavage suppression at induction of parthenogenesis, or without a reduction in the survival rate attributed to defective morphogenesis due to a revealed recessive deleterious gene arising from the genetic composition of an individual per se.

Thus, an object of the present invention is to provide a method for enabling the migration to the genital ridge, proliferation, and differentiation to gametes of the haploid PGCs obtained by chromosome manipulation using a developmental engineering method including a germ line chimera technique. In other words, an object of the present invention is to provide a method for obtaining a germ line chimeric fish having fish haploid germ cells. Another object of the present invention is to provide a germ line chimeric fish having haploid germ cells obtained by the method. Another object of the present invention is to provide genetically identical gametes derived from donor haploid germ cells, produced by a germ line chimeric fish obtained by the method.

Solution to Problem

As a result of intensive studies, the present inventors have accomplished the present invention as described below.

The present invention does not use the first cleavage suppression method used by a conventional method at all. According to the present invention, the genome of an egg or sperm is completely destroyed using ultraviolet rays or radioactive rays and then fertilized with a normal sperm or egg to provide an androgenetic haploid or a gynogenetic haploid. Essentially, haploids induced by these methods are each susceptible to death as an individual. Accordingly, a primordial germ cell (PGC) as a germ line cell is removed from a haploid susceptible to death as an individual and transplanted into a sterilized host that has had the dead end gene knocked down and lost its germ cells by apoptosis to induce a germ line chimera in which the host germ cells are replaced with germ cells derived from donor haploid PGCs in the gonad of the host.

Thus, the present invention is as follows.

Item 1 A method for acquiring a chimeric fish having a haploid germ cell, comprising the steps of:

a) genetically inactivating a fish egg or a fish sperm, followed by insemination to provide a haploid donor fertilized egg;

b) obtaining a fertilized egg of a host fish; and c) transplanting a donor primordial germ cell obtained from a haploid donor embryo developed from the haploid donor fertilized egg into a host embryo derived from the host fertilized egg.

Item 2 The method according to item 1, wherein the fish is loach.

Item 3 The method according to item 1, wherein the fish is goldfish.

Item 4 The method according to item 1, wherein the fish is zebrafish.

Item 5 The method according to any of items 1 to 4, wherein the genetic inactivation of an egg or a sperm is performed by ultraviolet irradiation or radiation irradiation.

Item 6 The method according to item 2 or 3, wherein the host fish is a sterile host fish obtained by the fertilization of a normal polyploid egg by a diploid sperm of a tetraploid fish.

Item 7 The method according to any one of items 1 to 6, wherein the donor is a color mutant or a genetic recombinant.

Item 8 The method according to any one of items 1 to 7, wherein the method for sterilizing the host fish involves knocking down a dead end gene in the host fertilized egg.

Item 9 The method according to item 8, wherein the knocking down is injecting a dead end antisense morpholino oligonucleotide into the host fertilized egg.

Item 10 The method according to any one of items 1 to 9, wherein a separate marker is introduced into each of the haploid donor fertilized egg and the host fertilized egg to distinguish therebetween.

Item 11 The method according to item 10, wherein the marker is a fluorescent mRNA.

Item 12 The method according to item 11, wherein the fluorescent mRNA is GFP nos 1 3'UTR mRNA or DsRed nos 1 3'UTR mRNA.

Item 13 The method according to any one of items 1 to 12, wherein the transplantation is carried out by a blastomere transplantation method (hereinafter also referred to as a BT method), a single primordial germ cell transplantation method (hereinafter also referred to as an SPT method), a poly primordial germ cell transplantation method (hereinafter also referred to as a PPT method), or a blastoderm transplantation method (hereinafter referred to as a Sandwich method).

Item 14 The method according to any one of items 1 to 13, wherein the donor or host fertilized egg is obtained, followed by removing the membrane of the egg.

Item 15 A method for acquiring genetically identical gametes by the method according to any one of items 1 to 14.

Item 16 Genetically identical gametes obtained by the method according to item 15.

Item 17 A chimeric host fish having a haploid primordial germ cell derived from a haploid germ cell.

Item 18 The chimeric host fish according to item 17, wherein the chimeric host fish is a sterilized individual.

Item 19 Genetically identical gametes obtained from the chimeric host fish according to item 17 or 18.

Item 20 A haploid clonal fish gamete derived from a haploid primordial germ cell.

Item 21 The haploid clonal fish gamete according to item 20, wherein the fish is a loach, a goldfish, or a zebrafish.

Item 22 A chimeric fish embryo comprised of a haploid donor-derived haploid primordial germ cell and a host fish embryo.

Item 23 The fish embryo according to item 22, wherein the host fish embryo is a sterilized individual.

Advantageous Effects of Invention

According to the present invention, a method can be provided which enables the migration to the genital ridge, proliferation, and differentiation to gametes of the haploid PGCs obtained by chromosome manipulation using a developmental engineering method including a germ line chimera technique. The method for obtaining the germ line chimeric fish having fish haploid primordial germ cells and the germ line chimeric fish having haploid primordial germ cells obtained by the method according to the present invention can be widely used in all fields such as genetics, embryology, physiology, immunology, and pathology. In marine products breeding, a good lineage having heterosis can be established in a short period of time by using a clonal gamete obtained from a germ line chimera having haploid PGCs obtained by the present invention to make a heteroclone.

DESCRIPTION OF EMBODIMENTS

Figure 1:
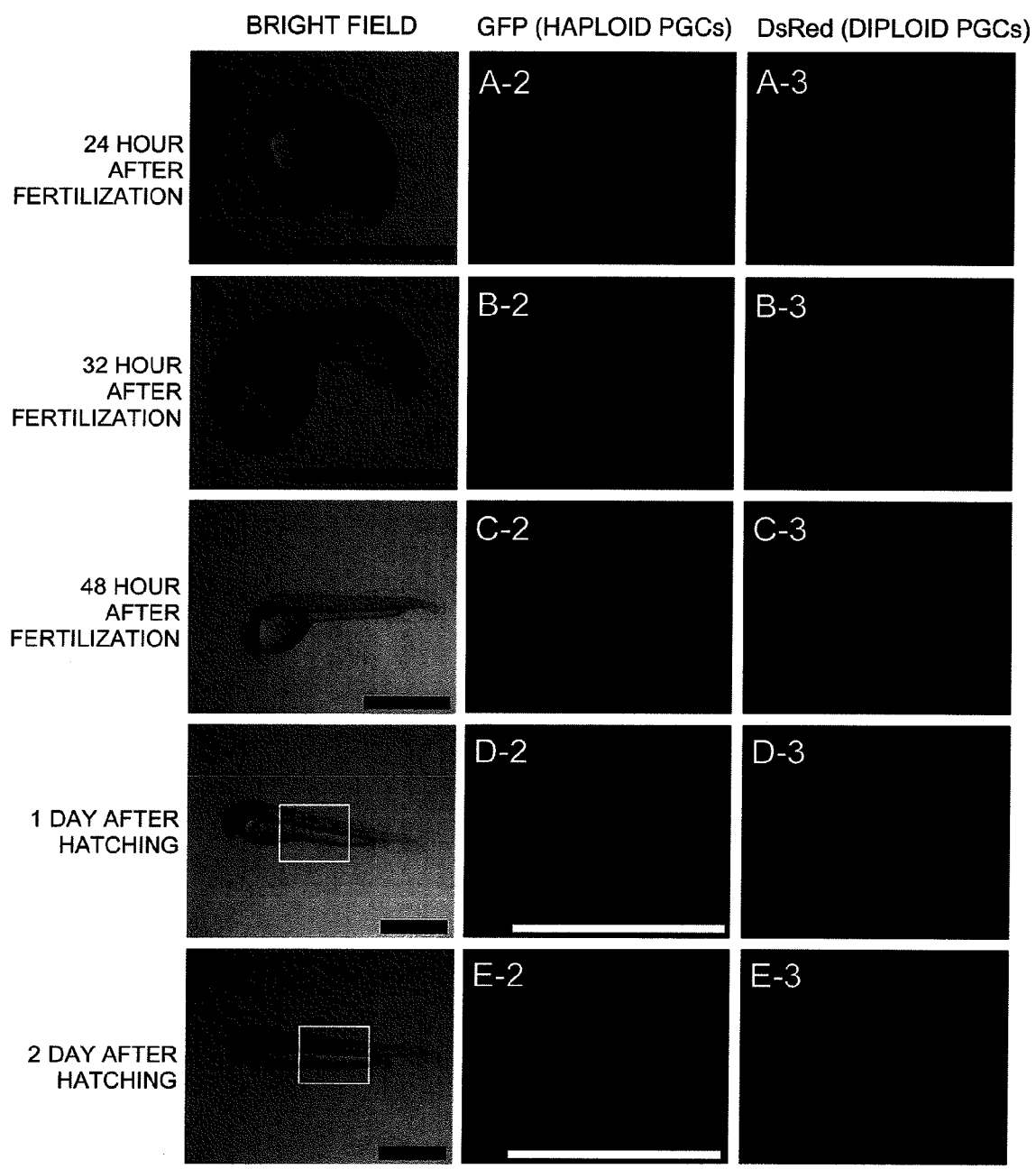
FIG. 1 is a series of photographs showing dynamic states of donor haploid PGC and host diploid PGC in the developmental process of a haploid-diploid chimeric (hereinafter also referred to as "1n-2n") loach. (A) 24 hours after fertilization, (B) 32 hours after fertilization, (C) 48 hours after fertilization, (D) 1 day after hatching, (E) 2 days after hatching, (1) brightfield image, (2) GFP dark field; the GFP fluorescence-emitting cells are donor PGCs, and (3) DsRed dark field; a DsRed fluorescence-emitting cells are host PGCs. The scale bar indicates 1 mm.

Preferred aspects are described below.

According to the present invention, the fish may be a freshwater fish or a marine fish. Preferred examples thereof include a loach, *Misgurnus anguillicaudatus*, and its mutants, an orange loach ("hidojo" in Japanese) and albino loach, a goldfish, *Carassius auratus*, and a zebrafish, *Danio rerio*.

For the purpose of the present invention, the haploid donor refers to a fish providing fish haploid (1n) primordial germ cells, obtained by gynogenesis or androgenesis. The type of a fish is not particularly limited provided that it provides the haploid.

For the purpose of the present invention, the haploid clonal fish gamete refers to a population of fish gametes having a genetically identical haploid (1n); however, one clonal gamete belonging to this population is also included within the scope of this invention.

For the purpose of the present invention, the chimera refers to an individual composed of cells having different genotypes. For the purpose of the present invention, it refers to, for example, a haploid-diploid germ line chimera (1n-2n) using a haploid as a donor and a normal diploid as a host or a haploid-triploid germ line chimera (1n-3n) using a haploid as a donor and a triploid as a host.

For the purpose of the present invention, the tetraploid fish refers to a tetraploid obtained by the inhibition of 2nd polar bodies emission after the artificial fertilization between a natural tetraploid male and a diploid female, that is, a neo-tetraploid.

For the purpose of the present invention, the chimeric fish embryo having haploid primordial germ cells refers to a fish embryo obtained by transplanting primordial germ cells of a haploid donor into a host fish embryo. A method for transplantation is not particularly limited provided that the primordial germ cells obtained from the donor can be effectively transplanted into the embryo of the host fish. Typically, blastomeres in the lower part of the blastoderm of a donor embryo at the blastula stage are transplanted into the embryo of a fish host at the blastula stage according to a blastomere transplantation method (hereinafter also referred to as "BT method"). As another method, 1 to 5 primordial germ cells manifesting themselves in a donor embryo at the somitogenesis stage may also be transplanted into the lower part of the blastoderm of a fish host embryo at the blastula stage by a single primordial germ cell transplantation method (hereinafter also referred to as "SPT method"). Alternatively, transplantation may also be performed by a poly primordial germ cell transplantation method (hereinafter also referred to as "PPT method") for transplanting a plurality thereof. In addition, primordial germ cells of a haploid donor may be transplanted into a host fish embryo by a blastoderm transplantation method (hereinafter referred to as "Sandwich method") which involves cutting away the lower part of the blastoderm and transplanting the resultant into the midportion of the host blastula.

According to the present invention, the method for genetically inactivating an egg or a sperm to obtain a haploid donor is, for example, UV irradiation or radiation irradiation; however, the method is not limited thereto provided that it can genetically inactivate the egg or the sperm or involves treatment for inducing development of only the female nucleus or only the male nucleus.

For the purpose of the present invention, the host refers to a fish embryo into which haploid primordial germ cells are to be transplanted, or a fish having proliferated from the embryo. The host does not necessarily need to be sterile provided that it is a fish from which a gamete originating from a donor primordial germ cell can be specifically separated. Alternatively, it may also be a host having a low degree of sterility. Preferred is, for example, a sterile fish such as a triploid host (3n) obtained by the insemination between a common diploid egg and a diploid sperm of a tetraploid fish.

According to the present invention, the discrimination of a primordial germ cell is not particularly limited provided that it uses a marker enabling the primordial germ cell to be specifically discriminated. The discrimination can be preferably performed using an artificial GFP nos1 3' UTR mRNA in which the structural gene of GFP is bound to 3' UTR of nos1 gene transcript, or a fluorescent mRNA enabling the specific discrimination of a primordial germ cell, such as DsRed nos1 3' UTR mRNA. In this study, GFP nos1 3'UTR mRNA and DsRed nos1 3'UTR mRNA were used according to KOPRUNNER, M., THISSE, C., THISSE, B. and RAZ, E. (2001) A zebrafish nanos-related gene is essential for the development of primordial germ cells. Genes. Dev. 15: 2877-2885.

A haploid donor derived from a color mutant (recessive character) or a recombinant individual may also be used as the haploid donor to discriminate whether the offspring derived from the haploid donor is obtained, from the color of the resultant offspring. For example, for a loach, a color mutant (recessive character), an orange loach or an albino loach may also be used as the donor. For a zebrafish, a color mutant (recessive character), a golden lineage or recombinant individual may also be used as the donor.

According to the present invention, the sterile host is not particularly limited. A host may be used which itself has germ cells which cannot, however, produce fertilizable gametes. In a triploid or hybrid generally said to be sterile, the meiotic process of forming gametes cannot normally proceed; thus, the gamete formation stops. Even when some germ cells undergo meiosis, gametes having extremely low fertilization ability are formed; even if they are fertilized, viable individuals are very rarely born. A host without endogenous germ cells may also be used. Such a host cannot produce gametes because of missing of founder cells for producing gametes even when it reaches the age and individual size of maturity and expresses secondary sexual characteristics.

According to the present invention, the method for sterilizing a host is not particularly limited. The loss of germ cells may be induced for "sterilization" by triplication, hybrid induction by crossing, or the specific knocking down of gene. Knocking-down tools include, but not limited to, gripNA and siRNA. The knocking-down is preferably performed by injecting into the embryo a dead-end antisense morpholino oligonucleotide having a sequence specially designed to knock down a dead-end gene (the dead-end gene refers to a gene essential for germ cell formation involved in the survival/migration/maintenance of host PGC). Donor-derived primordial germ cells can be surely developed in a host individual by sterilization using the dead-end antisense morpholino oligonucleotide in addition to the induction of a triploid or a hybrid.

Material and Method

1. The loach *Misgurnus anguillicaudatus*, the goldfish *Carassius auratus*, or the zebrafish *Danio rerio* is used as a material to produce a haploid-diploid germ line chimera (1n-2n) using a haploid as a donor and a normal diploid as a host and a haploid-triploid germ line chimera (1n-3n) using a haploid as a donor and a triploid as a host by a developmental engineering method as described below. The 1n-2n or 1n-3n is produced to examine whether haploid PGCs migrate to the genital ridge and proliferate as germ cells in a diploid or triploid host individual subjected to sterilization treatment by knock-down with the dead-end antisense morpholino oligonucleotide (dndMO) and whether functional gametes are formed in their gonads. To determine whether the resultant offspring is derived from the donor by pigment in the resultant offspring, when in the future it is examined whether functional gametes are formed or not, a color mutant (recessive character), an orange loach or an albino loach, is used as the donor for a loach. In addition, as a control for the 1n-3n, a diploid-triploid germ line chimera using a normal diploid as a donor and a triploid as a host (hereinafter also referred to as "2n-3n") is produced. For a goldfish, to enable the DNA identification of the resultant offspring, different individuals are used for a mother fish for obtaining a donor haploid and a mother fish for obtaining a host. For a zebrafish, a golden lineage or recombinant individual as a color mutant (recessive character) is used as a donor to determine whether the resultant offspring is derived from the donor, by pigment in the resultant offspring.

2. Genetical Inactivation of Egg and Sperm

Ultraviolet irradiation (hereinafter also referred to as "UV irradiation" or "UV") is used for the genetical inactivation of eggs and sperms. For a loach, the use of the sperm of a goldfish can remove fertilized eggs from sperms having escaped from the ultraviolet irradiation because it becomes a hybrid susceptible to death. For a goldfish, diploid sperms obtained from a tetrapolid crucian carp can be used to distinguish fertilized eggs from sperms having escaped from the ultraviolet irradiation as being triploidy. For a zebrafish, the use of the sperm of a goldfish can remove fertilized eggs obtained from sperms having escaped from the ultraviolet irradiation because they become a hybrid susceptible to death (Non Patent Literature 1).

3. Production of Haploid Donor and Diploid Host and Triploid Host

Loath eggs are inseminated with ultraviolet-irradiated goldfish sperms or ultraviolet-irradiated loach eggs with loach sperms and goldfish eggs with ultraviolet-irradiated tetraploid crucian carp sperms or zebrafish eggs with ultraviolet-irradiated goldfish sperms. Thereafter, a gynogenetic or androgenetic haploid group of donor is produced. A common diploid fertilization group as diploid hosts is also produced by the fertilization between common loach eggs and loach sperms; a common diploid fertilization group as diploid hosts, by the fertilization between common goldfish eggs and goldfish sperms; and a common diploid fertilization group, by the natural mating between common zebrafish females and common zebrafish males. In addition, the triploid fertilization group used as hosts is produced by the fertilization between common loach eggs and diploid sperms of a tetraploid loach (a tetraploid obtained by the inhibition of 2nd polar bodies emission after the artificial fertilization of a natural tetraploid male×a diploid female: a neo-tetraploid) for a loach, and by the fertilization between common goldfish eggs and diploid sperms of a tetraploid crucian carp (an individual collected from nature) for a goldfish. Loach haploid PGC was transplanted into an embryo from a loach egg×a loach sperm or a loach egg×a neo-tetraploid loach sperm; goldfish haploid PGC was transplanted into an embryo from a goldfish egg×a goldfish sperm or a goldfish egg×a tetraploid crucian carp sperm; and zebrafish haploid PGC was transplanted into a zebrafish diploid embryo. A triploid is known to have a gonad whose internal structure has many cavities and which produces the formation of large germ cells and nonmotile sperms (Fujimoto et al., Reproductive capacity of neo-tetraploid loathes produced using diploid spermatozoa from a natural tetraploid male. Aquaculture 308: S133-139 (2010)). After fertilization, unfertilized eggs are removed, and the count and removal of dead eggs and the water exchange are further performed. The morphology of hatched larval fishes is observed during the period of hatching, and the occurrence rate of normal larval fishes and the number of appearance of larval fishes showing malformations such as a haploid syndrome are investigated.

4. Removal of Egg chorion and Culture of Dechorionated Egg

For microinjection or PGC transplantation, the egg chorion is removed from fertilized eggs and the eggs are cultured until hatching according to Yamaha, E. and Yamazaki, F.: Electrically fused-egg induction and its development in the goldfish, *Carassius auratus*. Int. J. Dev. Biol. 37: 291-298 (1993), Westerfield, M.: The zebrafish book, 5th Edition; A guide for the laboratory use of zebrafish (Danio rerio), Eugene, University of Oregon Press. (2007), Fujimoto, T., Kataoka, T., Sakao, S., Saito, T., Yamaha, E. and Arai, K.: Developmental stages and germ cell lineage of the loach (*Misgurnus anguillicaudatus*). Zool. Sci. 23: 977-989. (2006).

5. Measurement of Ploidy of Donor Embryo and Host Larval Fish

To examine the success or failure of genetical inactivation of a sperm or an egg, the ploidy of the donor embryo used in producing the chimera is investigated. To examine whether a host is triploid or diploid, the ploidy of a control host larval fish from which the egg chorion is not removed is also investigated. Cells of the donor embryo and the control host larvae were mixed and dissociated in a nuclear isolation solution and a nuclear staining solution. Thereafter, the relative DNA content is measured using a flow cytometer. Here, the DNA content of the fin of the normal diploid fish employed in the experiment is used as a standard for the diploid DNA content (2C), and the DNA content of the haploid sperm of the normal diploid loach employed therein is used as a standard for the haploid DNA content (1C). When a donor having cells other than haploid cells is detected, a chimera produced using the donor is excluded from the experiment. For a loach, the donor embryo and host larval fish used for producing a 2n-3n chimera is also further examined for ploidy. The DNA content (3C) of the fin of the embryo or individual prepared from a goldfish egg×a tetraploid crucian carp sperm is used as a standard for the triploid amount.

6. Labeling of PGCs and Sterilization of Triploid Host

To distinctly visualize donor haploid and host diploid or triploid PGCs, markers, preferably GFP nos1 3'UTR mRNA emitting green fluorescence and DsRed nos1 3'UTR mRNA emitting red fluorescence are injected. Fluorescent mRNA is injected into dechorionated eggs as donors. mRNA different from that for the donor is also similarly injected into a host. At the same time, dndMO is injected to sterilize host triploid. For a zebrafish, a genetic recombinant in which PGC emits GFP fluorescence may be used.

7. Production of Germ Line Chimera

Germ line chimeras are produced by different methods. For example, according to the BT (Blastomere transplantation) method, a germ line chimera is induced by transplanting blastomeres in the lower part of the blastoderm of a donor embryo at the blastula stage into the embryo of a host at the blastula stage. As another method, it may also be induced by transplanting PGCs manifesting themselves in a donor embryo at the somitogenesis stage into the lower part of the blastoderm of a host embryo at the blastula stage by the SPT (single primordial germ cell transplantation) method or the PPT (poly primordial germ cell transplantation) method. In addition, it is also induced by cutting out the lower part of the blastoderm at the blastula stage of a haploid and transplanting the resultant into the midportion of the host blastula blastoderm by the sandwich method. The number of individuals in which haploid PGC has reached the genital ridge is counted for the produced germ line chimeric individuals. Haploid PGCs having reached the genital ridge are counted for the 1n-3n and 2n-3n produced using donor and host embryos labeled with different fluorescent mRNAs. Based on the detected number of PGCs, the chimeras are separately housed and bred in different water tanks. Here, individuals in which triploid host-derived PGC distinguished by the different fluorescence is observed are excluded from the experiment as individuals resulting from a failed sterilization of host. For 1n-3n and 2n-3n, PGCs are observed and the individuals are sampled.

8. Histological Observation

Hatched 1n-3n and 2n-3n and normal diploid (hereinafter also referred to as 2n) adult loaches (females and males), a triploid (a normal loath egg×a tetraploid loath (a neo-tetraploid obtained by the inhibition of 2nd polar bodies emission after the artificial fertilization of a natural tetraploid male×a diploid female) sperm) (hereinafter also referred to as "3n") adult loaches (a female and a male) not sterilized by dndMO treatment, hatched germ line chimeric and normal diploid (2n) adult goldfishes, and triploid (a normal goldfish egg×a tetraploid crucian carp sperm) (3n) adult goldfish (a female and a male) not sterilized by dndMO treatment are fixed and then stored in ethanol. The fixed chimeras are each sectioned to prepare tissue preparations. Thereafter, the resultants are each subjected to double staining, embedded, and then observed. For a loath, to investigate the proliferation of the developed PGCs, the undifferentiated germ cells, A-type spermatogonial cells, or oogonia of the chimeras are counted to investigate how many such cells have been proliferated relative to the number of the PGCs observed under a fluorescence microscope at the hatching juvenile stage.

9. Sperm Collection from Chimeric Male Adult Fish or Test of Fertility Potential Thereof Chorionic gonadotropic hormone (hereinafter also referred to as "hCG") is intraperitoneally injected to 1n-3n and 2n-3n male adult loaches and to 1n-3n germ line chimeric goldfish to induce spermiation or ovulation. After a certain time from injection, their abdomen is pressed and the resultant semen is collected. The collected sperms are diluted with an artificial seminal fluid to observe the semen. It is then mixed with fresh water to investigate the motility of sperms.

A germ line chimera of a zebrafish is placed in a water tank together with the normal female thereof in a proportion of 1:1 to observe ovipositional behavior and determine whether the spawned eggs include fertilized eggs or not.

10. Measurement of Ploidy of Testis, Sperm, and Ovary

Parts of the testis and the ovary are taken out from 1n-3n and 2n-3n adult loaches and germ line chimeric adult goldfish and zebrafish to investigate the ploidy thereof by flow cytometry. For loathes, the ploidy of sperms collected from 1n-3n and 2n-3n after hatching is also examined. As control, the ploidy of the testis and the ovary of 2n adult and 3n adult not sterilized by dndMO treatment is also investigated.

11. Expression of Germ Cell-Specific mRNA

To examine whether cells in the developed gonad of a chimeric adult fish are germ cells, the expression of germ cell-specific mRNA is investigated. A part of the gonad is taken out from 1n-3n and 2n-3n adult fishes, and RNA is extracted therefrom. The extracted RNA is subjected to reverse transcription to synthesize cDNA. β-actin as an internal control is also subjected to RT-PCR. The presence of the expression of germ cell-specific mRNA in the chimera gonad is identified by the PCR reaction and by electrophoresis.

12. Verification Whether or not Chimera Gamete is Derived from Donor PGC

DNAs are extracted from cells of the sperm obtained from 1n-3n germ line chimera and cells of the fin as somatic cells to demonstrate their different gene compositions using an RAPD marker.

13. Examination of Clonal Nature and Origin of Chimera Gamete

The genotype of the individual obtained by fertilization with the sperm obtained from a 1n-3n germ line chimera is examined using a microsatellite marker to determine that the genotypes of the sperm thereof are all the same.

The present invention is described below in detail, based on Examples. However, the invention is not intended to be limited by the Examples.

EXAMPLES

Case of Loach, *Misgurnus anguillicaudatus*

A. Material and Method

1. The loath *Misgurnus anguillicaudatus* was used as a material to produce a haploid-diploid germ line chimera (1n-2n) using a haploid as a donor and a normal diploid as a host and a haploid-triploid germ line chimera (1n-3n) using a haploid as a donor and a triploid as a host by a developmental engineering method as described below. The 1n-2n was produced with the object of examining whether haploid PGCs migrated to the genital ridge in the normal diploid individual like diploid PGCs. The 1n-3n was produced to examine whether haploid PGCs migrated to the genital ridge and proliferate as germ cells in a triploid host individual subjected to sterilization treatment by knock-down with the dead-end antisense morpholino oligonucleotide (SEQ ID NO: 1; 5'-GATCTGCTCCTTCCATTGCGTTTGC-3') and whether functional gametes were formed in their gonads. To determine whether the resultant offspring is derived from the donor by pigment in the offspring, when in the future it is examined whether functional gametes are formed or not, a color mutant (recessive character), an orange loach or an albino loach, was used as the donor. In addition, as a control for the 1n-3n, a diploid-triploid germ line chimera using a normal diploid as a donor and a triploid as a host (2n-3n) was produced.

2. Test Fish

In the present invention, the loach *Misgurnus anguillicaudatus* and the goldfish *Carassius auratus* reared in Aquaculture Genetics and Genomics, Graduate School of Fisheries Sciences, Hokkaido University were used as materials. The loach used was one collected in Kitamura area of Iwamizawa City, Hokkaido and Ohno Town, Hokuto City, Hokkaido, or the offspring thereof.

3. Collection of Egg and Sperm

20 IU/g of hCG (from ASKA Pharmaceutical Co., Ltd.) was intraperitoneally injected to parent loaches to induce ovulation and spermiation. In the females, ovulation was confirmed after 12 to 14 hours, followed by collecting eggs by pressing their abdomen on a plastic petri dish 90 mm in diameter covered with Saran Wrap (polyvinylidene chloride film) (from Asahi Kasei Corporation). In the males, their abdomen was also similarly pressed, and the resultant semen was subjected to the collection of sperms in a hematocrit capillary tube (from Terumo Corporation). The resultant semen was diluted about 25 times in Kurokura's solution (NaCl 750 mg, $CaCl_2$ 20 mg, $NaHCO_3$ 20 mg, KCl 20 mg/100 ml). For goldfishes, only sperms were used. 20 IU/g of hCG was intraperitoneally injected to parent goldfishes to induce spermiation. Their abdomen was pressed after 12 to 14 hours, and the resultant semen was subjected to the collection of sperms using a hematocrit capillary tube.

4. Genetical Inactivation of Egg and Sperm

Ultraviolet irradiation was used for the genetical inactivation of eggs and sperms. A box-shaped apparatus in the upper part of which two ultraviolet germicidal lamps (GL15W, from National) were placed was used. The genetical inactivation of eggs was performed by partially improving a method as described in Fujimoto et al., Journal of Experimental Zoology, 307A: 449-462, DOI: 10.1002/jez.398 (2007). Specifically, a plastic petri dish 90 mm in diameter whose bottom was knocked out, covered with Saran Wrap (from Asahi Kasei Corporation) was used as a chamber for housing eggs. A 50-mm plastic petri dish (50 mm in diameter and 10 mm in height) whose bottom was knocked out was further set in the chamber, in which about 3 ml of Hank's solution (0.137 M NaCl, 5.4 mM KCl, 0.25 mM $Na_2HPO_4$, 0.44 mM $KH_2PO_4$, 1.3 mM $CaCl_2$, 1.0 mM $MgSO_4$, 4.2 mM $NaHCO_3$) containing 0.5% bovine serum albumin was then placed and the eggs were housed so as to form one layer. Thereafter, the chamber was placed on a shaker (VS2, from Sakura Seiki Co., Ltd., Japan) and irradiated with ultraviolet rays from the top side while being horizontally shaken. The irradiation dose of ultraviolet rays was set to 150 $mJ/cm^2$. In the genetical inactivation of sperms, goldfish sperms were diluted about 100 times in Kurokura's solution, spread so as to provide a thickness of about 0.1 mm on a glass petri dish which was well washed and whose water content was wiped off, and irradiated with ultraviolet rays. The irradiation dose of ultraviolet rays was set to 60 $mJ/cm^2$. The reason why goldfishes were used is that the use of goldfish sperms in the gynogenesis of loaches can remove fertilized eggs obtained from sperms having escaped from the ultraviolet irradiation because they become a hybrid susceptible to death (Non Patent Literature 1).

5. Production of Haploid Donor and Diploid Host and Triploid Host

After inseminating loach eggs with ultraviolet-irradiated goldfish sperms or ultraviolet-irradiated loach eggs with loach sperms, a gynogenetic or androgenetic haploid group of donor was produced by a method which involves scattering the resultant in a plastic petri dish filled with tap water at 20° C. for adhesion to the bottom of the petri dish. A common fertilization group as diploid hosts was also produced by the fertilization between common loach eggs and loach sperms. After fertilization, each experimental group was cultured in an incubator set at 20° C. In addition, the triploid fertilization group used as hosts was produced by the fertilization between common loach eggs and diploid sperms of a tetraploid loach (a tetraploid obtained by the inhibition of 2nd polar body emission after the artificial fertilization of a natural tetraploid malexa diploid female: a neo-tetraploid). A triploid is known to have a gonad whose internal structure has many cavities and which produces the formation of large germ cells and nonmotile sperms different from a diploid (Fujimoto et al., Aquaculture 308: S133-139 (2010)). Within 2 hours after fertilization, unfertilized eggs were removed, and the count and removal of dead eggs every 1 day and the water exchange were further performed. The morphology of hatched larval fishes was observed during the period of hatching, and the occurrence rate of normal larval fishes and the number of appearance of larval fishes showing malformations such as a haploid syndrome were investigated. The stage of development of a loach was according to the report of Fujimoto et al. Zoological Science, 23: 977-989, DOI: 10.2108/zsj.23.977 (2006).

6. Removal of Egg Chorion and Culture of Dechorionated Egg

About a half of fertilized eggs at the 1- to 2-cell stage in each experimental group were treated with a solution for removing the egg chorion (Ringer's solution for freshwater fishes, containing 0.1% trypsin and 0.4% urea; 128 mM NaCl, 2.8 mM KCl, 1.9 mM $CaCl_2$, pH 7.0) to remove the egg chorion. Dechorionated eggs were cultured to the somitogenesis stage in a glass petri dish whose bottom face was subjected to coating treatment with about 1% agarose, filled with a primary culture solution (Ringer's solution for freshwater fishes, containing 1.6% chicken egg white, 0.01% penicillin, and streptomycin; 128 mM NaCl, 2.8 mM KCl, 1.9 mM $CaCl_2$, pH 7.0) at 20° C. Thereafter, the dechorionated eggs were transferred to a secondary culture solution (a 1.8 mM $CaCl_2$, 1.8 mM $MgCl_2$ solution containing 0.01% penicillin and streptomycin) and cultured to hatching.

7. Measurement of Ploidy of Donor Embryo and Host Larval Fish

To examine the success or failure of genetical inactivation of a sperm or an egg, the ploidy of the donor embryo used in producing the chimera was investigated using a flow cytometer (Partec Ploidy Analyser, Model PA). To examine whether a host was triploid or diploid, the ploidy of a control host larval fish from which the egg chorion was not removed was also investigated. The donor embryo and the control host larval fish were each placed in 150 μl of solution A (a nuclear isolation solution) for Cystain DNA 2 step kit (Partec) and allowed to stand for 20 minutes, and cells were mixed and dissociated by vortex. Thereafter, the specimen was filtered with a 50-μm mesh (Cell Trics 50 μm, Partec), to which solution B (a stain solution containing 4',6-diamidino-2-phenylindole (DAPI)) at a volume of 5 times that of the solution A was added after removing cell debris to measure the relative DNA content by flow cytometry. Here, the DNA content of the fin of the normal diploid loach was used as a standard for the diploid DNA content (2C), and the DNA content of the haploid sperm of the normal diploid loach employed therein was used as a standard for the haploid DNA content (1C). When a donor having cells other than haploid cells is detected, a chimera produced using the donor was excluded from the experiment. The donor embryo and host larval fish used for producing a 2n-3n chimera were also further examined for ploidy.

A. Result

1. Number of Fertilized Eggs, Number of Hatched Larval Fishes, and Number of Normal Larval Fishes in Control The donors and hosts used for the production of the chimeras are summarized in Table 1. The donor haploids were produced by gynogenesis or androgenesis, while the donor diploids were produced by normal fertilization. The hosts used were triploids or diploids (Table 1). As controls in producing chimeras, the groups of "control" in which no treatment was performed, "dechorionated control" in which the egg chorion was removed, and "fluorescent mRNA-injected control" in which fluorescent mRNA and dndMO were injected were produced. In the controls, the number of the eggs used, the number of fertilized eggs, the number of hatched larval fishes, the number of normal larval fishes, and the number of malformed larval fishes were counted. For the dechorionated control and the fluorescent mRNA-injected control, only normal fertilized eggs were selected to count the number of hatched larval fishes, the number of normal larval fishes, and the number of malformed larval fishes (Table 2). As a result, normal larval fishes were obtained from most of the individuals produced as hosts. Most of the gynogenesis and androgenesis groups produced as donors showed malformed larval fishes, which were categorized as the so-called haploid syndrome, after hatching. The egg chorion removal and the fluorescent mRNA injection in the fertilized eggs did not change the proportion of hatched larval fishes compared to the untreated controls; thus, no negative effects of these treatments were seen.

TABLE 1

Parent Fish of Donors and Hosts

| Experiment | | Sex | Sample Used for Crossing | Name in Table |
|---|---|---|---|---|
| 1 | Donor | ♀ | Loach | #1 |
| | | ♂ | Goldfish (Left Fin Cut) | Goldfish #1 |
| | Host | ♀ | Loach | #2 |
| | | ♂ | Loach | #3 |
| 2 | Donor | ♀ | Albino Loach | #4 |
| | | ♂ | Goldfish (Right Fin Cut) | Goldfish #2 |
| | Host | ♀ | Loach | #5 |
| | | ♂ | Neo-Tetraploid | 4n |
| 3 | Donor | ♀ | Orange Loach | #6 |
| | | ♂ | Goldfish (Right Fin Cut) | Goldfish #2 |
| | Host | ♀ | Loach | #7 |
| | | ♂ | Neo-Tetraploid | 4n |
| 4 | Donor | ♀ | Loach | #8 |
| | | ♂ | Goldfish (Right Fin Cut) | Goldfish #2 |
| | Host | ♀ | Loach | #9 |
| | | ♂ | Neo-Tetraploid | 4n |

TABLE 1-continued

Parent Fish of Donors and Hosts

| Experiment | | Sex | Sample Used for Crossing | Name in Table |
|---|---|---|---|---|
| 5 | Donor | ♀ | Loach | #10 |
| | | ♀ | Loach | #11 |
| | | ♂ | Orange Loach | #12 |
| | Host | ♀ | Loach | #13 |
| | | ♂ | Neo-Tetraploid | 4n |
| 6 | Donor | ♀ | Loach | #14 |
| | | ♂ | Goldfish (Right Fin Cut) | Goldfish #2 |
| | Host | ♀ | Loach | #15 |
| | | ♂ | Neo-Tetraploid | 4n |
| 7 | Donor | ♀ | Loach | #15 |
| | | ♂ | Loach | #16 |
| | Host | ♀ | Loach | #17 |
| | | ♂ | Neo-Tetraploid | 4n |
| 8 | Donor | ♀ | Loach | #17 |
| | | ♂ | Goldfish (Left Fin Cut) | Goldfish #1 |
| | Host | ♀ | Loach | #18 |
| | | ♀ | Loach | #19 |
| | | ♂ | Neo-Tetraploid | 4n |
| 9 | Donor | ♀ | Albino Loach | #20 |
| | | ♂ | Goldfish (Left Fin Cut) | Goldfish #1 |
| | | ♂ | Albino Loach | #21 |
| | Host | ♀ | Loach | #22 |
| | | ♀ | Neo-Tetraploid | 4n |

TABLE 2

Number of Fertilized Eggs and Number of Hatched Larval Fishes in Donor and Host Controls

| Experiment | | Crossing (Female×Male) | Number of Eggs Used | Fertilized Eggs | Hatched Larval Fish | Normal Larval Fish | Malformed Larval Fish |
|---|---|---|---|---|---|---|---|
| 1 | Control | #1×UV Goldfish #1 | 454 | 329 | 91 | 0 | 91 |
| | | #2×#3 | 188 | 102 | 79 | 74 | 5 |
| | Dechorionated Control | #1×UV Goldfish #1 | — | 24 | 18 | 0 | 18 |
| | | #2×#3 | — | 23 | 22 | 22 | 0 |
| | Fluorescent mRNA-Injected Control | #1×UV Goldfish #1 (Donor: GFP + Biotin) | — | 16 | 11 | 0 | 11 |
| | | #2×#3 (Host: DsRed) | — | 11 | 10 | 10 | 0 |
| 2 | Control | #4×UV Goldfish #2 | 307 | 95 | 5 | 5 | 0 |
| | | #5×4n | 352 | 288 | 64 | 64 | 0 |
| | Dechorionated Control | #4×UV Goldfish #2 | — | 24 | 1 | 0 | 1 |
| | | #5×4n | — | 24 | 22 | 21 | 1 |
| | Fluorescent mRNA-Injected Control | #4×UV Goldfish #2 (Donor: GFP + Biotin) | — | 18 | 2 | 0 | 2 |
| | | #5×4n (Host: DsRed + dnd MO) | — | 24 | 24 | 23 | 1 |
| 3 | Control | #6×UV Goldfish #2 | 129 | 73 | 44 | 0 | 44 |
| | | #7×4n | 427 | 116 | 308 | 301 | 7 |
| | Dechorionated Control | #6×UV Goldfish #2 | — | 24 | 21 | 14 | 7 |
| | | #7×4n | — | 24 | 18 | 17 | 1 |
| | Fluorescent mRNA-Injected Control | #6×UV Goldfish #2 (Donor: GFP + Biotin) | — | 24 | 21 | 17 | 4 |
| | | #7×4n (Host: DsRed + dnd MO) | — | 24 | 22 | 18 | 4 |
| 4 | Control | #8×UV Goldfish #2 | 317 | 77 | 209 | 7 | 202 |
| | | #9×4n | 155 | 126 | 27 | 27 | 0 |
| | Dechorionated Control | #8×UV Goldfish #2 | — | 24 | 23 | 19 | 3 |
| | | #9×4n | — | 8 | 6 | 6 | 0 |
| | Fluorescent mRNA-Injected Control | #8×UV Goldfish #2 (Donor: GFP + Biotin) | — | 24 | 23 | 19 | 5 |
| | | #9×4n (Host: DsRed + dnd MO) | — | 8 | 8 | 8 | 0 |
| 5 | Control | #10×#12 | 279 | 225 | 54 | 54 | 0 |
| | | UV #10×#12 | 251 | 226 | 12 | 0 | 12 |
| | | UV #11×#12 | 295 | 235 | 45 | 0 | 45 |
| | | #13×4n | 280 | 98 | 175 | 172 | 3 |
| | Dechorionated Control | UV #10×#12 | — | 0 | 0 | 0 | 0 |
| | | UV #11×#12 | — | 24 | 18 | 0 | 18 |
| | | #13×4n | — | 48 | 48 | 48 | 0 |
| | Fluorescent mRNA-Injected | UV #10×#12 (Donor: DsRed + Biotin) | — | 32 | 25 | 0 | 25 |

TABLE 2-continued

Number of Fertilized Eggs and Number of Hatched Larval Fishes in Donor and Host Controls

| Experiment | | Crossing (Female×Male) | Number of Eggs Used | Fertilized Eggs | Hatched Larval Fish | Normal Larval Fish | Malformed Larval Fish |
|---|---|---|---|---|---|---|---|
| | Control | UV #11×#12 (Donor: DsRed + Biotin) | — | 16 | 10 | 0 | 10 |
| | | #13×4n (Host: GFP + dnd MO) | — | 48 | 48 | 47 | 1 |
| 6 | Control | #14×UV Goldfish #2 | 310 | 204 | 99 | 0 | 99 |
| | | #15×4n | 321 | 43 | 174 | 170 | 4 |
| | Dechorionated Control | #14×UV Goldfish #2 | — | 48 | 42 | 0 | 42 |
| | | #15×4n | — | 32 | 32 | 31 | 1 |
| | Fluorescent mRNA-Injected Control | #14×UV Goldfish #2 (Donor: DsRed + Biotin) | — | 48 | 41 | 0 | 41 |
| | | #15×4n (Host: GFP + dnd MO) | — | 32 | 29 | 27 | 2 |
| 7 | Control | #15×#16 | 311 | 36 | 273 | 264 | 9 |
| | | #17×4n | 230 | 38 | 189 | 188 | 1 |
| | Dechorionated Control | #15×#16 | — | 48 | 42 | 39 | 3 |
| | | #17×4n | — | 64 | 63 | 63 | 0 |
| | Fluorescent mRNA-Injected Control | #15×#16 (Donor: DsRed + Biotin) | — | 48 | 47 | 47 | 0 |
| | | #17×4n (Host: GFP + dnd MO) | — | 31 | 29 | 29 | 0 |
| 8 | Control | #17×UV Goldfish #1 | 0 | 0 | 0 | 0 | 0 |
| | | #18×4n | 0 | 0 | 0 | 0 | 0 |
| | | #19×4n | 0 | 0 | 0 | 0 | 0 |
| | Dechorionated Control | #17×UV Goldfish #1 | — | 48 | 42 | 0 | 42 |
| | | #18×4n | — | 22 | 22 | 21 | 1 |
| | | #19×4n | — | 24 | 24 | 22 | 2 |
| | Fluorescent mRNA-Injected Control | #17×UV Goldfish #1 (Donor: DsRed + Biotin) | — | 48 | 44 | 0 | 44 |
| | | #18×4n (Host: GFP + dnd MO) | — | 62 | 58 | 53 | 5 |
| | | #19×4n (Host: GFP + dnd MO) | — | 68 | 63 | 55 | 8 |
| 9 | Control | #20×UV Goldfish #1 | 670 | 138 | 324 | 324 | 0 |
| | | #20×#21 | 422 | 62 | 294 | 282 | 12 |
| | | #22×4n | 345 | 274 | 65 | 65 | 0 |
| | Dechorionated Control | #20×UV Goldfish #1 | — | 48 | 41 | 0 | 41 |
| | | #20×#21 | — | 48 | 46 | 37 | 9 |
| | | #22×4n | — | 32 | 31 | 30 | 1 |
| | Fluorescent mRNA-Injected Control | #20×UV Goldfish #1 (Donor: DsRed + Biotin) | — | 32 | 27 | 0 | 27 |
| | | #20×#21 (Donor: DsRed + Biotin) | — | 40 | 39 | 28 | 11 |
| | | #22×4n (Host: GFP + dnd MO) | — | 30 | 18 | 17 | 1 |

Ultraviolet Irradiation (UV), GFP nos1 3' UTR mRNA (GFP), DsRed nos1 3' UTR mRNA (DsRed), Biotin-Dextran (Biotin), Dead End Antisense Morpholino oligonucleotide (dndMO)

2. Ploidy of Donor Embryo and Host Hatched Larval Fish

To examine the success or failure of genetical inactivation of a sperm or an egg, the ploidy of the donor embryo used in producing the chimera was investigated (Table 3). As a result, most of the donor embryos used for producing the chimera obtained from gynogenesis or androgenesis were each composed of haploid cells. However, in some embryos, the ploidy could not be detected because cells thereof are broken. Here, the chimeras were excluded which were produced from the donor embryos in which the ploidy could not be detected. Most of the donor embryos obtained by normal fertilization, used for producing 2n-3n were composed of diploid cells. Most of the host hatched larval fishes produced by the fertilization between normal eggs and diploid sperms of a neo-tetraploid loach were composed of triploid cells. However, in experiment 5, one tetraploid individual occurred in 10 individuals. It could be confirmed that most of the donors and hosts used for producing chimeras were haploid and triploid.

TABLE 3

Ploidy of Donor Embryo and Ploidy of Host Hatched Larval Fish Used for Producing Chimera

| Experiment | | Pair for Crossing | Number of Specimens | Haploid | Diploid | Triploid | Tetraploid | Not Detectable |
|---|---|---|---|---|---|---|---|---|
| 1 | Donor | #1×UV Goldfish #1 | 7 | 5 | 0 | 0 | 0 | 2 |
| | Host | #2×#3 | — | — | — | — | — | — |
| 2 | Donor | #4×UV Goldfish #2 | 3 | 3 | 0 | 0 | 0 | 0 |
| | Host | #5×4n | — | — | — | — | — | — |

TABLE 3-continued

Ploidy of Donor Embryo and Ploidy of Host Hatched Larval Fish Used for Producing Chimera

| Experiment | | Pair for Crossing | Number of Specimens | Haploid | Diploid | Triploid | Tetraploid | Not Detectable |
|---|---|---|---|---|---|---|---|---|
| 3 | Donor | #6xUV Goldfish #2 | 1 | 1 | 0 | 0 | 0 | 0 |
|   | Host | #7x4n | 20 | 0 | 0 | 20 | 0 | 0 |
| 4 | Donor | #8xUV Goldfish #2 | 3 | 1 | 0 | 0 | 0 | 2 |
|   | Host | #9x4n | 10 | 0 | 0 | 10 | 0 | 0 |
| 5 | Donor | UV #10x#12 | 4 | 4 | 0 | 0 | 0 | 0 |
|   | Donor | UV #11x#12 | 10 | 9 | 0 | 0 | 0 | 1 |
|   | Host | #13x4n | 10 | 0 | 0 | 9 | 1 | 0 |
| 6 | Donor | #14xUV Goldfish #2 | 13 | 13 | 0 | 0 | 0 | 0 |
|   | Host | #15x4n | 10 | 0 | 0 | 10 | 0 | 0 |
| 7 | Donor | #15x#16 | 19 | 1 | 18 | 0 | 0 | 0 |
|   | Host | #17x4n | 10 | 0 | 0 | 10 | 0 | 0 |
| 8 | Donor | #17xUV Goldfish #1 | 16 | 16 | 0 | 0 | 0 | 0 |
|   | Host | #18x4n | 10 | 0 | 0 | 9 | 0 | 1 |
|   | Host | #19x4n | 10 | 0 | 0 | 10 | 0 | 0 |
| 9 | Donor | #20xUV Goldfish #1 | 14 | 11 | 0 | 0 | 0 | 3 |
|   | Donor | #20x#21 | 6 | 6 | 0 | 0 | 0 | 0 |
|   | Host | #22x4n | 10 | 0 | 0 | 10 | 0 | 0 |

Ultraviolet Irradiation (UV)
The "number of specimens" for the donors indicates the number of the donor embryos used for the chimeras migrating to the genital ridge.
The "number of specimens" for the hosts indicates the number of hatched larval fishes from the untreated control hosts.

B. Material and Method

1. Labeling of PGCs and Sterilization of Triploid Host

To distinctly visualize donor haploid and host diploid or triploid PGCs, GFP nos1 3'UTR mRNA emitting green fluorescence and DsRed nos1 3'UTR mRNA emitting red fluorescence were injected (Koprunner, et al., Genes. Dev. 15: 2877-2885 (2001)). 0.2 M KCl containing 100 ng/µl of fluorescent mRNA and 5% biotin dextran (from SIGMA) was microinjected into dechorionated eggs at the 1- to 2-cell stage as donors. For the hosts, 0.2 KCl containing 100 ng/µl of mRNA and 10% biotin dextran, different from that for the donors was microinjected. At the same time, 2,000 to 4,000 pg/embryo of dndMO for sterilizing the host triploids was microinjected.

2. Production of Germ Line Chimera

Germ line chimeras were attempted to be produced by different methods. First, according to the BT (Blastomere transplantation) method, a germ line chimera was induced by transplanting blastomeres in the lower part of the blastoderm of a donor embryo at the blastula stage into the embryo of a host at the blastula stage. As another method, it was induced by transplanting 1 to 5 PGCs manifesting themselves in a donor embryo at the somitogenesis stage into the lower part of the blastoderm of a host embryo at the blastula stage by the SPT (single primordial germ cell transplantation) method. Haploid PGCs having reached the genital ridge were counted for the 1n-3n and 2n-3n produced using donor and host embryos labeled with different fluorescent mRNAs. Based on the detected number of PGCs, the chimeras were separately housed and bred in different water tanks. Here, individuals in which triploid host-derived PGC distinguished by the different fluorescence was observed were excluded from the experiment as a host the sterilization of which had failed. For 1n-3n and 2n-3n, PGCs were observed under a fluorescence microscope until 8 days after hatching, and 5 to 10 individuals each 1, 2, 4, 12, 15.5, and 16 months after hatching were sampled.

B. Result

1. Migration of Haploid PGCs to Genital Ridge

The migration of PGCs in the chimera embryo was observed. As a result of observing 1n-2n chimeras (experiment 1 in Table 4) under a fluorescence microscope, donor 1n-derived PGCs into which GFP fluorescence mRNA was injected were found to emit green fluorescence (FIG. 1). Host 2n-derived PGCs into which DsRed fluorescence mRNA was injected were found to emit red fluorescence (FIG. 1). Donor 1n- and host 2n-derived PGCs were positioned in almost the same place at the somitogenesis stage after transplantation (A2,3, B2,3, C2,3 in FIG. 1), and all PGCs migrated to the genital ridge at the hatching stage (D2,3, E2,3 in FIG. 1; experiment 1 in Table 4). Thereafter, donor 1n and host 2n PGCs could be all demonstrated to be localized in the genital ridge until 8 days after hatching. In 2n-3n chimeras, donor 2n-derived PGCs migrated to the genital ridge at the hatching stage in the triploid hosts sterilized by dndMO treatment (experiments 7 and 9 in Table 4). In 1n-3n chimeras, donor 1n PGCs migrated to the genital ridge at the hatching stage in the triploid hosts sterilized by dndMO treatment (experiments 2, 3, 4, 5, 6, 8, and 9 in Table 4), as in the 2n-3n chimeras. In the chimeras using 3n treated with dndMO as hosts, host-derived PGCs were not observed (experiments 2, 3, 4, 5, 6, 7, 8, and 9 in Table 4).

It turned out that the donor-derived haploid PGCs migrated to the genital ridge in the hosts like the host diploid-derived PGCs. In addition, the donor-derived PGCs also migrated to the genital ridge in the host triploids sterilized by dndMO treatment. From the above results, it was demonstrated that for a loach, PGCs had the ability to migrate to the genital ridge even when they were derived from a haploid donor which is susceptible to death.

2. Production of Germ Line Chimera

In the chimeras produced in all experiments, many hatched larval fishes were obtained, and the proportion of individuals was high for which larval fishes showed normal morphologies (Table 4). In addition, the position of donor PGCs in normal larval fishes was examined under a fluorescence microscope, and simultaneously the presence (+) and absence (−) of host PGCs were examined. PGCs derived from the hosts sterilized by dndMO treatment were not observed in the individuals in which donor PGCs were identified in the genital ridge. As shown in Table 3, among chimeras in which donor derived PGCs were identified in the genital ridge, chimeras for which donor embryos were demonstrated to be haploid were used as due germ line chimera. Incidentally, although the two methods for producing a chimera were used, the SPT method could more efficiently induce germ line chimeras in which donor PGCs migrated to the genital ridge than BT method.

(a female and a male) not sterilized by dndMO treatment were fixed in Bouin's fluid (a picric acid saturated solution:formalin:acetic acid=15:5:1) for 6 to 12 hours and then stored in 80% ethanol. The fixed chimeras were dehydrated with ethanol series or butanol series; for the ethanol series, they were each lucidified in xylene and embedded in paraffin. The embedded paraffin block was sectioned at a thickness of 6 or 8 μm with a microtome to prepare a tissue preparation. Then, the resultant was subjected to hematoxylin-eosin double stain, and observed after inclusion. From Fujimoto et al. (Sexual dimorphism of gonadal structure and gene expression in germ cell-deficient loach, a teleost fish. PNAS, 107 (40): 17211-17216 (2010)), it has been shown that an individual sterilized by dndMO treatment has an undeveloped tube-like testis structure lacking germ cells for a male and

TABLE 4

Number of Hatched Larval Fishes of Chimera, Position of Donor PGC, and Presence or Absence of Host PGC

| Experiment | Chimera Production Method | Chimera Donor | Host | Number of Chimeras | Hatched Larval Fish | Normal Larval Fish | Malformed Larval Fish | Position Of Donor PGCs in Normal Larval Fish | | | Presence or Absence of Host PGCs | Number of Germ Line Chimeras |
|---|---|---|---|---|---|---|---|---|---|---|---|---|
| | | | | | | | | None | Ectopia | Genital Ridge | | |
| 1 | Transplantation to Blastoderm | 1n-2n #1xUV Goldfish #1 (GFP + Biotin) | #2x#3 (DsRed) | 79 | 64 | 41 | 23 | 32 | 1 | 8 | 8(+) 0(−) | 5 |
| 2 | Transplantation to Blastoderm | 1n-3n #4xUV Goldfish #2 (GFP + Biotin) | #5x4n (DsRed + dnd MO) | 74 | 67 | 53 | 14 | 53 | 0 | 3 | 0(+) 3(−) | 3 |
| 3 | Transplantation to Blastoderm | 1n-3n #6xUV Goldfish #2 (GFP + Biotin) | #7x4n (DsRed + dnd MO) | 78 | 65 | 42 | 23 | 41 | 0 | 1 | 0(+) 1(−) | 1 |
| 4 | Transplantation to Blastoderm | 1n-3n #8xUV Goldfish #2 (GFP + Biotin) | #9x4n (DsRed + dnd MO) | 22 | 15 | 11 | 4 | 8 | 0 | 3 | 0(+) 3(−) | 3 |
| 5 | SPT | 1n-3n #10x#12 (DsRed + Biotin) #11x#12 (DsRed + Biotin) | #13x4n (GFP + dnd MO) | 52 | 50 | 43 | 7 | 13 | 15 | 15 | 0(+) 15(−) | 15 |
| 6 | SPT | 1n-3n #14xUV Goldfish #2 (DsRed + Biotin) | #15x4n (GFP + dnd MO) | 60 | 52 | 46 | 6 | 4 | 29 | 13 | 0(+) 13(−) | 13 |
| 7 | SPT | 2n-3n #15x#16 (DsRed + Biotin) | #17x4n (GFP + dnd MO) | 126 | 119 | 108 | 11 | 11 | 21 | 76 | 0(+) 76(−) | 75 |
| 8 | SPT | 1n-3n #17xUV Goldfish #1 (DsRed + Biotin) | #18x4n (GFP + dnd MO) #19x4n (GFP + dnd MO) | 122 | 113 | 102 | 11 | 19 | 23 | 60 | 0(+) 60(−) | 60 |
| 9 | SPT | 1n-3n #20xUV Goldfish #1 (DsRed + Biotin) | #22x4n (GFP + dnd MO) | 81 | 76 | 71 | 5 | 10 | 23 | 38 | 0(+) 38(−) | 30 |
| | | 2n-3n #20x#21 (DsRed + Biotin) | | 20 | 12 | 10 | 2 | 2 | 5 | 3 | 0(+) 3(−) | 3 |

Ultraviolet Irradiation (UV)
GFP nos1 3' UTR mRNA (GFP), DsRed nos1 3' UTR mRNA (DsRed), Biotin-Dextran (Biotin), Dead End Antisense Morpholino oligonucleotide (dndMO)

C. Material and Method
1. Histological Observation 1n-3n and 2n-3n and normal diploid (2n) adult loaches (females and males) 1-, 2-, 4-, 12-, 15.5-, and 16-month old after hatching and a triploid (a normal loach egg×a tetraploid loach (a neo-tetraploid obtained by the inhibition of 2nd polar bodies emission after the artificial fertilization of a diploid female×a natural tetraploid male) sperm) (3n) adult loaches also has an undeveloped ribbon-like ovary structure lacking germ cells for a female; thus, according to the present invention, dndMO-treated 3n were not particularly produced as a sterilized control group. To investigate the proliferation of developed PGC, the undifferentiated germ cells, A-type spermatogonial cells, or oogonia of 1-, 2-, 4-, 12-, 15.5-, and 16-month old chimeras were counted to investigate how many such cells had been proliferated relative to the number of the PGCs observed under a fluorescence microscope at the hatching juvenile stage.

2. Sperm Collection from Chimeric Male Adult Fish

20 IU/g of hCG was intraperitoneally injected to 1n-3n and 2n-3n male adult fish 12-month old over 2 days to induce spermiation. On day 2, 12 to 14 hours after injection, their abdomen was pressed and the resultant semen was collected using a hematocrit capillary tube. The resultant semen was diluted about 10 times in Kurokura's solution. The diluted semen was observed for morphology under a light microscope. It was then mixed with fresh water to investigate the motility of sperms.

Figure 7:
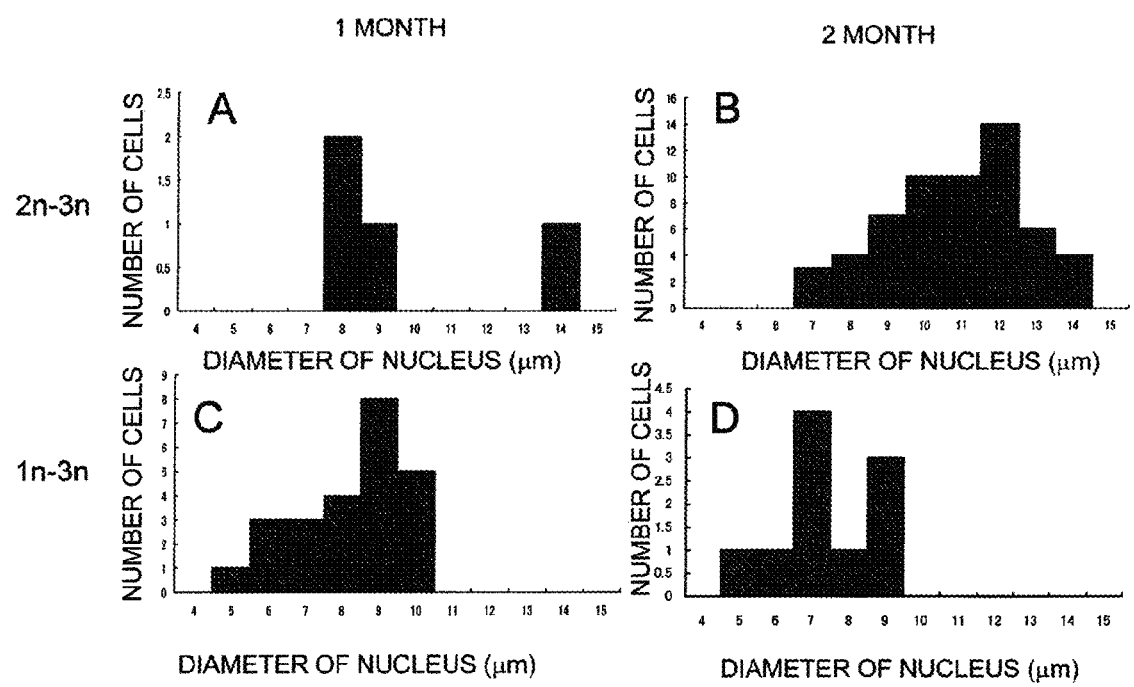
FIG. 7 is a series of graphs showing the frequency of the diameter of undifferentiated germ cell nuclei in 1- and 2-month old 2n-3n chimeric and 1n-3n chimeric loaches. (A) the 1-month old 2n-3n chimera, (B) the 2-month old 2n-3n chimera, (C) the 1-month old 1n-3n chimera, and (D) the 2-month old 1n-3n chimera.
Figure 8:
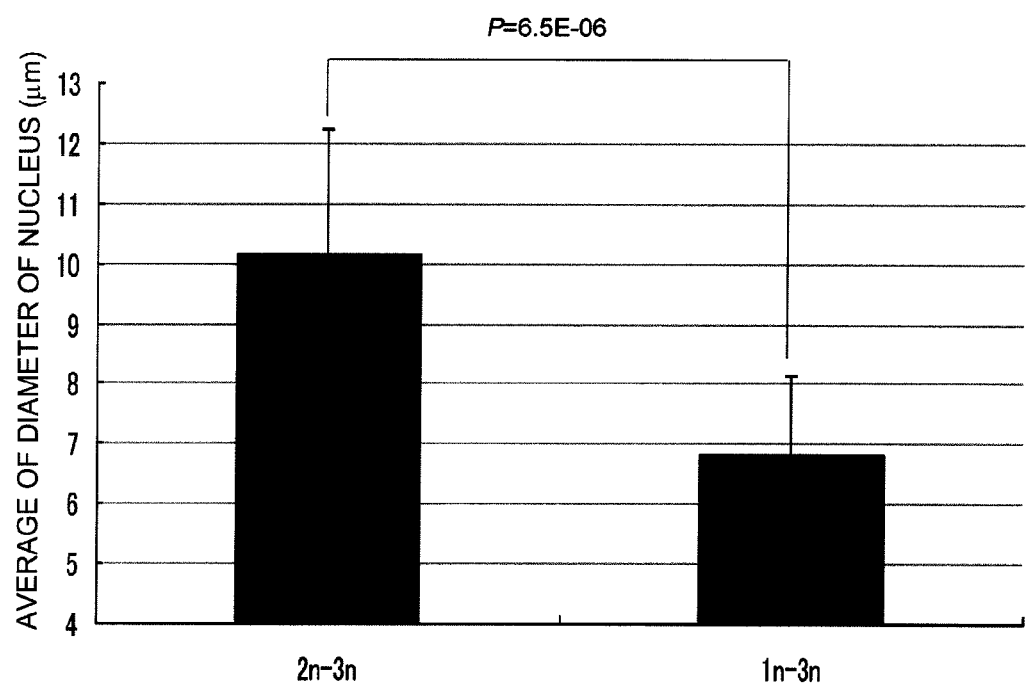
FIG. 8 is a graph showing the average size of undifferentiated germ cell nuclei in 2-month old 2n-3n chimeric and 1n-3n chimeric loaches. The error bar indicates a standard deviation. A significant difference was observed between both chimeras. (Student' t-test, P<0.01)
Figure 9:
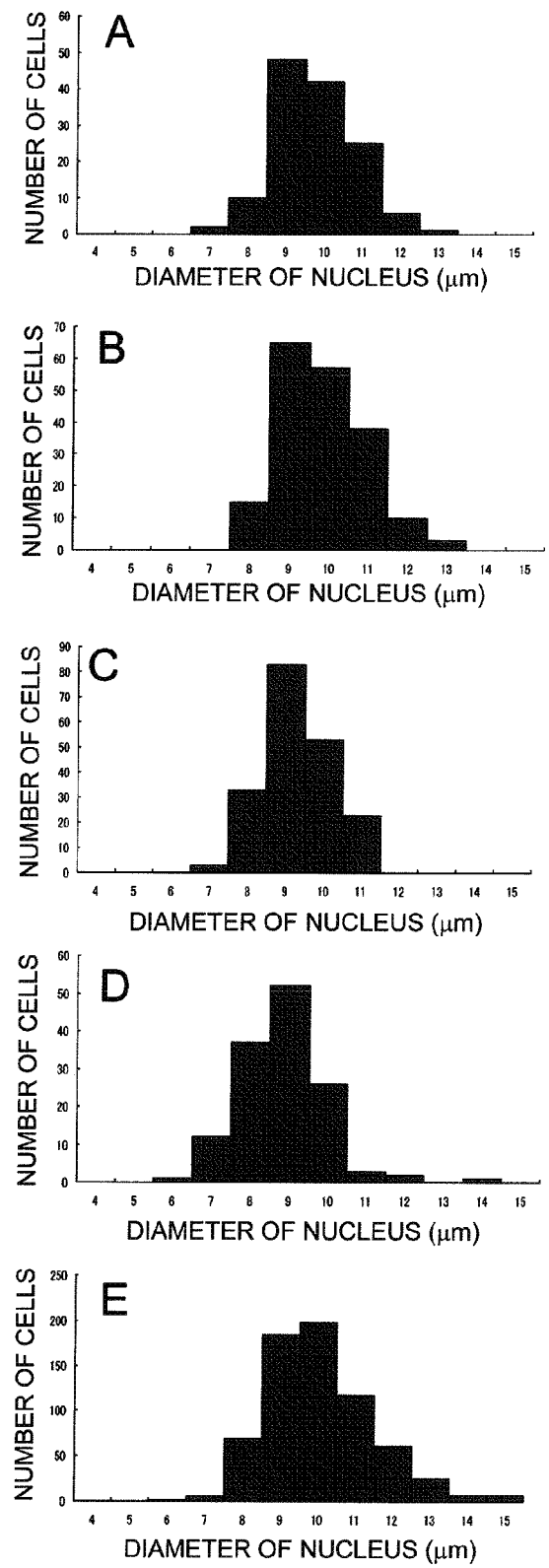
FIG. 9 is a series of graphs showing the frequency of the diameter of A-type spermatogonial cell nuclei in normal diploid, triploid (derived from the crossing of a diploid female and a tetraploid male), 2n-3n chimeric, and 1n-3n chimeric adult loaches. (A) the normal diploid, (B) the triploid derived from the crossing of a diploid female and a tetraploid male, (C) the 2n-3n chimera; Table 8, 15.5-month old Nos. 2 and 4, 16-month old No. 1, (D) the 1n-3n chimera in which spermatids and sperms were observed; Table 8, 16-month old No. 4, and (E) the 1n-3n chimera in which spermatids and sperms were not observed; Table 8, 12-month old Nos. 5 and 6, 15.5-month old No. 3, 16-month old Nos. 8 and 9.

3. Diameter of Nucleus of Undifferentiated Germ Cell, A-Type Spermatogonial Cell, and Oogonium A difference particularly in the size of A-type spermatogonial cells was observed between 1n-3n and 2n-3n from the tissue images. Thus, the diameter of nuclei of undifferentiated germ cells were measured in more detail for 1-, 2-, 4-, 12-, 15.5-, and 16-month old 1n-3n and 2n-3n (early developed cells for which it was not possible to determine whether they were A-type spermatogonial cells or oogonia), A-type spermatogonial cells, and oogonia to calculate the frequency thereof (FIGS. 7, 8, and 9). At the same time, as control, the frequency of the diameter of the A-type spermatogonial cells and oogonia of adult fishes of 2n and 3n not sterilized by dndMO treatment was determined.

4. Measurement of Ploidy of Testis, Sperm, and Ovary

Parts of the testis and the ovary were taken out from 12-, 15.5-, and 16-month old 1n-3n and 2n-3n adult fishes to investigate the ploidy thereof by flow cytometry. The ploidy of sperms collected from 1n-3n and 2n-3n 12-month old after hatching was also examined. As control, the ploidy of the testis and ovary of 2n adult and 3n adult not sterilized by dndMO treatment was also investigated.

C. Result

1. External Morphology of Gonad

Figure 2:
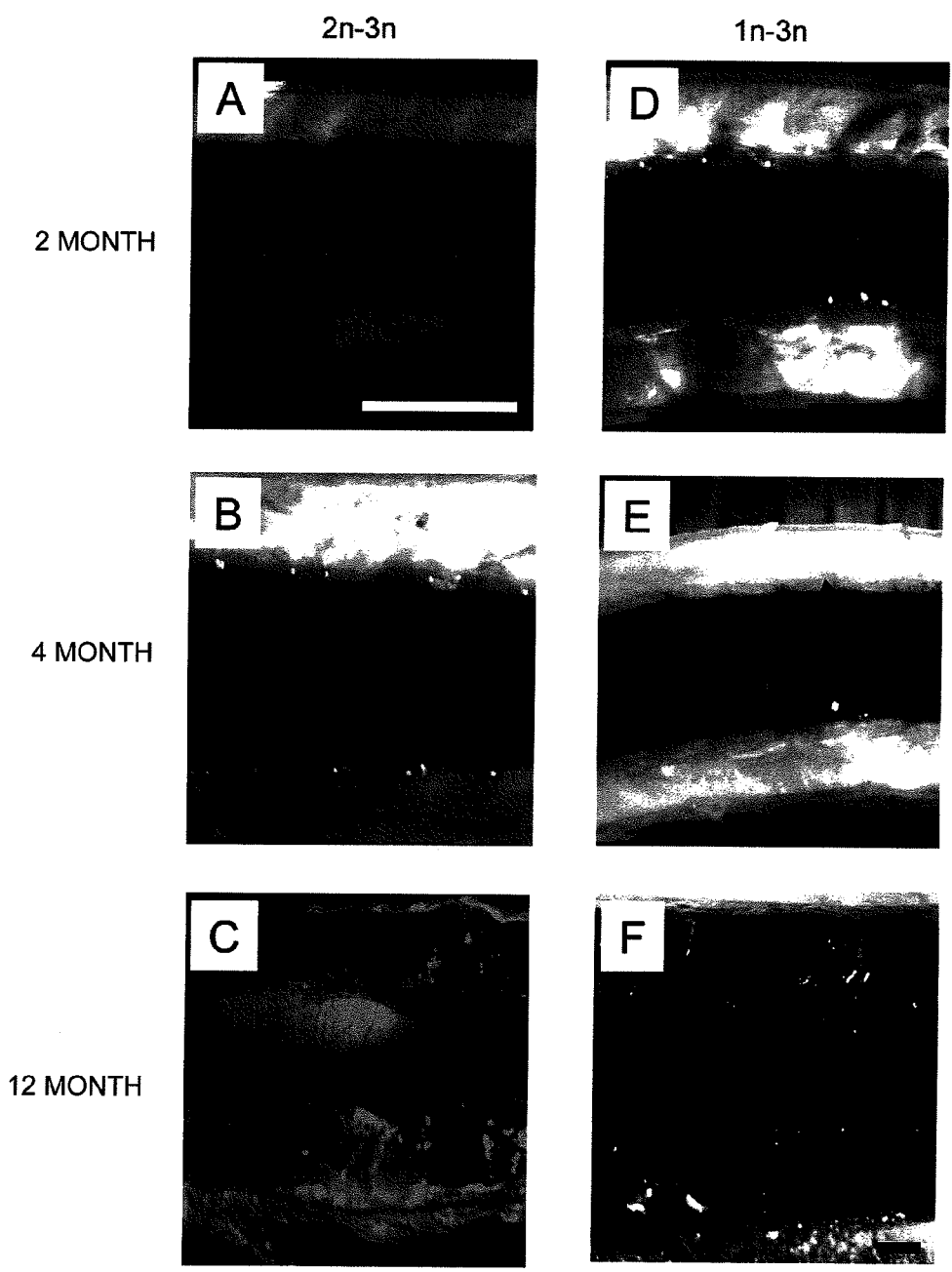
FIG. 2 is a series of photographs showing external morphologies of the gonad of haploid-triploid chimeric (hereinafter also referred to as "1n-3n") and 2n-3n chimeric loaches at 2, 4, and 12 months. (A, D) 2-month old, (B, E) 4-month old, (C, F) 12-month old, (A, B, C) 2n-3n chimera, and (D, E, F) 1n-3n chimera. The arrow heads indicate undifferentiated gonad (A, B, D, E) and testis (C, F), and the scale bar indicates 1 mm.
Figure 3:
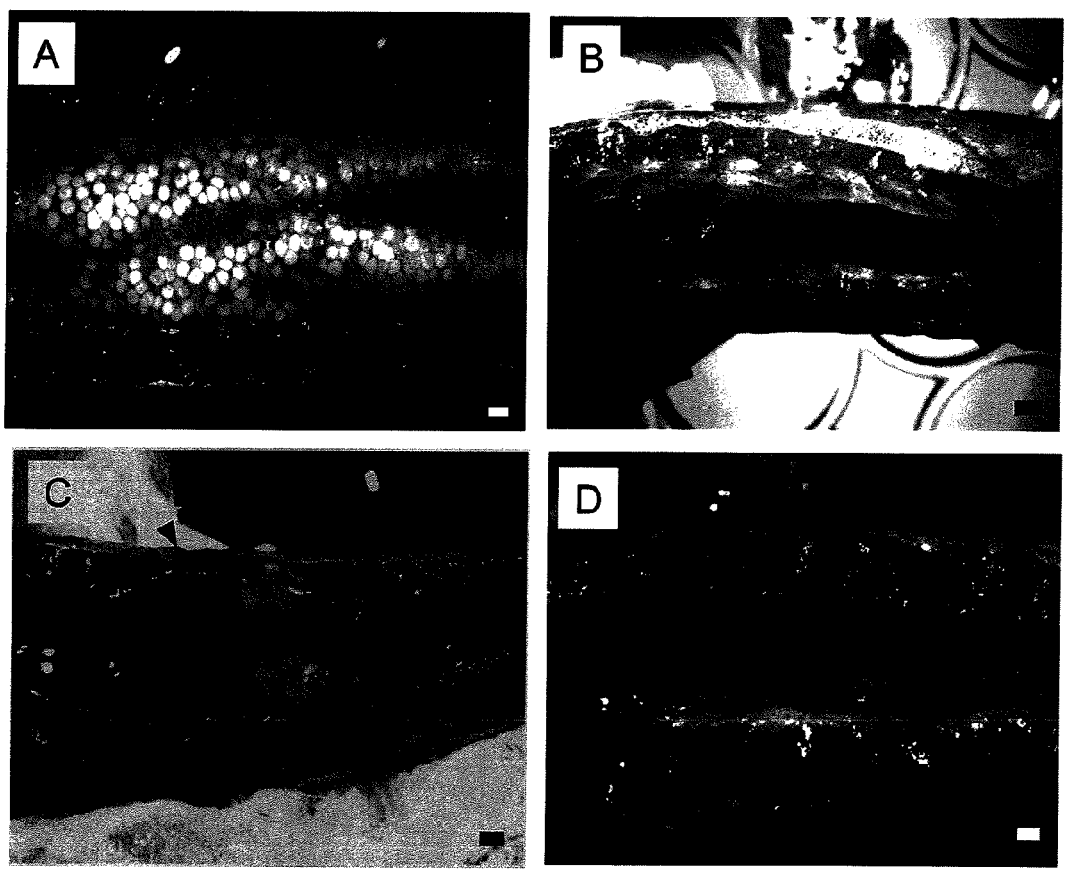
FIG. 3 is a series of photographs showing external morphologies of the ovary of normal diploid, triploid (derived from the crossing of a diploid female and a tetraploid male), 2n-3n chimeric, and 1n-3n chimeric adult loaches. (A) the normal diploid female adult fish; Table 8, No. 2, (B) the triploid derived from the crossing of diploid female and tetraploid male loaches; Table 8, No. 4, (C) the 2n-3n chimera; Table 8, 15.5-month old No. 5, and (D) the 1n-3n chimera; Table 8, 16-month old No. 3. The arrow heads indicate the ovary and the scale bar indicates 1 mm.

When the external morphology of the fixed gonad of a 2n-3n chimera was observed, a pair of thin gonads were seen in individuals 1- and 2-month old after hatching (FIG. 2A). In an individual 4-month old after hatching, a partially developed gonad could be observed (FIG. 2B). More largely developed gonads (testes) could be observed in 12-, 15.5-, and 16-month old males which had become adult fishes whose sex could become determined (FIG. 2C). A pair of thin gonads were seen in a 1n-3n chimera 1-, 2-, or 4-month old after hatching (FIGS. 2D and E), and a partially largely developed gonad was observed in the 12-month old one (FIG. 2F). In a 2n female adult fish, an ovary was seen which has many highly developed oocytes forming one layer along the kidney (FIG. 3A). The ovary of a 3n adult fish not sterilized by dndMO treatment was observed to spread in one layer along the kidney; however, the ovary did not contain no oocytes developed as in the 2n (FIG. 3B). In a 15.5-month old 2n-3n female adult fish, an ovary was observed which has a few oocytes developed as in the 2n (FIG. 3C). In 1n-3n, an ovary was seen which spreads in one layer along the kidney; however, no oocytes developed as in the 2n and the 2n-3n were observed in the ovary thereof (FIG. 3D).

2. Proliferation of Donor-Derived PGC

Figure 4:
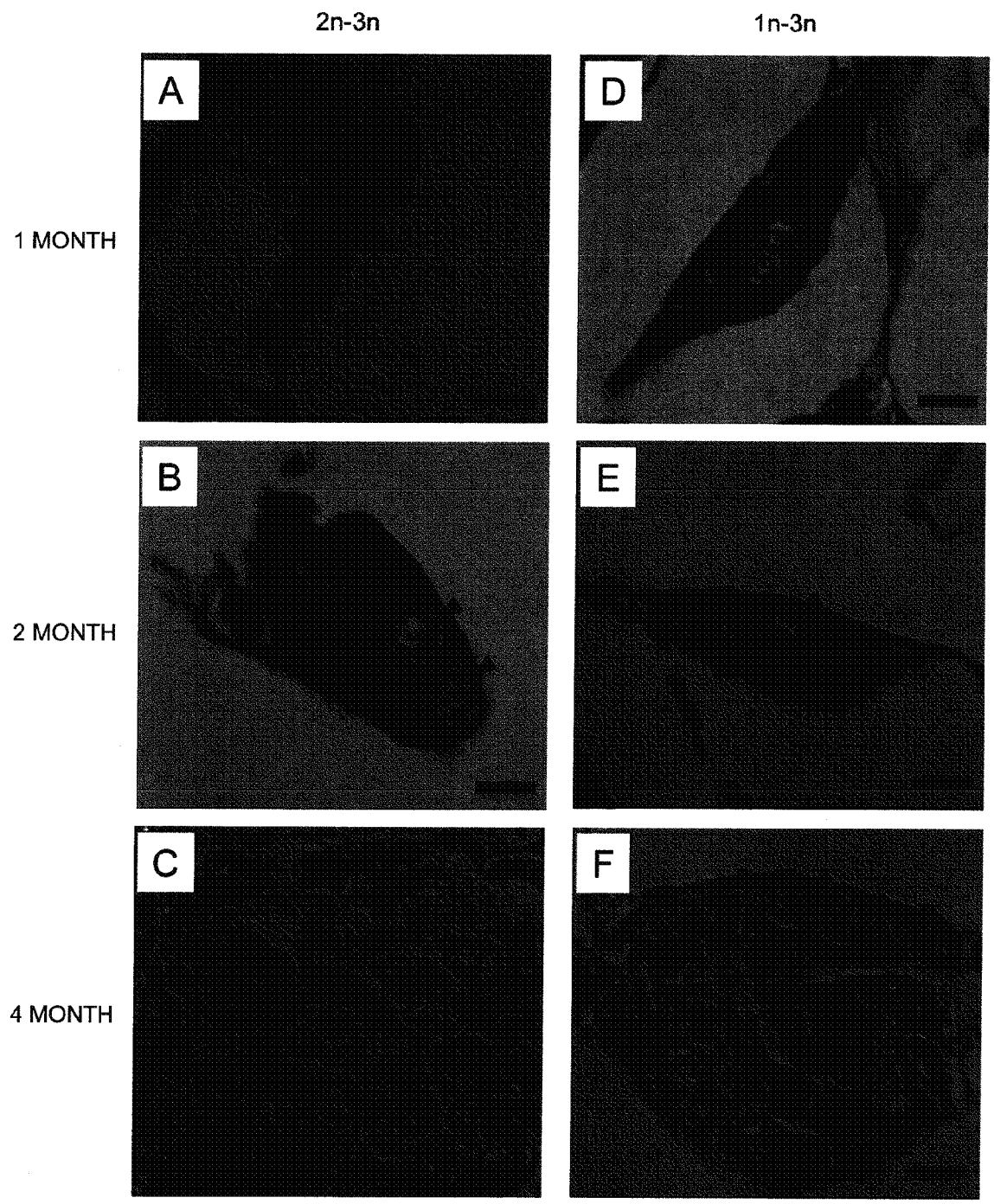
FIG. 4 is a series of photographs showing the process of proliferation of 2n-3n chimeric and 1n-3n chimeric undifferentiated germ cells of 1, 2, 4-month old loaches. (A, D) 1-month old, (B, D) 2-month old, (C, F) 4-month old, (A, B, C) a 2n-3n chimera, and (D, E, F) a 1n-3n chimera. The arrow heads indicate undifferentiated germ cells and the scale bar indicates 10 μm.
Figure 5:
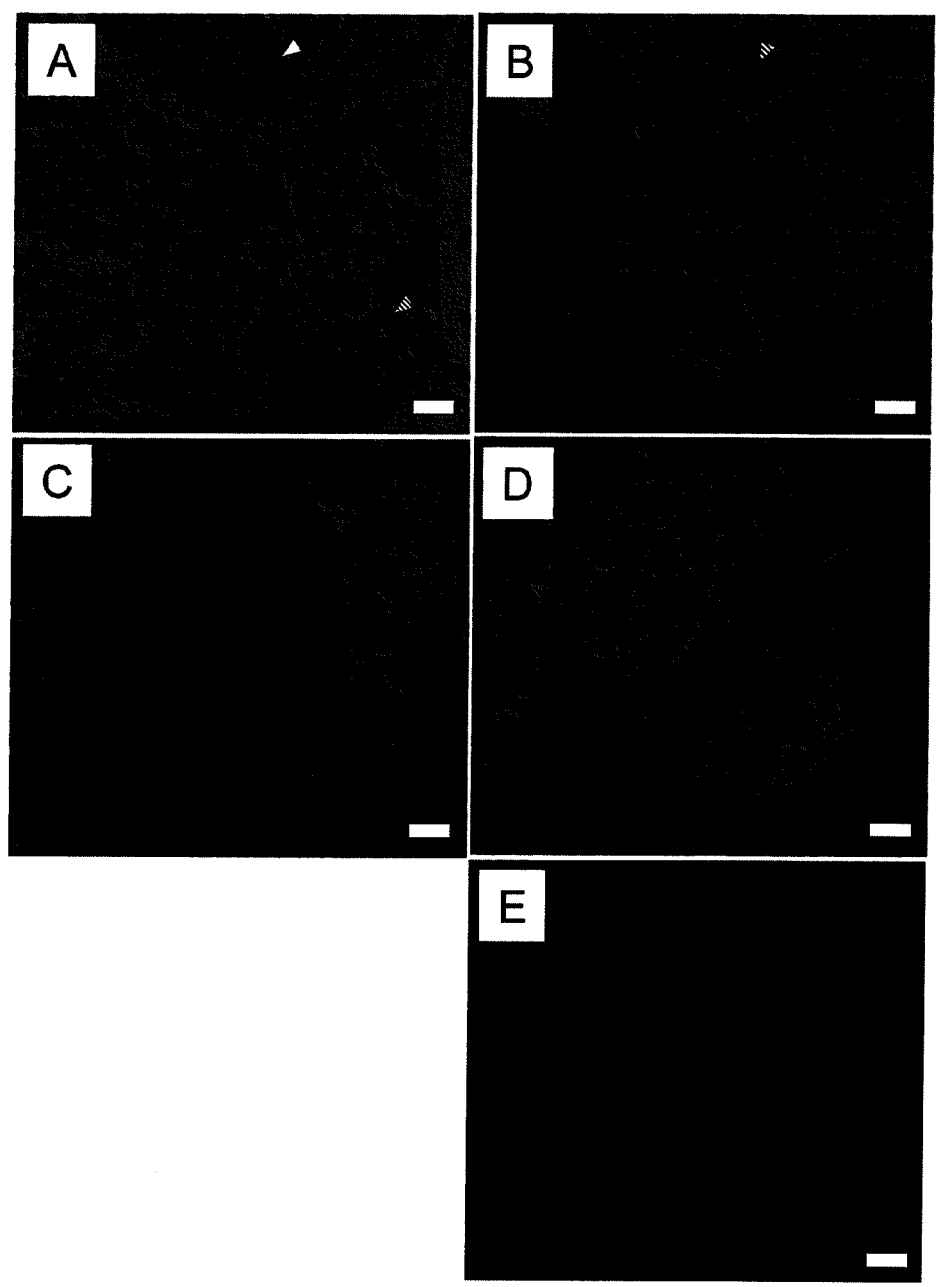
FIG. 5 is a series of photographs showing the structure of the testis of normal diploid, triploid (derived from the crossing of a diploid female and a tetraploid male), 2n-3n chimeric, and 1n-3n chimeric adult loaches. (A) the normal diploid, (B) the triploid derived from the crossing of a diploid female and a tetraploid male, (C) the 2n-3n chimera; Table 8, 16-month old No. 1, (D) the 1n-3n chimera in which spermatids and sperms were observed; Table 8, 15.5-month old No. 2, and (E) the 1n-3n chimera in which spermatids and sperms were not observed; Table 8, 15.5-month old No. 3. The black arrow head indicates A-type spermatogonial cells; the gray arrow head, B-type spermatogonial cells; the stripe arrow head, spermatocytes; the white arrow head, spermatids or sperms; and the scale bar, 10 μm.
Figure 6:
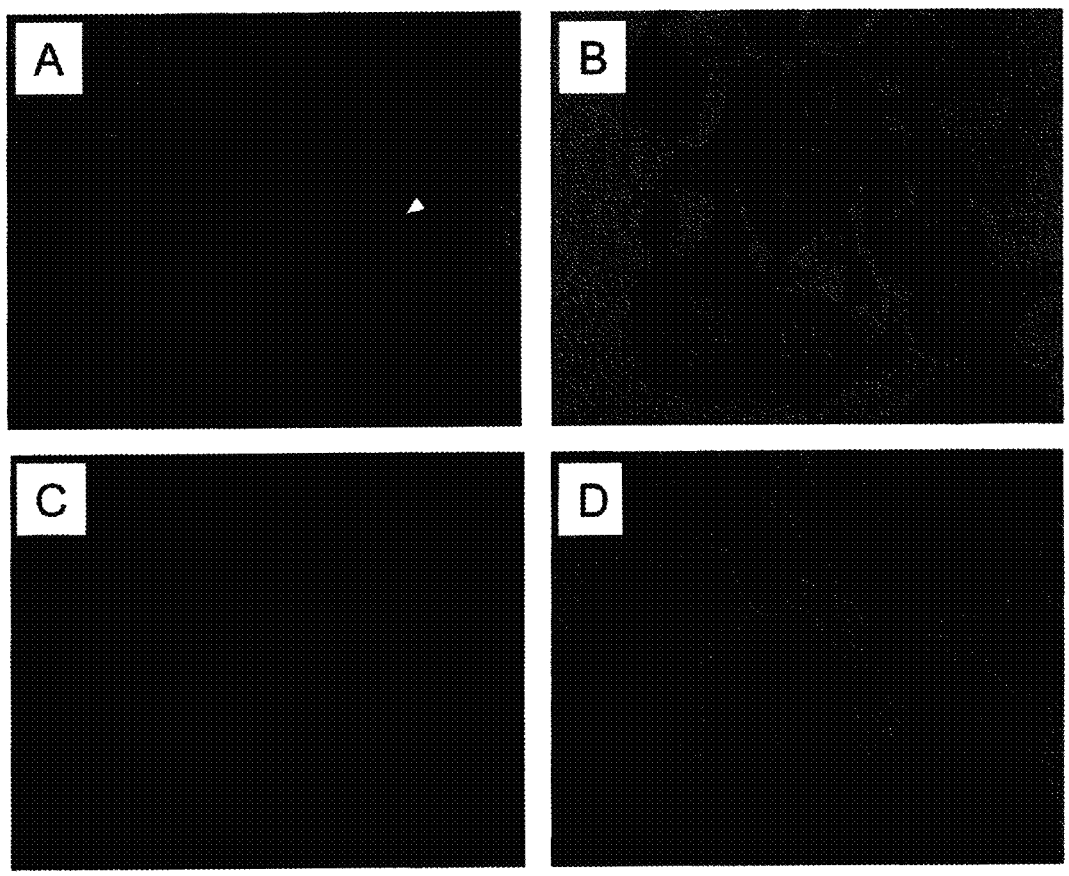
FIG. 6 is a series of photographs showing the structure of the ovary of normal diploid, triploid (derived from the crossing of a diploid female and a tetraploid male), 2n-3n chimeric, and 1n-3n chimeric adult loaches. (A) the normal diploid, (B) the triploid derived from the crossing of a diploid female and a tetraploid male, (C) the 2n-3n chimera; Table 8, 15.5-month old No. 5, and (D) the 1n-3n chimera; Table 8, 16-month old No. 3. The deep gray arrow head indicates an oocyte at the perinucleolus stage, the white arrow head, an oocyte at the yolk vesicle stage, and the scale bar, 10 μm.

In the 1n-3n and 2n-3n, donor PGCs observed in the genital ridge under a fluorescence microscope after chimera induction were counted, and the chimeras were grouped and bred depending on the number of PGCs (1, 2, 3, 4, 5, . . . ). From images of gonad tissues, the undifferentiated germ cells of 1- to 16-month old 1n-3n and 2n-3n individuals (for 12-month- or more old individuals, the A-type spermatogonial cells of males and the oogonia of females) were counted, and it was examined how many such undifferentiated germ cells was proliferated, maintained, and decreased relative to the number of PGCs (1, 2, 3, 4, 5, . . . ) counted in inducing the chimeras (Tables 5 and 6). As a result, 1-month old 2n-3n individuals showing the proliferation of undifferentiated germ cells were not found. However, six 2-month old individuals showing the proliferation were found (Table 5). Some individuals in which initial one PGC was proliferated to 40 or more were also found (Table 5 and FIG. 4B). In many 4-month-or more old chimeric individuals, the active proliferation of germ cells was identified (Table 5 and FIG. 4C). In the testis of the male 2n-3n fishes of 12, 15.5, and 16 months of age enabling the discrimination between sexes and the adult 2n fish, all of the sperm formation stages (spermatogonial cells, spermatocytes, many spermatids, and sperms) were observed (FIGS. 5A and C). In 3n adult fishes not treated with dndMO, germ cells larger than those in 2n were seen, and no spermatid or sperm was observed (FIG. 5B). In 1n-3n, 4 individuals in which proliferation from the initial number of PGCs was observed were seen for the 1-month old chimera. 1 to 4 PGCs were proliferated (Table 6, FIG. 4D). In 2-month old individuals, 2 to 10 or more PGCs were observed to proliferate (Table 6, FIG. 4E). In a fewer of 4-month-or-more old individuals compared to for 2n-3n, the active proliferation of germ cells was demonstrated (Table 6, FIG. 4F). For 12-, 15.5-, and 16-month old male adult fishes, many spermatogonial cells having different sizes and a few spermatocytes were observed in the testis of many individuals (FIG. 5E). However, for one in two 16-month old 1n-3n individuals, all of the sperm formation stages were observed and many spermatids and sperms were seen (FIG. 5D) like 2n-3n. For females, many oocytes at the perinucleolus stage and a few oocytes at the yolk vesicle stage were observed in the ovary of 2n adult fishes and 3n not treated with dndMO (FIGS. 6A and B). Many oocytes at the perinucleolus stage and a few oocytes at the yolk vesicle stage were observed in the ovary of one 15.5-month old 2n-3n individual (FIG. 6C). Similarly, many oocytes at the perinucleolus stage and a few oocytes at the yolk vesicle stage were observed in the ovary of 16-month old 1n-3n (FIG. 6D). The proportion of individuals in which all 1- to 16-month old 1n-3n and 2n-3n donor PGCs were proliferated, maintained, or decreased was calculated (Table 7). In 2n-3n, individuals in which the number of PGCs was proliferated, maintained, and decreased relative to that initially measured were 51%, 5%, and 5%, respectively based on the total, and individuals in which germ cells were completely absent were 39%. In 1n-3n, proliferation, maintenance, decrease, and absence were observed in 35%, 2%, 10%, and 53%, respectively. The proportion of individuals in which PGCs were proliferated was low in 1n-3n compared to that in 2n-3n, and the proportion of individuals in which germ cells were absent was high in 1n-3n.

TABLE 5

Increase or Decrease in Germ Cell of 2n-3n Chimera at Each Developmental Stage

| 2n-3n | Number of PGCs Identified in Genital Ridge | Number | Body Length | Number of Germ Cells | Increase or Decrease in Germ Cell |
|---|---|---|---|---|---|
| 1 Month | 1 | 1 | 10.68 | 0 | — |
|  |  | 2 | 9.78 | 0 | — |
|  |  | 3 | 10.92 | 0 | — |
|  | 2 | 1 | 11.4 | 0 | — |
|  |  | 2 | 11.13 | 2 | = |
|  |  | 3 | 12.05 | 0 | — |
|  | 3 | 1 | 18.2 | 3 | = |
|  |  | 2 | 20.14 | 1 | — |
|  | 4 | 1 | 14.39 | 0 | — |
|  |  | 2 | 15.24 | 0 | — |

TABLE 5-continued

Increase or Decrease in Germ Cell of 2n-3n Chimera at Each Developmental Stage

| 2n-3n | Number of PGCs Identified in Genital Ridge | Number | Body Length | Number of Germ Cells | Increase or Decrease in Germ Cell |
|---|---|---|---|---|---|
| 2 Months | 1 | 1 | 18.71 | 2 | + |
|  |  | 2 | 19.08 | 0 | − |
|  |  | 3 | 19.34 | 0 | − |
|  |  | 4 | 21.07 | 2 | + |
|  |  | 5 | 17.09 | 40 or more | ++ |
|  | 2 | 1 | 21.62 | 0 | − |
|  |  | 2 | 23.67 | 5 | + |
|  |  | 3 | 21.68 | 7 | + |
|  | 4 | 1 | 30.19 | 2 | − |
|  |  | 2 | 27.81 | 6 | + |
| 4 Months | 1 | 1 | 47.80 | 0 | − |
|  |  | 2 | 46.65 | Many | ++ |
|  | 2 | 1 | 47.14 | Many | ++ |
|  |  | 2 | 47.24 | 0 | − |
|  |  | 3 | 47.71 | 0 | − |
|  |  | 4 | 44.75 | Many | ++ |
|  | 4 | 1 | 51.54 | Many | ++ |
|  |  | 2 | 53.55 | Many | ++ |
|  |  | 3 | 50.69 | Many | ++ |
|  |  | 4 | 49.33 | Many | ++ |
| 12 Months | 1 | 1 | 76.91 | 0 | − |
|  |  | 2 | 79.87 | Many | ++ |
|  |  | 3 | 64.47 | 0 | − |
|  | 2 | 1 | 74.37 | Many | ++ |
|  |  | 2 | 74.22 | Many | ++ |
|  |  | 3 | 69.24 | Many | ++ |
| 15.5 Months | 1 | 1 | 71.68 | 0 | − |
|  |  | 2 | 68.78 | Many | ++ |
|  |  | 1 | 70.11 | Many | ++ |
|  |  | 2 | 73.29 | Many | ++ |
|  |  | 3 | 84.69 | Many | ++ |
| 16 Months | 2 | 1 | 86.28 | Many | ++ |
|  |  | 2 | 90.62 | 0 | − |

Proliferated (+),
Markedly Proliferated (++)
Maintained (=),
Decreased (−)

TABLE 6

Increase or Decrease in Germ Cell of 1n-3n Chimera at Each Developmental Stage

| 1n-3n | Number of PGCs Identified in Genital Ridge | Number | Body Length | Number of Germ Cells | Increase or Decrease in Germ Cell |
|---|---|---|---|---|---|
| 1 Month | 1 | 1 | 12.46 | 2 | + |
|  |  | 2 | 11.93 | 0 | − |
|  |  | 3 | 13.23 | 1 | = |
|  |  | 4 | 13.24 | 5 | + |
|  | 2 | 1 | 12.89 | 0 | − |
|  |  | 2 | 12.08 | 4 | + |
|  |  | 3 | 11.83 | 1 | − |
|  | 4 | 1 | 17.54 | 2 | − |
|  |  | 2 | 18.12 | 1 | − |
|  | 5 | 1 | 20.48 | 8 | + |
| 2 Months | 1 | 1 | 21.42 | 3 | + |
|  |  | 2 | 20.78 | 0 | − |
|  |  | 3 | 21.33 | 0 | − |
|  | 2 | 1 | 23.18 | 10 or more | + |
|  |  | 2 | 23.06 | 0 | − |
|  |  | 3 | 23.78 | 0 | − |
|  | 3 | 1 | 33.03 | 0 | − |
|  |  | 2 | 27.9 | 1 | − |
|  | 5- | 1 | 26.71 | 1 | − |
|  |  | 2 | 30.2 | 0 | − |

TABLE 6-continued

Increase or Decrease in Germ Cell of 1n-3n Chimera at Each Developmental Stage

| 1n-3n | Number of PGCs Identified in Genital Ridge | Number | Body Length | Number of Germ Cells | Increase or Decrease in Germ Cell |
|---|---|---|---|---|---|
| 4 Months | 1 | 1 | 54.44 | 0 | − |
|  |  | 2 | 60.10 | 0 | − |
|  | 2 | 1 | 58.90 | Many | ++ |
|  |  | 2 | 57.73 | Many | ++ |
|  | 3 | 1 | 65.21 | 0 | − |
|  |  | 2 | 61.06 | 0 | − |
|  | 4 | 1 | 57.00 | Many | ++ |
|  |  | 2 | 54.84 | 0 | − |
|  |  | 3 | 49.19 | 0 | − |
|  |  | 4 | 46.31 | Many | + |
| 12 Months | 1 | 1 | 71.38 | 0 | − |
|  |  | 2 | 75.07 | 0 | − |
|  | 2 | 1 | 80.27 | 0 | − |
|  |  | 2 | 89.33 | 0 | − |
|  |  | 3 | 97.31 | Many | ++ |
|  | 3 | 1 | 75.51 | Many | ++ |
| 15.5 Months | 1 | 1 | 72.77 | 0 | − |
|  |  | 2 | 75.99 | Many | ++ |
|  |  | 1 | 74.61 | Many | ++ |
|  |  | 2 | 69.90 | 0 | − |
|  |  | 3 | 82.73 | 0 | − |
| 16 Months | 2 | 1 | 91.35 | 0 | − |
|  |  | 2 | 95.81 | 0 | − |
|  |  | 3 | 102.90 | Many | ++ |
|  |  | 1 | 87.27 | Many | ++ |
|  |  | 2 | 71.15 | 0 | − |
|  |  | 3 | 99.41 | 0 | − |
|  | 1 | 1 | 87.31 | 0 | − |
|  | 2 or 3 | 1 | 89.87 | Many | ++ |
|  |  | 2 | 91.79 | Many | ++ |
|  | 3 | 3 | 67.87 | 0 | − |

Proliferated (+),
Markedly Proliferated (++),
Maintained (=),
Decreased (−)

Figure 10:
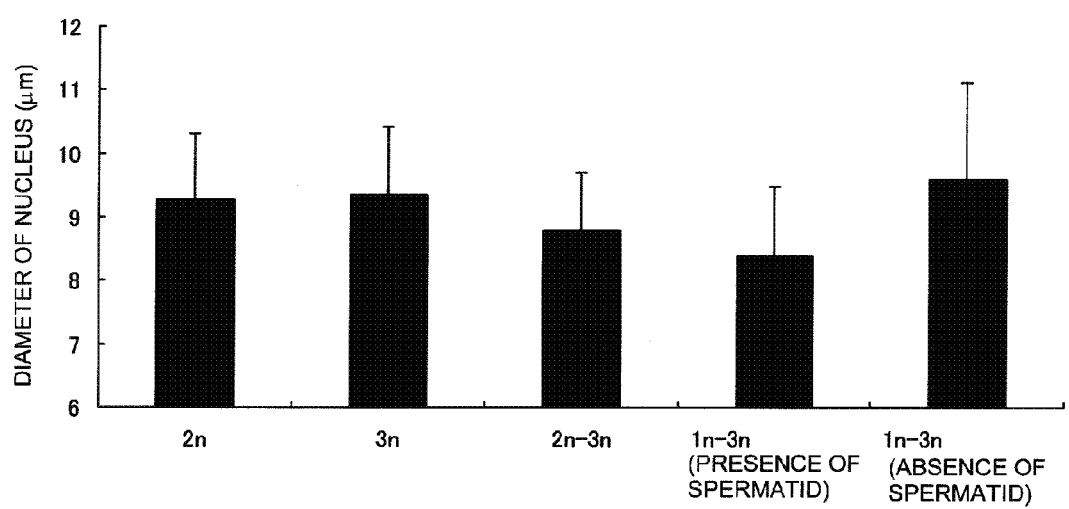
FIG. 10 is a graph showing the average size of A-type spermatogonial cell nuclei in normal diploid, triploid (derived from the crossing of a diploid female and a tetraploid male), 2n-3n chimeric, and 1n-3n chimeric adult loaches. The error bar indicates a standard deviation.

3. Diameter of Nucleus of Undifferentiated Germ Cell, a-Type Spermatogonial Cell, and Oogonium The diameter of the nucleus of undifferentiated germ cells of 1-month old 2n-3n was frequently 8 to 9 μm and had an average value of 9.2 μm (FIG. 7A). In 2-month old individuals, it was frequently 10 to 12 μm and had a minimum value of 7 μm, a maximum value of 14 μm, and an average value of 10.2 μm (FIG. 7B). The diameter of the nucleus of 1-month old 1n-3n was frequently 9 to 10 μm and had a minimum value of 5 μm, a maximum value of 10 μm, and an average value of 7.7 μm (FIG. 7C). In 2-month old individuals, it was frequently 7 to 9 μm and had a minimum value of 5 μm, a maximum value of 9 μm, and an average value of 6.8 μm (FIG. 7D). 1n-3n had smaller size undifferentiated germ cells than those of 2n-3n at 1 and 2 months of age, and had a significantly smaller nuclear diameter than that of 2n-3n at 2 months of age (Student's t-test, P<0.01) (FIG. 8). The diameter of the nucleus of 2n and 3n male adult fishes was frequently 9 to 10 μm and had a similar distribution therebetween. In 2n, it had a minimum value of 7 μm, a maximum value of 13 μm, and an average value of 9.3 μm, and in 3n, had a minimum value of 8 μm, a maximum value of 13 μm, and an average value of 9.4 μm; no significant difference was observed between the diameter of the nucleus of 2n and 3n (FIGS. 9A and B). In 2n-3n male adult fishes (12- to 16-month old), the diameter of the nucleus of A-type spermatogonial cells was frequently 9 to 10 μm and had a minimum value of 7 μm, a maximum value of 11 μm, and an average value of 8.8 μm (FIGS. 9C and 10). The diameter of the nucleus of 1n-3n male adult fishes in which spermatids and sperms were observed was frequently 9 to 10 μm and had a minimum value of 6 μm and a maximum value of 14 μm (FIG. 9D). The diameter of the nucleus of 1n-3n male adult fishes in which spermatids and sperms were not observed was frequently 9 to 10 μm and had a minimum value of 6 μm and a maximum value of 15 μm (FIG. 9E). 1n-3n male adult fish individuals in the tissue image of which the normal sperm formation stage was contained and spermatids and sperms were observed had an average nuclear diameter of 8.4 μm, and individuals having many spermatogonial cells and a few spermatocytes and having no spermatids or sperms observed had an average nuclear diameter of 9.6 μm (FIG. 10). No significant difference was observed between 2n, 3n, 2n-3n, and 1n-3n (Kruskal-Wallis test, P<0.05). The above results showed that many A-type spermatogonial cells in the testis of 1n-3n male adult fishes (12-, 15.5-, and 16-month old) had a nuclear diameter similar to that in 2n, 3n not treated with dndMO, and 2n-3n, but cells having large nuclei were present only in 1n-3n (FIGS. 9D and E).

Figure 11:
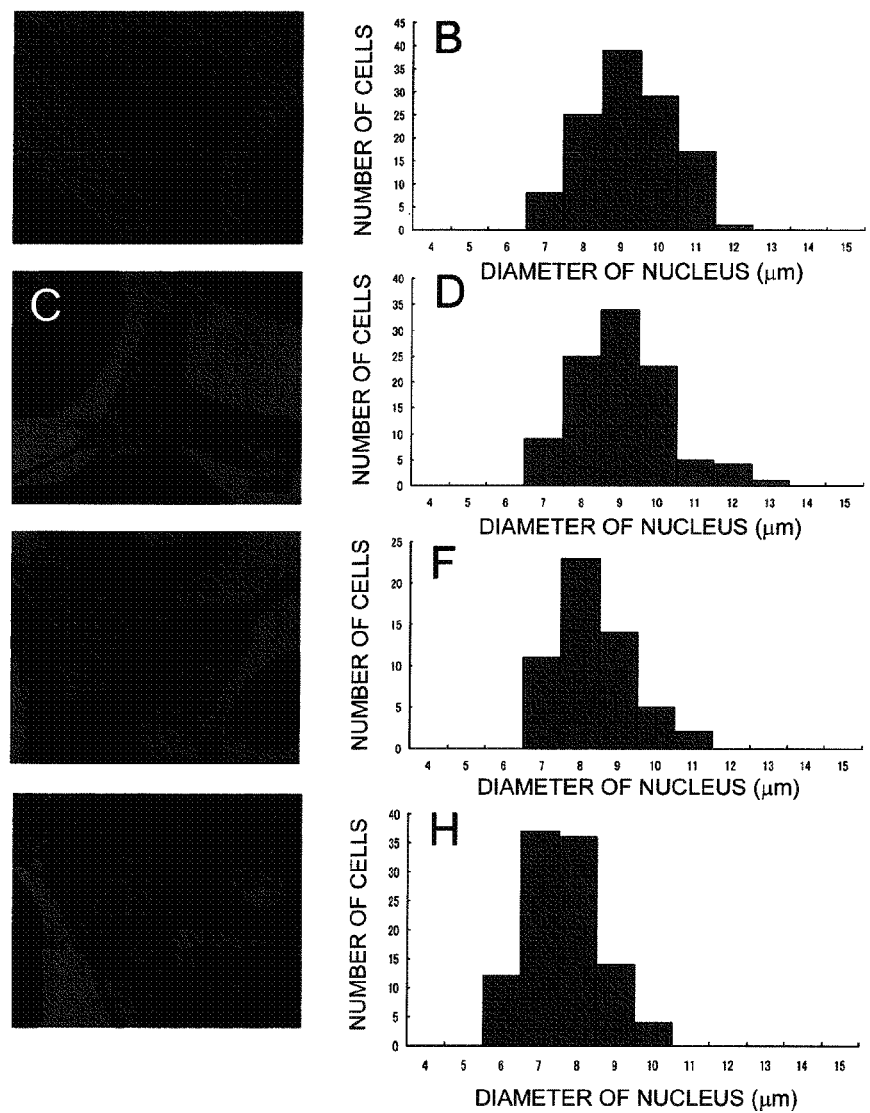
FIG. 11 is a series of photographs and graphs showing the hematoxylin-eosin stained images of oogonia and the frequency of the diameter of oogonium nuclei in normal diploid, triploid (derived from the crossing of a diploid female and a tetraploid male), 2n-3n chimeric, and 1n-3n chimeric adult loaches. (A, B) a normal diploid, (C, D) a triploid derived from the crossing of a diploid female and a tetraploid male, (E, F) a 2n-3n chimera; Table 8, 15.5-month old Nos. 3 and 5, and (G, H) a 1n-3n chimera; Table 8, 16-month old No. 3. The black arrow head indicates an oogonium, and the scale bar indicates 10 µm.
Figure 12:
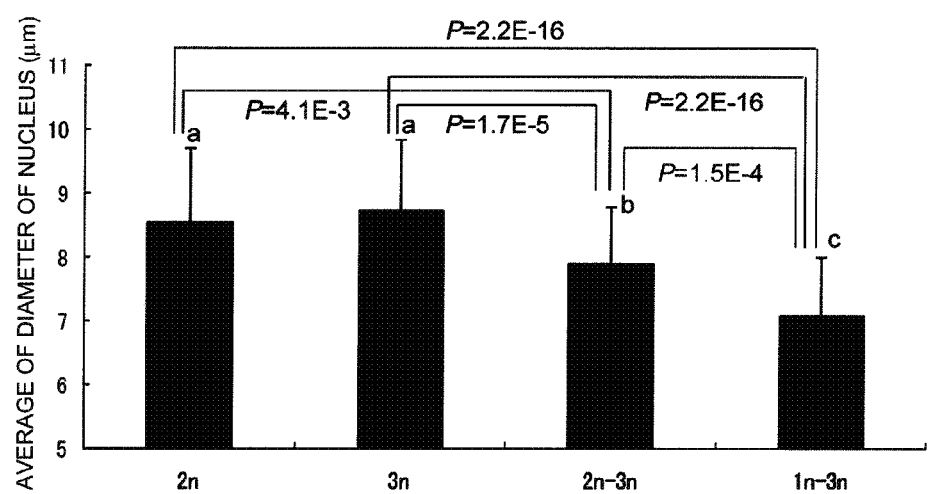
FIG. 12 is a graph showing the average size of oogonia nuclei in normal diploid, triploid (derived from the crossing of a diploid female and a tetraploid male), 2n-3n chimeric, and 1n-3n chimeric adult loaches. The error bar indicates a standard deviation. Significant differences were observed between the different alphabets (Kruskal-Wallis test, Scheffe method, $P<0.01$).

The frequency of the diameter of the nucleus of oogonia of 15.5- and 16-month old 1n-3n and 2n-3n were measured. The nuclear diameter in 2n, 3n not sterilized by dndMO treatment, and 2n-3n was frequently 8 to 9 μm and had a maximum value of 13 μm and a minimum value of 7 μm (FIGS. 11B, D, and F). The average value was 8.5 μm for 2n, 8.7 μm for 3n, and 7.9 μm for 2n-3n (FIG. 12). The nuclear diameter of such cells of 1n-3n was frequently 7 to 8 μm and had a minimum value of 6 μm, a maximum value of 10 μm, and an average value of 7.1 μm (FIGS. 11H and 12). A significant difference in the diameter of the nucleus of oogonia was observed in 1n-3n when compared to that in 2n, 3n not treated with dndMO, or 2n-3n (FIG. 12, Kruskal-Wallis test, Scheffe method, P<0.05). Thus, 1n-3n female adult fishes were shown to have small oogonia compared to 2n, 3n not treated with dndMO, or 2n-3n.

4. Ploidy of Gonad

Figure 13:
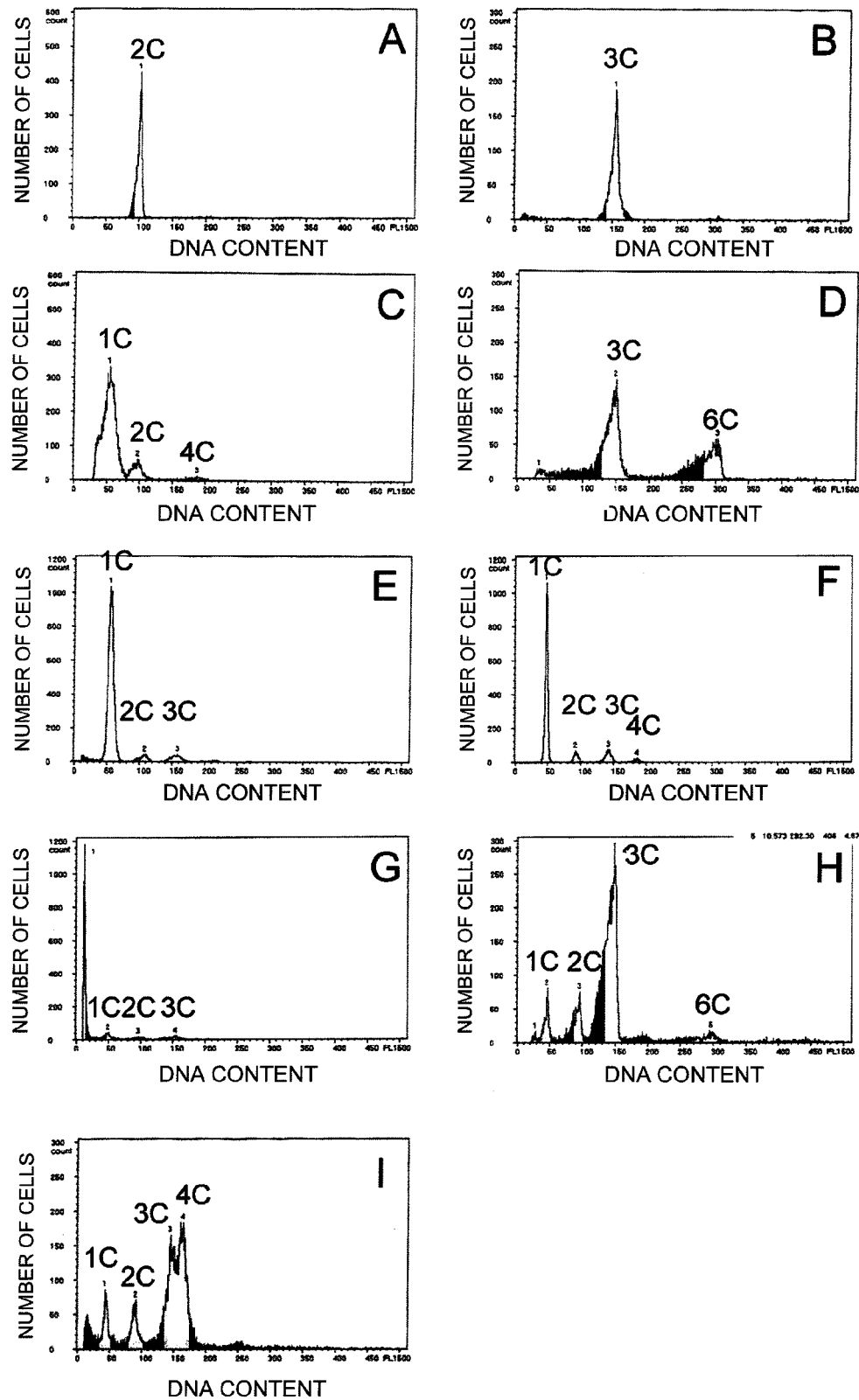
FIG. 13 is a series of graphs showing the polyploidy of the somatic cells (fin) and the cells making up the testis of normal diploid, triploid (derived from the crossing of a diploid female and a tetraploid male), 2n-3n chimeric, and 1n-3n chimeric adult loaches. (A) the somatic cells of the normal diploid; Table 8, No. 1, (B) the somatic cells of the triploid; Table 8, No. 1, (C) the testis of the normal diploid; Table 8, No. 1, (D) the testis of the triploid; Table 8, No. 1, (E) the testis of the 2n-3n chimera; Table 8, 15.5-month old No. 4, (F) the testis of the 2n-3n chimera; Table 8, 12-month old No. 4, (G) the testis of the 1n-3n chimera; Table 8, 16-month old No. 4, (H) the testis of the 1n-3n chimera; Table 8, 16-month old No. 9, and (I) the testis of the 1n-3n chimera; Table 8, 15.5-month old No. 3. The C value in the figure indicates the relative DNA content when the DNA content of the somatic cell of the normal diploid loach is set to 2C.

The fin of normal male adult fishes was composed of 2n cell population (FIG. 13A). However, cell populations having ploidies corresponding to 1n, 2n, and 4n were seen in the testis, and 1n cells were dominant (FIG. 13C). The fin of 3n male adult fishes (not sterilized by dndMO treatment) was composed of 3n cell population (FIG. 13B), and the testis thereof was composed of 3n and 6n cells (FIG. 13D). The fin of 2n-3n male adult fishes (12- to 16-month old) had only 3n cells, and 2n cells were not seen (Table 7). The 2n-3n developed testis was composed of 1n and 3n (Table 7), 1n, 2n, and 3n (FIG. 13E), or 1n, 2n, 3n, and 4n (FIG. 13F) cell populations. In the testis of these individuals, a high peak of 1n cell population and other small peaks of 2n and 3n were observed. The fin of 1n-3n male adult fishes (12- to 16-month old) had only 3n cells (Table 8), and 1n cells were not observed. In contrast, the testis of 1n-3n individuals having the developed testis was composed of cell populations having different ploidies of 1n, 2n, and 3n (FIG. 13G), 1n, 2n, 3n, and 6n (FIG. 13H), or 1n, 2n, 3n, and 4n (FIG. 13I). In these individuals, the 1n and 2n cell populations had comparable sizes, and cell populations having 4n cells and 3n somatic cells in the host gonad and their cells with 6n ploidy at the G2/M phase were detected. Individuals in the testis of which only a peak for 3n was detected probably are considered to have only somatic cells of the gonad of triploid hosts. The testis of 2n-3n and 1n-3n undeveloped testis was composed of 3n cell population considered host's somatic cells (Table 8).

TABLE 7

Summary of Average Body Length, Average Total Length, and Increase or Decrease in Germ Cell of Chimera (2n-3n and 1n-3n) at Each Developmental Stage

| Chimera | After Hatching | Number of Individuals | Average Body Length (mm) | Proliferated (%) | Germ Cell Maintained (%) | Decreased (%) | No Germ Cell (%) |
|---|---|---|---|---|---|---|---|
| 2n-3n | 1 Month | 10 | 13.4 | 0 | 2 | 1 | 7 |
| | 2 Months | 10 | 22.0 | 6 | 0 | 1 | 3 |
| | 4 Months | 10 | 48.6 | 7 | 0 | 0 | 3 |
| | 12 Months | 6 | 73.2 | 4 | 0 | 0 | 2 |
| | 15.5 Months | 5 | 73.7 | 4 | 0 | 0 | 1 |
| | 16 Months | 2 | 88.5 | 1 | 0 | 0 | 1 |
| | Total | 43 | — | 22 (51) | 2 (5) | 2 (5) | 17 (39) |
| n-3n | 1 Month | 10 | 14.4 | 4 | 1 | 3 | 2 |
| | 2 Months | 10 | 25.1 | 2 | 0 | 2 | 6 |
| | 4 Months | 10 | 56.5 | 4 | 0 | 0 | 6 |
| | 12 Months | 6 | 81.5 | 2 | 0 | 0 | 4 |
| | 15.5 Months | 5 | 75.2 | 2 | 0 | 0 | 3 |
| | 16 Months | 6 | 91.3 | 4 | 0 | 0 | 6 |
| | Total | 51 | — | 18 (35) | 1 (2) | 5 (10) | 27 (53) |

Figure 14:
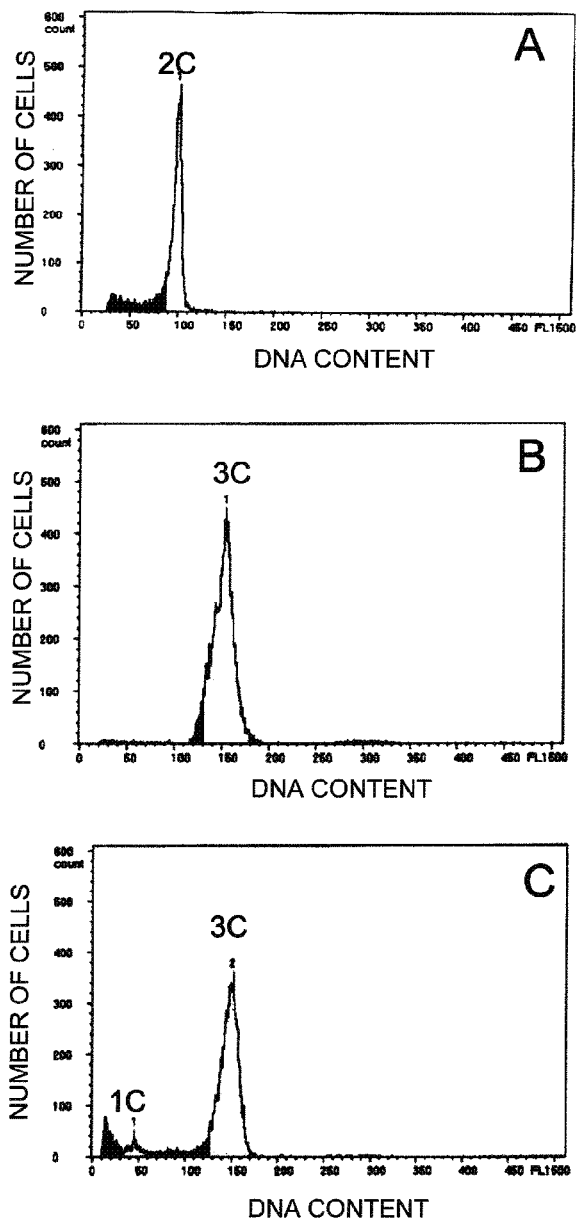
FIG. 14 is a series of graphs showing the polyploidy of the cells making up the ovary of normal diploid, triploid (derived from the crossing of a diploid female and a tetraploid male), and 1n-3n chimeric adult loaches. (A) the normal diploid; Table 8, No. 2, (B) the triploid; Table 8, No. 5, and (C) the 1n-3n chimera; Table 8, 16-month old No. 3. The C value in the figure indicates the relative DNA content when the DNA content of the somatic cell of the normal diploid loach is set to 2C.

The fin of normal female fishes was composed of 2n cell population. The ovary was composed almost of 2n cells (FIG. 14A). The fin of 3n adult fishes not sterilized by dndMO treatment was composed of 3n cells, and the ovary thereof, of 3n cells (FIG. 14B). The fin of 15.5-month old 2n-3n individuals having the developed ovary was composed of 3n cells; the ovary of one of 2 individuals was composed of 3n cells and the ploidy was not detected in the remaining one individual (Table 8). 1n and 3n cells were observed in the developed ovary of a 16-month 1n-3n individual (FIG. 14C). In the ovary of this individual, a low peak for 1n cell population and a high peak for triploid host-derived 3n somatic cells were observed. The ovary of 1n-3n individuals having an undeveloped ovary was composed of host-derived 3n somatic cells (Table 8).

TABLE 8

Ploidy of Gonad of Chimeric Male Adult Fish

| After Hatching | Individual Number | Sex | Body Length | Presence (+) or Absence (−) of Developed Gonad | Ploidy | | |
|---|---|---|---|---|---|---|---|
| | | | | | Fin | Gonad | Sperm |
| 2n | Adult Fish | No. 1 | ♂ | 112.44 | + | 2n | 1n, 2n, 4n | — |
| | | No. 2 | ♀ | 141.11 | + | 2n | 2n | — |
| | | No. 3 | ♀ | 135.38 | + | 2n | 2n | — |

TABLE 8-continued

Ploidy of Gonad of Chimeric Male Adult Fish

| After Hatching | Individual | Number | Sex | Body Length | Presence (+) or Absence (−) of Developed Gonad | Ploidy Fin | Ploidy Gonad | Sperm |
|---|---|---|---|---|---|---|---|---|
| 3n | Adult Fish | No. 1 | ♂ | 87.76 | + | 3n | 3n, 6n | — |
| | | No. 2 | ♂ | 75.99 | + | 3n | 3n, 6n | — |
| | | No. 3 | ♂ | 103.12 | + | 3n | 3n, 6n | — |
| | | No. 4 | ♀ | 90.74 | + | 3n | 3n | — |
| | | No. 5 | ♀ | 97.04 | + | 3n | 3n | — |
| 2n-3n | 12 Months | No. 1 | ♂ | 76.91 | − | 3n | 3n | — |
| | | No. 2 | ♂ | 79.87 | + | 3n | 1n, 2n, 3n | 1n |
| | | No. 3 | ♂ | 64.47 | − | 3n | 3n | — |
| | | No. 4 | ♂ | 74.37 | + | 3n | 1n, 2n, 3n, 4n | 1n |
| | | No. 5 | ♂ | 74.22 | + | 3n | 1n, 3n | 1n |
| | | No. 6 | ♂ | 69.24 | + | 3n | 1n, 2n, 3n, 4n | 1n |
| | 15.5 Months | No. 1 | ♂ | 71.68 | − | 3n | 3n | — |
| | | No. 2 | ♂ | 68.78 | + | 3n | Not Detectable | — |
| | | No. 3 | ♀ | 70.11 | + | 3n | 3n | — |
| | | No. 4 | ♂ | 73.29 | + | 3n | 1n, 2n, 3n | — |
| | | No. 5 | ♀ | 84.69 | + | 3n | Not Detectable | — |
| | 16 Months | No. 1 | ♂ | 86.28 | + | 3n | 1n, 2n, 3n | — |
| | | No. 2 | ♂ | 90.62 | − | 3n | 3n | — |
| 1n-3n | 12 Months | No. 1 | ♂ | 71.38 | − | 3n | 3n | — |
| | | No. 2 | ♂ | 75.07 | − | 3n | 3n | — |
| | | No. 3 | ♂ | 80.27 | − | 3n | 3n | — |
| | | No. 4 | ♂ | 89.33 | − | 3n | 3n | — |
| | | No. 5 | ♂ | 97.31 | + | 3n | Not Detectable | 1n |
| | | No. 6 | ♂ | 75.51 | + | 3n | 1n, 2n, 3n, 4n | 1n |
| | 15.5 Months | No. 1 | ♂ | 72.77 | − | 3n | 3n | — |
| | | No. 2 | ♂ | 75.99 | + | 3n | 3n | — |
| | | No. 3 | ♂ | 74.61 | + | 3n | 1n, 2n, 3n, 4n | — |
| | | No. 4 | ♂ | 69.90 | − | 3n | 3n | — |
| | | No. 5 | ♂ | 82.73 | − | 3n | 3n | — |
| | 16 Months | No. 1 | ♂ | 91.35 | − | 3n | 3n | — |
| | | No. 2 | ♀ | 95.81 | − | 3n | 3n | — |
| | | No. 3 | ♀ | 102.90 | + | 3n | 1n, 3n | — |
| | | No. 4 | ♂ | 87.27 | + | 3n | 1n, 2n, 3n | — |
| | | No. 5 | ♀ | 71.15 | − | 3n | 3n | — |
| | | No. 6 | ♂ | 99.41 | − | 3n | 3n | — |
| | | No. 7 | ♂ | 87.31 | − | 3n | 3n | — |
| | | No. 8 | ♂ | 89.87 | + | 3n | 1n, 2n, 3n | — |
| | | No. 9 | ♂ | 91.79 | + | 3n | 1n, 2n, 3n, 6n | — |
| | | No. 10 | ♂ | 67.87 | − | 3n | 3n | — |

Individuals 12-month old after hatching were injected with hGC to collect sperms.

5. Morphology and Ploidy of Sperm in 1n-3n

Figure 15:
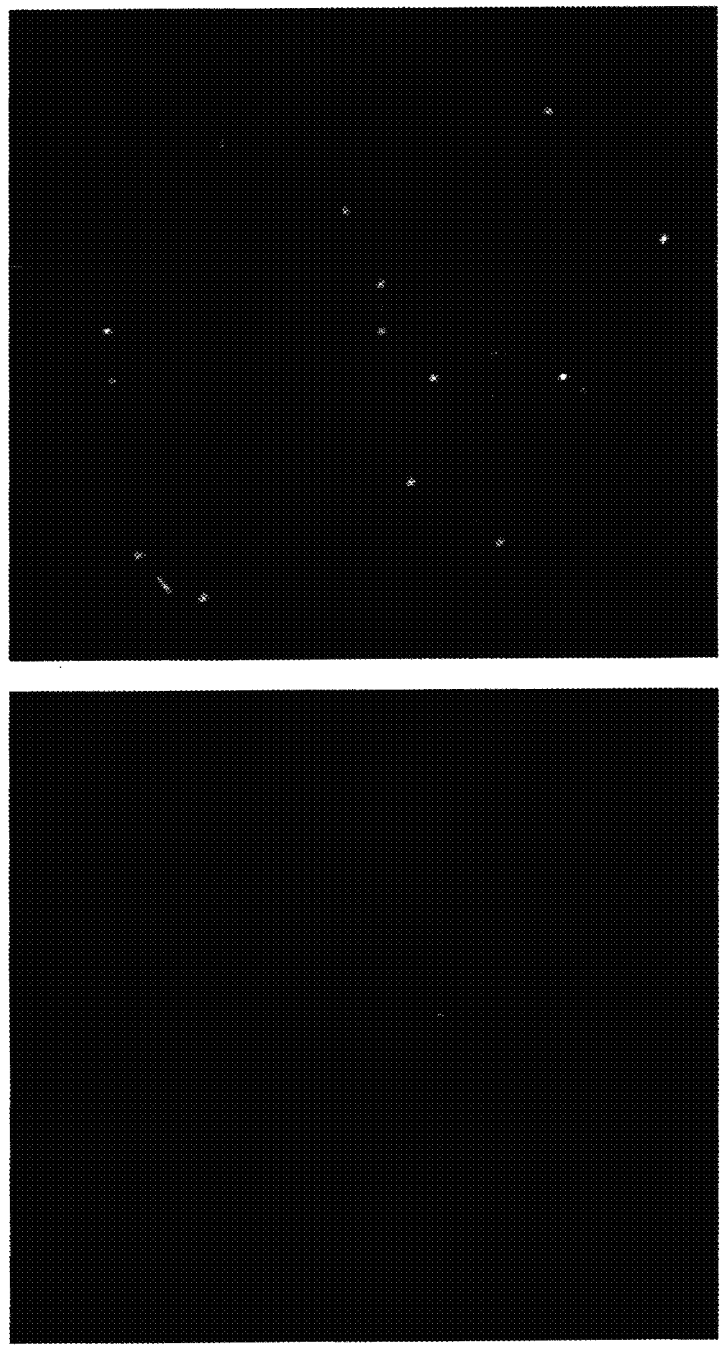
FIG. 15 is a pair of photographs showing morphologies observed under a light microscope, of sperms collected from 12-month old 2n-3n chimeric and 1n-3n chimeric loaches. (A) the sperm of the 2n-3n chimera, (B) the sperm of the 1n-3n chimera. The arrow head indicates a sperm, and the scale bar indicates 10 µm.
Figure 16:
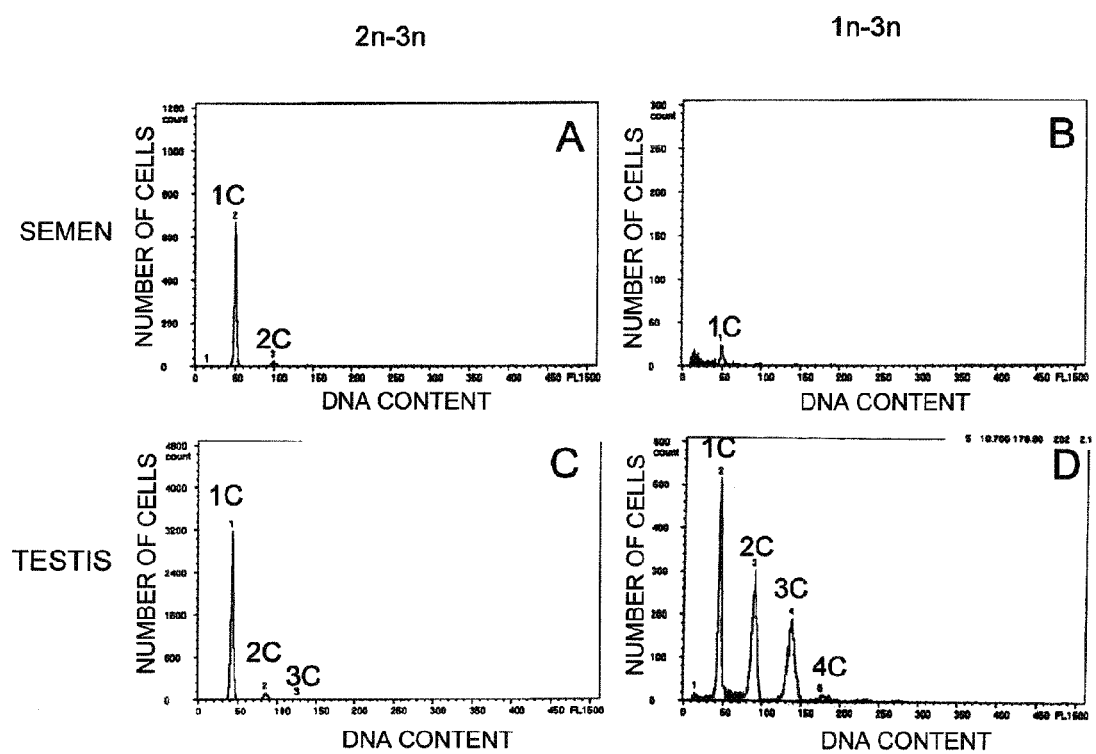
FIG. 16 is a series of graphs showing the polyploidy of the cells making up the semen and the testis of 12-month old 2n-3n chimeric and 1n-3n chimeric loaches. (A) the semen of the 2n-3n chimera; Table 8, 12-month old No. 2, (B) the semen of the 1n-3n chimera; Table 8, 12-month old No. 6, (C) the testis of the 2n-3n chimera; Table 8, 12-month old No. 2, and (D) the testis of the 1n-3n chimera; Table 8, 12-month old No. 6. The C value in the figure indicates the relative DNA content when the DNA content of the somatic cell of the normal diploid loach is set to 2C.

The injection of hCG into 12-month old 2n-3n enabled the collection of sperms from 4 of 6 individuals, and the sperms showed a normal morphology (FIG. 15A). In 1n-3n, sperms could be collected from 2 of 6 individuals. However, the concentration of sperms of 1n-3n was extremely lower compared to that of 2n-3n. The sperms showed a normal morphology like the collected sperms of 2n-3n (FIG. 15B). In the observation of the movement of sperms by the addition of fresh water under a light microscope, the movement of all of the 4 sperms which could be collected could be observed in 2n-3n, whereas no movement was observed in 1n-3n. The ploidy of the collected semen and the testis was detected using a flow cytometer. As a result, the ploidy of cells in the semen of 2n-3n was in (FIG. 16A). The testis of individuals in which sperms could be collected was composed of 1n, 2n, and 3n (FIG. 16C), 1n, 2n, 3n, and 4n, or 1n and 3n cells (Table 8). In the testis, a peak for 1n cells was high and peaks for 2n and 3n cells were low. The testis of individuals in which sperms could not be collected was composed of 3n cells (Table 8). The ploidy of the semen of 1n-3n was 1n (FIG. 16B), and the testis of one of individuals in which sperms could be collected was composed of 1n, 2n, 3n, and 4n cells (FIG. 16D). In the remaining one individual, the ploidy thereof could not be detected. The testis of individuals in which sperms could not be collected was composed of 3n cells (Table 8).

D. Material and Method

1. Expression of vasa mRNA

To examine whether cells in the developed testis of a chimeric adult fish are germ cells, the expression of germ cell-specific vasa mRNA was investigated. A part of the testis was taken out from 1n-3n and 2n-3n adult fishes 12, 15.5, and 16 months after hatching, placed in RNAlater (from Applied Biosystems), and allowed to stand in a refrigerator at 4° C. overnight, and then stored at −20° C. RNA was extracted according to a manual for Nucleo Spin RNAII (from MACH- EREY NAGEL). The extracted RNA was subjected to reverse transcription using Prime Script RT-PCR Kit (from Takara Bio Inc.) to synthesize cDNA. β-Actin as an internal control was also subjected to RT-PCR. Primers for RT-PCR were described below:

```
                                       (SEQ ID NO: 2)
    vasaRTF: CTGAACCTGCCATGGATGAC (SEQ ID NO: 3)
    vasaRTR: CTTCACCTCCTTTATAACCCTCAC (SEQ ID NO: 4)
    β-actinF: TTACCCACACCGTGCCCATCTAC (SEQ ID NO: 5)
    β-actinR: TACCGCAAGACTCCATACCCA
```

PCR was carried out under the following conditions.

After heating at 94° C. for 1 minute and then repeating 30 times the cycle of 94° C. for 30 seconds, 60° C. for 30 seconds, and 72° C. for 45 seconds, an extension reaction was carried out at 72° C. for 7 minutes. The PCR product was electrophoresed in 1.2% agarose gels and stained with ethidium bromide for visualization.

D. Result

1. Expression of vasa mRNA

Figure 17:
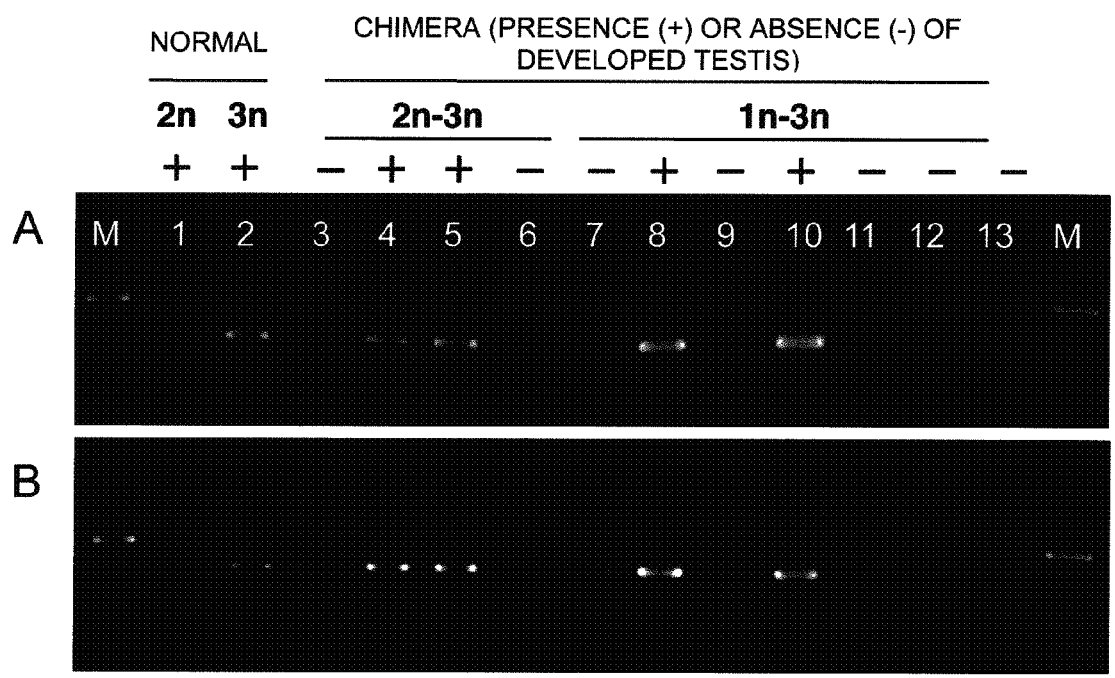
FIG. 17 is a pair of photographs showing the expression analysis by RT-PCR of the gene vasa expressed germ cell-specifically in the testis of adult normal diploid, adult triploid (derived from the crossing of a diploid female and a tetraploid male), 15.5-month old 2n-3n chimeric, and 15.5-month old 1n-3n chimeric loaches. (A) vasa, (B) β-actin, M: 100 bp ladder, 1: the normal diploid, 2: the triploid, 3 to 6: the 15.5-month old 2n-3n chimera (3: Tube-like gonad of No. 1, 4: A thick part of the gonad of No. 2, 5: A hyperplasia part of the gonad of No. 4), 6: An undeveloped part of the gonad of No. 4), 7 to 13: the 15.5-month old 1n-3n chimera (7: Tube-like gonad of No. 1, 8: A thick part of the gonad of No. 2, 9: An undeveloped part of the gonad of No. 2, 10: A thick part of the gonad of No. 3, 11: An undeveloped part of the gonad of No. 3, 12: Tube-like gonad of No. 4, 13: Tube-like gonad of No. 5) shown in Table 8.

The gene expression of vasa mRNA was investigated using RT-PCR. In the testis of 1n-3n and 2n-3n, developed in view of the external morphology of the testis, the expression of vasa mRNA was observed (FIG. 17A). However, in an undeveloped testis, the expression of vasa was not observed. Thus, cells in the 2n-3n and 1n-3n developed testis were confirmed to be germ cells.

Case of Goldfish, *Carassius auratus*

A. Material and Method

1. The goldfish, *Carassius auratus* was used as a material to produce a haploid-diploid germ line chimera (1n-2n) using a haploid as a donor and a normal diploid as a host and a haploid-triploid germ line chimera (1n-3n) using a haploid as a donor and a triploid as a host by a developmental engineering method as described below. The 1n-2n and 1n-3n were produced to examine whether haploid PGCs migrated to the genital ridge and proliferate as germ cells in a diploid or triploid host individual subjected to sterilization treatment by knock-down with the dead-end antisense morpholino oligonucleotide (SEQ ID NO: 6; 5'-TCCATGCCGCTGTCCAC-CTGTGATG-3') and whether functional gametes were formed in their gonads. When in the future it is examined whether functional gametes are formed or not, for a goldfish, to enable the DNA identification of the resultant offspring, a mother fish for obtaining a haploid and a mother fish for obtaining a host used were genetically different individuals.

2. Test Fish

In the present invention, the goldfish *Carassius auratus* during breeding in Field Science Center for Northern Biosphere, Hokkaido University were used as materials.

3. Collection of Egg and Sperm 10 to 20 IU/g body weight of hCG (ASKA Pharmaceutical Co., Ltd.) was intraperitoneally injected to parent goldfishes or tetraploid crucian carps to induce ovulation and spermiation. In the females, ovulation was confirmed 12 to 14 hours later, followed by collecting eggs by pressing their abdomen on a plastic petri dish 90 mm in diameter covered with Saran Wrap (polyvinylidene chloride film) (Asahi Kasei Corporation). In the males, their abdomen was also similarly pressed, and the resultant semen was subjected to the collection of sperms in a hematocrit capillary tube (from Terumo Corporation). The resultant semen was diluted about 50 to 100 times in an artificial seminal fluid for goldfish. To compare the genes of gametes and somatic cells in the prepared germ line chimera, fragments of the fin of parent individuals from which sperms and eggs were collected were fixed in 100% alcohol and stored at −80° C.

4. Genetical Inactivation of Sperm

Ultraviolet irradiation was used for the genetical inactivation of eggs and sperms. A box-shaped apparatus in the upper part of which an ultraviolet germicidal lamp (GL15W, from National) was placed was used. For the genetical inactivation of sperms, tetraploid crucian carp sperms diluted about 50 to 100 times with the artificial seminal fluid for goldfish were spread so as to provide a thickness of about 0.1 mm on a glass petri dish which was well washed and whose water content was wiped off, and irradiated with ultraviolet rays. The ultraviolet irradiation was at 60 mJ/cm². In the gynogenesis of goldfish, diploid sperms derived from a tetraploid crucian carp were used. The reason is because in the goldfish gynogenesis, fertilized eggs obtained from diploid sperms having escaped from the ultraviolet irradiation become triploid, do not form normal gametes, and can be removed.

5. Production of Haploid Donor and Diploid Host and Triploid Host

After inseminating goldfish eggs with ultraviolet-irradiated tetraploid crucian carp sperms, a gynogenetic haploid group of donor was produced by a method which involves scattering the resultant in a plastic petri dish filled with a fertilization solution at 20° C. for fertilization. The fertilization solution used a tap water containing 0.2% urea and 0.24% NaCl. A triploid group as hosts was also produced by the fertilization between common goldfish and tetraploid crucian carp sperms. In an embryo used as a host, sterility was induced by inhibiting the differentiation of PGC by the microinjection of dndMO (SEQ ID NO: 6; 5'-TCCATGCCGCT-GTCCACCTGTGATG-3) at the 1- to 4-cell stage after fertilization. For the haploid donor and triploid host group of a goldfish, control groups in which the egg chorion removal was not performed were prepared; within 5 hours after fertilization, unfertilized eggs were removed, and the count and removal of dead eggs every 1 day and the water exchange were further performed. The morphology of hatched larval fishes was observed during the period of the hatching of the haploid donor, and the occurrence rate of normal larval fishes and the number of appearance of larval fishes showing malformations such as a haploid syndrome were investigated. The stage of development was according to the report of Kajishima (1960).

6. Removal of Egg Chorion and Culture of Dechorionated Egg

About a half of fertilized eggs at the 1- to 2-cell stage in each experimental group were treated with a solution for removing the egg chorion containing Ringer's solution for freshwater fishes (128 mM NaCl, 2.8 mM KCl, 1.9 mM $CaCl_2$, pH 7.0) containing 0.1% trypsin and 0.4% urea to remove the egg chorion. Dechorionated eggs were cultured to the somitogenesis stage in a glass petri dish whose bottom face was subjected to coating treatment with about 1% agarose, filled with a primary culture (Ringer's solution for freshwater fishes, containing 1.6% chicken egg white, 0.01% penicillin, and streptomycin) at 20° C. Thereafter, the dechorionated eggs were transferred to a secondary culture (a 1.8 mM $CaCl_2$, 1.8 mM $MgCl_2$ solution containing 0.01% penicillin and streptomycin) and cultured to hatching.

7. Measurement of Ploidy of Donor Embryo and Host Larval Fish

To examine the success or failure of genetical inactivation of a sperm, the ploidy of the donor embryo used in producing the chimera was investigated using a flow cytometer (Partec Ploidy Analyser, Model PA). To examine whether a host was triploid or diploid, the ploidy of a control host larval fish from which the egg chorion was not removed was also investigated. The donor embryo and the host larval fish were each placed in 150 μl of solution A (a nuclear isolation solution) for Cystain DNA 2 step kit (Partec) and allowed to stand for 20 minutes, and cells were mixed and dissociated by vortex. Thereafter, the specimen was filtered with a 50-μm mesh (Cell Tries 50 μm, Partec), to which solution B (a stain solution containing 4',6-diamidino-2-phenylindole (DAPI)) at a volume of 5 times that of the solution A was added after removing cell debris to measure the relative DNA content by flow cytometry. Here, the DNA content of the fin of the normal diploid goldfish was used as a standard for the diploid DNA content (2C), and the DNA content of the haploid sperm of the normal diploid goldfish employed therein was used as a standard for the haploid DNA content (1C). The donor embryo and host larval fish used for producing a 2n-3n chimera were also further examined for ploidy.

8. Production of Germ Line Chimera in Goldfish

PGC was revealed by injecting GFP-nos1 3'UTR mRNA into the dechorionated haploid egg at the 1- to 4-cell stage. When the egg reached the blastula stage, a germ line chimeric individual was induced by a "blastomere transplantation method: BT method" involving aspirating blastomeres around the blastoderm and transplanting them into the host blastula, a "blastoderm transplantation method: sandwich method" involving cutting away the lower part of the blastoderm and transplanting the resultant into the midportion of the host blastula, a "SPT method" involving one of the PGCs revealed at the somitogenesis stage into the host blastula, or a "PPT method" involving transplanting a plurality thereof. As a host, a 2n or 3n embryo into which the above dndMO was microinjected to inhibit the formation of PGC was used. The donor cell-transplanted embryo was cultured and observed under a fluorescence microscope, and an individual in which PGCs emitting GFP fluorescence was identified in the genital ridge was separated as a germ line chimera and subjected to continuous breeding.

9. Collection of Goldfish Chimera Gamete and Determination of Ploidy

To examine the presence of the differentiation of a gamete in a 1n-3n chimera, hCG was injected into the chimeric individual according to the above method of egg collection and sperm collection. On the day following the injection, the abdomen was pressed to identify the presence of ovulation or spermiation. Sperms were taken from the spermiated individual into a hematocrit capillary tube, and further the semen was suspended in an artificial seminal fluid. A fin fragment was collected from the individual and stored in Ringer's solution for freshwater fishes. The fin or the serum suspension was placed respectively in 150 μl of solution A (a nuclear isolation solution) for Cystain DNA 2 step kit (Partec) and allowed to stand for 20 minutes, and cells were mixed and dissociated by vortex. Thereafter, the specimen was filtered with a 50-μm mesh (Cell Trics 50 μm, Partec), to which solution B (a stain solution containing 4',6-diamidino-2-phenylindole (DAPI)) at a volume of 5 times that of the solution A was added after removing cell debris to measure the relative DNA content by flow cytometry. Here, the DNA content of the fin of the normal diploid goldfish was used as a standard for the diploid DNA content (2C), and the DNA content of the haploid sperm of the normal diploid goldfish employed therein was used as a standard for the haploid DNA content (1C). In contrast, there has previously been no example in which ovulation was identified.

10. Verification that Goldfish Chimera Gamete is Derived from Donor PGC

In a chimeric individual identified for spermiation, to establish whether the sperm is derived from donor PGC, determination by crossing and the comparison between the sperm genome and the somatic cell genome were carried out. In the determination by crossing, DNA were extracted from a donor mother for haploid germ cells of a wild-type chimera, a mother and a farther for a chimeric host, a fin of a chimeric individual, and chimera sperms and subjected to RAPD analysis and genetic analysis using a microsatellite marker. For DNA, a part of a sample fixed in ethanol was immersed in a TNES-Urea buffer containing Proteinase K at a concentration of 250 μg/mL and incubated at 37° C. overnight for protein digestion. Thereafter, DNA extraction was carried out by a phenol/chloroform method.

A. Result

1. Fertilization Rate, Normal Development Rate, and Germ Line Chimera Induction Rate of Goldfish BT Chimera Group and Control Group The survival rate, normal development rate, and germ line chimera rate of 1n-3n chimera produced by the BT (blastomere transplantation) method are summarized in Table 9, Haploid donors were produced by gynogenesis. The host used was an embryo from a fertilized egg between a goldfish egg and a diploid sperm obtained from a tetraploid crucian carp, into which dndMO was injected. As controls in producing a chimera, there were used a haploid individual control group in which the injection of GFP nos1 3'UTR mRNA was not performed and the egg chorion was removed and a triploid host control group in which the microinjection of dnd MO was performed after the removal of the egg chorion. The number of eggs used, the number of fertilized eggs, the number of hatched larval fishes, the number of normal larval fishes, and the numbers of malformed larval fishes were counted in both the transplantation group and the control groups. As a result, about a half of each of the transplantation group and the triploid host control group became normal larval fishes. All of the gynogenesis group produced as donors showed malformations determined as indicating the so-called haploid syndrome after hatching. In ¼ of the transplantation group showing the normal morphology, cells which are probably donor PGCs were observed in the gonad region. As a result of measuring the DNA content of the haploid individual having provided donor cells when the control embryo hatched, the DNA content was a DNA content all of which is probably that of a haploid.

TABLE 9

Survival Rate and Normal Development Rate of Goldfish Haploid PGC → Sterilized Triploid Host BT Germ Line Chimera

|  | Total Number | Number of Surviving (3 dpf) | (%) | Number of Normal Embryos | (%) |
| --- | --- | --- | --- | --- | --- |
| 1n-3nMO BT Chimera | 39 | 29 | 74.4% | 12 | 30.8% |
| 1n-3n BT Chimera | 36 | 24 | 66.7% | 1 | 2.8% |
| Haploid Dechorionated Control | 12 | 4 | 33.3% | 2 | 16.7% |
| 3n MO Dechorionated Control | 81 | 69 | 85.2% | 13 | 16.0% |

TABLE 9-continued

Survival Rate and Normal Development Rate of Goldfish Haploid PGC → Sterilized Triploid Host BT Germ Line Chimera

| | Total Number | Number of Surviving (3 dpf) | (%) | Number of Normal Embryos | (%) |
|---|---|---|---|---|---|
| Triploid Dechorionated Control | 28 | 25 | 89.3% | 18 | 64.3% |
| Haploid Untreated Control | 24 | 15 | 62.5% | 0 | 0.0% |

2. Fertilization Rate, Normal Development Rate, and Germ Line Chimera Induction Rate of Goldfish Sandwich Chimera Group and Control Group The survival rate, normal development rate, and germ line chimera rate of 1n-3n chimera produced by the sandwich (blastoderm transplantation) method are summarized in Table 10. Haploid donors were produced by gynogenesis. The host used was an embryo from a triploid fertilized egg between a goldfish egg and a diploid sperm obtained from a tetraploid crucian carp, into which dndMO was injected. As controls in producing a chimera, there were used a haploid individual control group in which the injection of GFP nos1 3'UTR mRNA was not performed and the egg chorion was removed and a triploid host control group in which the microinjection of dnd MO was performed after the removal of the egg chorion. The number of eggs used, the number of fertilized eggs, the number of hatched larval fishes, the number of normal larval fishes, and the number of malformed larval fishes were counted in both the transplantation group and the control groups. As a result, 93.3% of the triploid host control group normally developed, whereas only about 59% of the transplantation group did so. In the haploid control group, no individual normally developed and all individuals were malformed larval fishes determined as having haploid syndrome. In ⅓ of the transplantation group showing the normal morphology, cells which are probably donor PGCs were observed in the gonad region.

TABLE 10

Survival Rate and Normal Development Rate of Goldfish Haploid PGC → Sterilized Triploid Host BT Germ Line Chimera, Origin of Sandwich Chimera

| | Total Number | Number of Surviving (3 dpf) | (%) | Normal Embryo | (%) | PGC Positive | (%) |
|---|---|---|---|---|---|---|---|
| 1n-3n MO Sandwich Chimera (080430) | 61 | 39 | 63.9% | 36 | 59.0% | 12 | 19.7% |
| Haploid Dechorionated Control | 69 | 58 | 84.1% | 0 | 0.0% | — | — |
| 3n MO Dechorionated Control | 60 | 59 | 98.3% | 56 | 93.3% | — | — |

3. Comparison of Rates of Induction of Germ Line Chimera by SPT Method and PPT Method with Goldfish The survival rate, normal development rate, and germ line chimera rate of 1n-2n chimera produced by the SPT method or the PPT method are summarized in Table 11. Haploid donors were produced by gynogenesis. The host used was a diploid fertilized egg between goldfishes. As controls in producing a chimera, there were used a diploid host in which the microinjection of dnd MO was performed after the removal of the egg chorion, and a diploid host fertilized egg. 90% or more of each of the experimental groups and the control groups normally developed. The proportion of individuals in which donor PGC migrated to the genital ridge was only 29.9% of the normal embryos in the SPT group in which one PGC was transplanted, while it was 82.4% in the group in which 5 PGCs were transplanted.

TABLE 11

Survival Rate, Normal Development Rate, and Rate of Arrival of Donor PGC at Host Genital Ridge of 1n-2n Germ Line Chimera Induced by Single Primordial Germ Cell Transplantation Method (SPT method) and Poly Primordial Germ Cell Transplantation Method (PPT method) in Goldfish

| | Total Number | Number of Surviving (3 dpf) | (%) | Normal Embryo | (%) | PGC Positive | | | |
|---|---|---|---|---|---|---|---|---|---|
| | | | | | | GR | % | Ect | % |
| 1n-2n dnd SPT Chimera 090614 | 24 | 24 | 100.0% | 24 | 100.0% | 7 | 29.2% | 12 | 50.0% |

TABLE 11-continued

Survival Rate, Normal Development Rate, and Rate of Arrival of Donor PGC at Host Genital Ridge of 1n-2n Germ Line Chimera Induced by Single Primordial Germ Cell Transplantation Method (SPT method) and Poly Primordial Germ Cell Transplantation Method (PPT method) in Goldfish

| | Total Number | Number of Surviving (3 dpf) | (%) | Normal Embryo | (%) | PGC Positive GR | % | Ect | % |
|---|---|---|---|---|---|---|---|---|---|
| 1n-2n dnd PPT Chimera 090614 | 36 | 34 | 94.4% | 34 | 94.4% | 28 | 82.4% | 6 | 17.6% |
| Host dnd Control | 36 | 36 | 100.0% | 34 | 94.4% | | | | |
| Host dnd Control | 36 | 35 | 97.2% | 34 | 94.4% | | | | |

GR: Genital Ridge,
Ect: Other Than Genital Ridge

4. Fertilization Rate, Normal Development Rate, and Germ Line Chimera Induction Rate by Goldfish PPT Method The survival rate, normal development rate, and germ line chimera rate of 1n-3n chimera produced by the PPT method (poly primordial germ cell transplantation method) are summarized in Table 12. Haploid donors were produced by gynogenesis. The host used was an embryo from a fertilized egg between a goldfish egg and a diploid sperm obtained from a tetraploid crucian carp, into which dndMO was injected. As controls in producing a chimera, there were used a dechorionated egg and a non-dechorionated egg of a haploid individual in which the injection of GFP nos1 3'UTR mRNA was not performed, a host triploid control group in which the microinjection of dnd MO was performed after the removal of the egg chorion, and a triploid control group in which the egg chorion was not removed. The number of eggs used, the number of fertilized eggs, the number of hatched larval fishes, the number of normal larval fishes, and the number of malformed larval fishes were counted in both the transplantation group and the control groups. As a result, 90% or more each of the dnd MO-injected triploid host control group and the triploid control group normally developed, whereas about 88.1% of the transplantation group did so. In the dechorionated haploid control group, no individual normally developed and all individuals were malformed larval fishes determined as having haploid syndrome. In the non-dechorionated haploid control group, 2 (3.6%) normal individuals appeared. In the PGC transplanted group, donor PGC was identified in the genital ridge of 17 (28.8%) individuals.

TABLE 12

Survival Rate, Normal Development Rate, and Rate of Arrival of Donor PGC at Host Genital Ridge of 1n-3n Germ Line Chimera Induced by PPT method in Goldfish

| | Total Number | Number of Surviving (2 dpf) | (%) | Normal Embryo | (%) | PGC Positive GR | % | Ect | % |
|---|---|---|---|---|---|---|---|---|---|
| 1n-3nMO PPT Chimera (090307) | 67 | 65 | 97.0% | 59 | 88.1% | 17 | 28.8% | 20 | 33.9% |
| 3nMO Dechorionated Control | 27 | 27 | 100.0% | 25 | 92.6% | — | — | — | — |
| Haploid Dechorioanated Control | 96 | 85 | 88.5% | 0 | 0.0% | — | — | — | — |
| Triploid Dechorionated Control | 40 | 40 | 100.0% | 38 | 95.0% | — | — | — | — |
| Haploid Dechorionated Control | 56 | 54 | 96.4% | 2 | 3.6% | — | — | — | — |

GR: Genital Ridge,
Ect: Other Than Genital Ridge

5. Dynamic State of Goldfish Haploid PGC in Diploid Host

The dynamic state of donor PGC was followed in a chimera individual into which a plurality of haploid PGCs were transplanted. The individual as a host used was an albino transparent scale individual in which no melanotic pigment appeared. The transplanted PGCs were mainly located around the genital ridge; however, some of them were observed to be distributed around the notochord. The division of the donor PGCs was identified 4 weeks after transplantation. It could not be externally observed 5 weeks after transplantation. Thus, as a result of fixing the individual and histologically observing the gonad, an increase in PGC in the gonad was identified.

6. Differentiation of Gamete in Goldfish BT Chimera

A BT chimera was produced, and the chimera and a control group therefor were subjected to laparotomy after a year and a half to identify the presence of the gonad. At this time, 4 chimeric individuals, 1 individual of the MO control group, and 6 individuals of the triploid control group survived. The testis was identified in 1 individual of the chimera group, and undeveloped linear gonads were identified in the remaining 3 individuals. The gonad of the MO control group was linear and corresponded to the linear gonad of the chimeric individuals. In the triploid control group, the testis was identified in 5 individuals and the ovary was identified in 1 individual. The semen from the chimeric individuals, the identified testis and linear gonad, and the fragment of the testis identified in the triploid control group were subjected to FCM to determine the ploidy of constituting cells. As a result, the semen obtained from the individual having the developed testis of the chimeric individual had s ploidy of 1n and cells constituting the testis had ploidies of 1n, 2n, and 3n. In the individuals having undeveloped gonads, cells from the body fluid from the cloaca obtained after the hormone injection were 3n, and the gonad was composed of only 3n cells. In the gonad of the triploid control group, cells corresponding to 1.5n, 3n, and 6n were observed. In any group, somatic cells of the fin had a relative DNA content of 3n. These results show that only the chimera into which haploid PGC was transplanted produces the semen of 1n.

7. Differentiation of Gamete in Goldfish PPT Chimera

Figure 18:
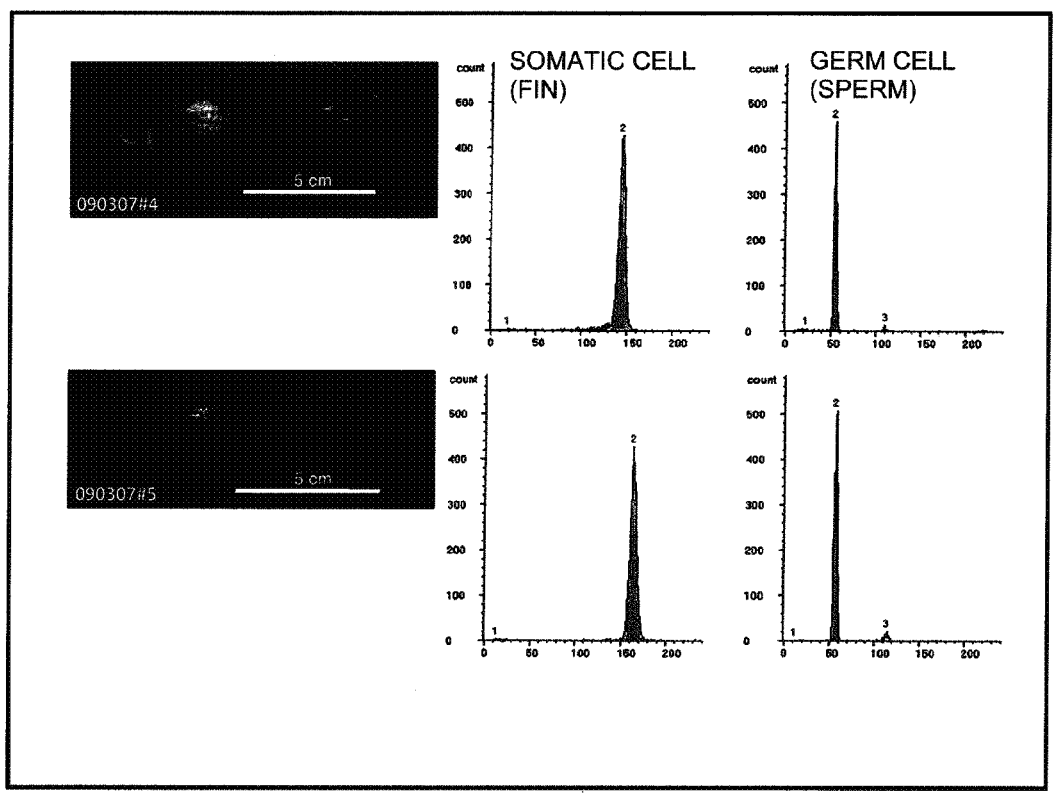
FIG. 18 is a drawing showing the external morphologies and the results of FCM analysis of the fin and sperm of wild-type haploid PGC→3n chimeric goldfishes prepared by the PPT method.

In a PPT chimera obtained by transplanting haploid PGC into a sterilized triploid, 8 individuals survived. hCG was injected to these chimeric individuals to identify spermiation and the ploidy thereof. Spermiation was observed in 2 individuals (090307#4 and 090307#5), and as a result of FCM, it was determined that somatic cells of the fin were triploid and the sperm was haploid (FIG. 18).

Figure 19:
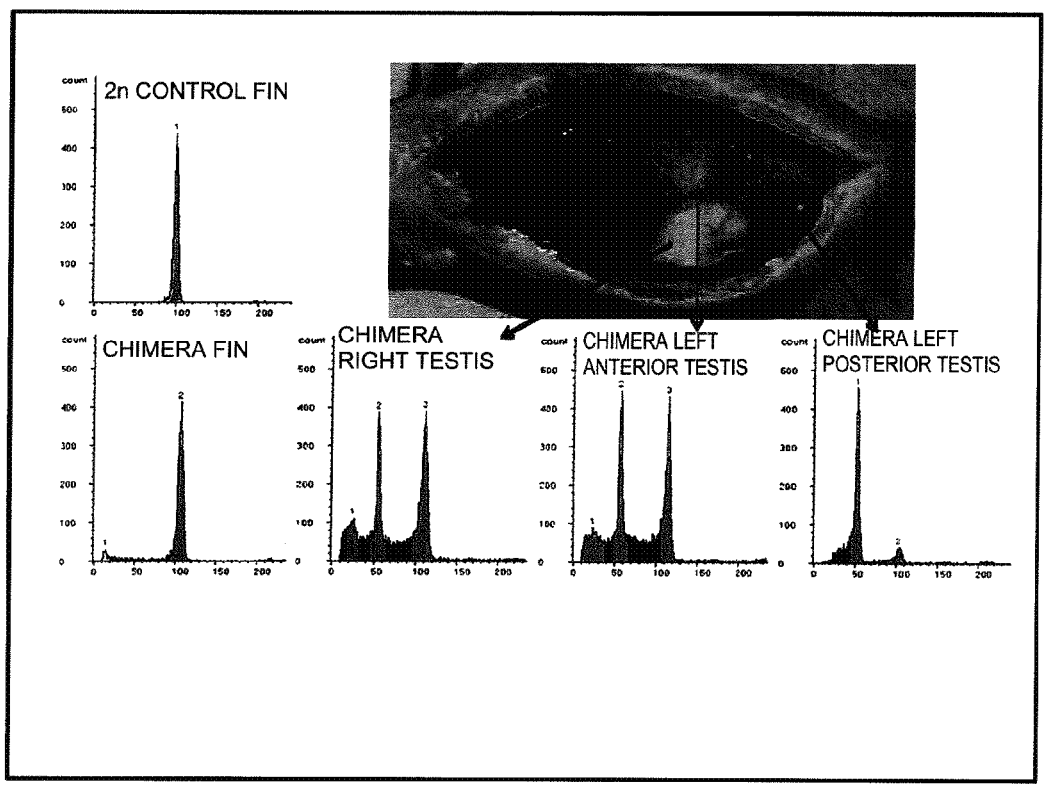
FIG. 19 is a drawing showing the gonad and the results of FCM analysis thereof of a wild-type haploid PGC→albino 2nPPT chimeric goldfish prepared by the PPT method.
Figure 20:
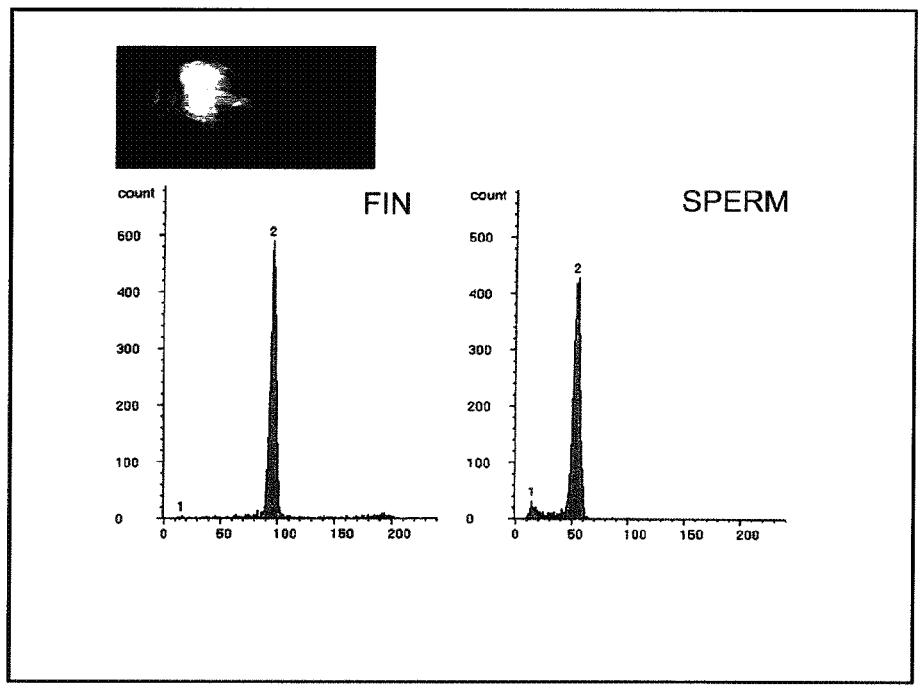
FIG. 20 is a drawing showing the external morphology and the results of FCM analysis of the sperm and fin of wild-type haploid PGC→albino 2n chimeric goldfish individual 090622 prepared by the PPT method.

Among the PPT chimeric individuals obtained by transplanting wild-type haploid PGC into a sterilized albino diploid, as a result of dissecting an individual having died on the way, the testis was identified in both the left and right sides (FIG. 19). As a result of identifying the ploidy of cells constituting these testis fragments by FCM, haploid and diploid cells were identified. In addition, as a result of histologically observing the testis, male germ cells at each stage including spermatids were identified. Cells capable of being asserted as sperms were not observed. Spermiation was identified in 1 surviving individual (090622), and the sperms were identified to be haploid sperms by FCM (FIG. 20). The sperm of the chimeric individual (090622) identified for spermiation was fertilized with an egg obtained from an albino female individual. As a result, all of the offspring (n=70) had a melanotic pigment characteristic of wild type (Table 13). This demonstrated that the sperm was derived from wild-type haploid PGC providing a donor.

B. Material and Method

1. RAPD Analysis in Goldfish

In RAPD (Randomly amplified polymorphic DNA) analysis, OPA-2, OPA-4, and OPA-11 (Operon) in which polymorphism was observed were used as primers. PCR reaction used a 0.2-mL tube and rTaq DNA Polymerase (Takara), and the buffer included with the enzyme was used to prepare a 20-4 reaction system (1×PCR buffer (containing $Mg^{2+}$), 0.2 mM dATP, 0.2 mM dTTP, 0.2 mM dGTP, 0.2 mM dCTP, Primer 0.5 µM, rTaq DNA Polymerase (Takara) 1 U, Template DNA 2.5-5 ng). The PCR reaction was performed under reaction conditions of one cycle of 94° C. for 3 minutes, 30 cycles of 94° C. for 30 seconds, 36° C. for 1 minute, and 72° C. for 1 minute, and one cycle of 72° C. for 7 minutes, and the reaction product was stored at 4° C. after the end of reaction. The resultant PCR product was subjected to electrophoresis for 75 minutes using 1.5% agarose gel, and DNA was stained with ethidium bromide, followed by detecting a band using a UV transilluminator.

B. Result

Figure 21:
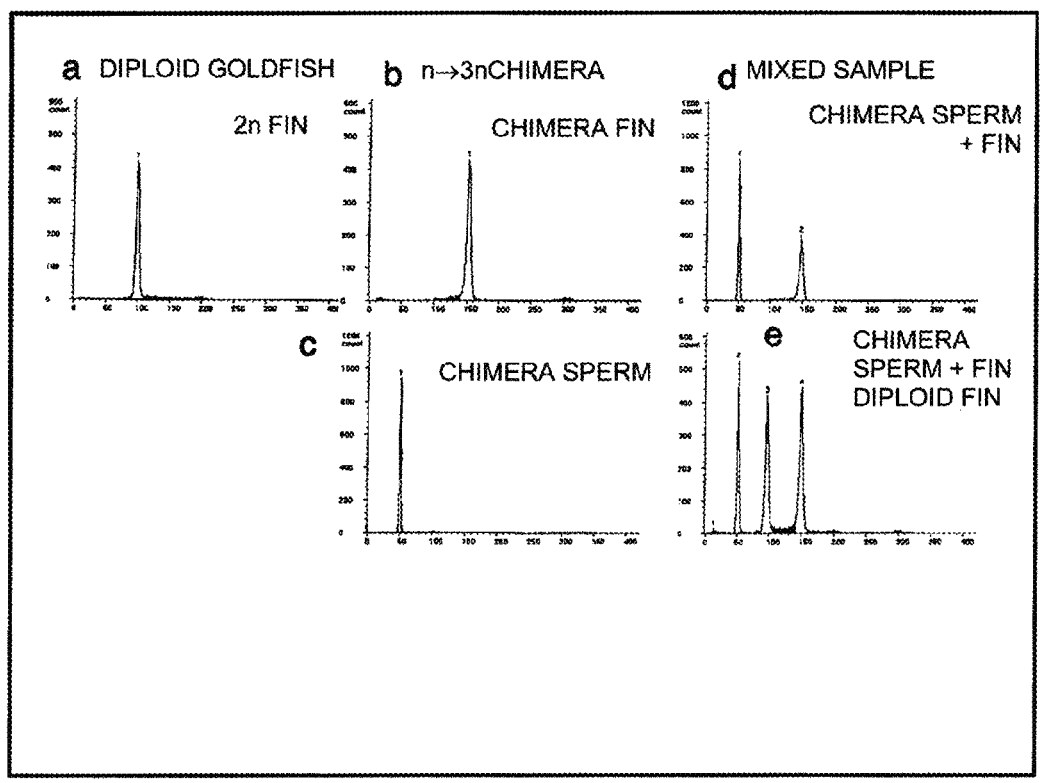
FIG. 21 is a series of graphs showing the results of FCM analysis of the sperm and fin of a haploid PGC→dead end antisense morpholino oligonucleotide (hereinafter also referred to as "dndMO") triploid chimeric goldfish prepared by the Sandwich method.
Figure 22:
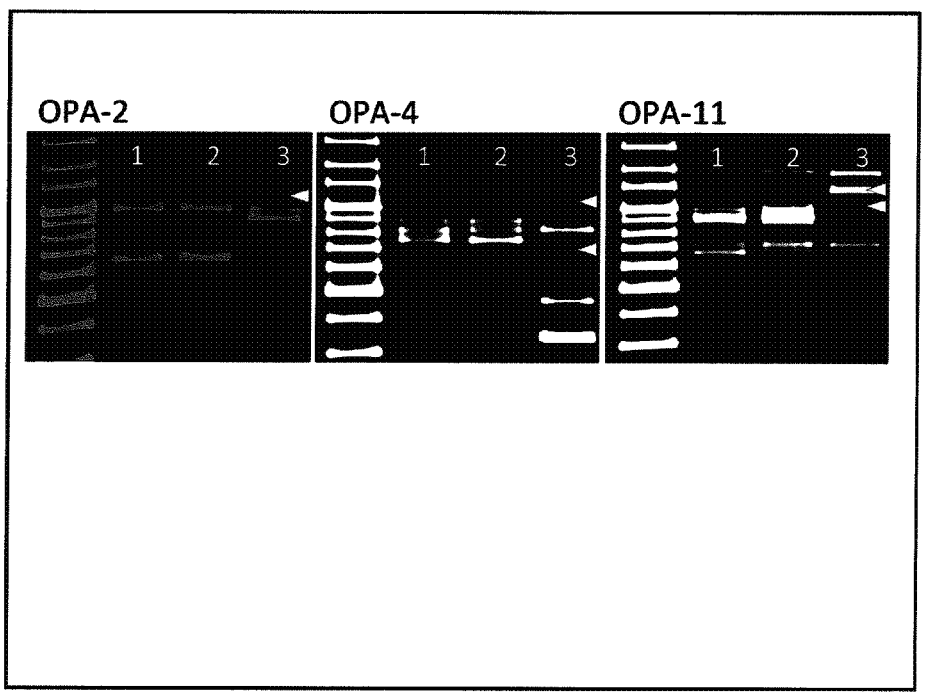
FIG. 22 is a series of photographs showing the results of genetic analysis of the sperm and somatic cell of a haploid PGC→dndMO triploid chimeric goldfish prepared by the Sandwich method, using an RAPD marker. Lane 1: the fin DNA of a 4n male crucian carp used for preparing the triploid host, Lane 2: the fin DNA of the 1n-3n chimera, and Lane 3: the sperm DNA of the 1n-3n chimera; the arrow heads indicate specific bands for the sperm of the 1n-3n chimera.

1. Differentiation of Gamete in Goldfish Sandwich Chimera and RAPD Analysis Thereof hCG was injected to two Sandwich chimeric individuals bred for 1 year to identify spermiation and the ploidy thereof. Spermiation was observed in 1 individual (080430), and as a result of FCM, it was determined that somatic cells of the fin were triploid and the sperm was haploid (FIG. 21). hCG was injected to 5 large individuals of 25 surviving individuals in the dnd-MO control group; however, no spermiation or ovulation was identified. DNA was extracted from somatic cells and sperms of the chimeric individual identified for spermiation and somatic cells of the father of a host and subjected to RAPD analysis (FIG. 22). Bands different from those of the chimeric individual and the father of the host were identified in bands amplified using sperm DNA of the chimera as a template, confirming that DNA derived from donor haploid PGC was contained in the sperm of the chimera. Samples of cells of parents of the donor and the host from which the individual was produced were not stored; thus, further analysis could not be performed.

C. Material and Method

1. Primer for Microsatellite Analysis in Goldfish

For the identification of clonal nature in a chimera using goldfish, a microsatellite developed in a goldfish (Zheng et al., Molecular Ecology 4, 791-792, 1995, Jung et al., Molecular Ecology Notes 7, 124-126, 2007) and a microsatellite developed in a carp as a related species (Crooijmans et al., Animal Genetics 28, 129-134, 1997, Yue et al., Aquaculture 234, 85-98, 2004) were used (Table 14). The polymorphism of a host, a donor, and a parental fishes used for crossing with the chimera was examined using a total of 14 goldfish-derived microsatellite markers: GF-1, 11, 17, 20, and 29 (Zheng et al., 1995) and CAL-0120, 0428, 04100, 0410, 0461, 0174, 0192,

TABLE 13

Frequency of Phenotype of offspring obtained from a crossing by Goldfish Wild-Type Haploid PGC → Albino 2nPPT Chimera

| Female | Male | Total Number | Survival Number | (%) | Wild-Type Number | (%) | Albino-Type Number | (%) |
|---|---|---|---|---|---|---|---|---|
| Albino | 1n-2n Chimera (090623) | 96 | 70 | 72.9% | 70 | 100.0% | 0 | 0.0% |
| | Albino | 72 | 65 | 90.3% | 0 | 0.0% | 65 | 100.0% |
| | Wild | 53 | 48 | 90.6% | 48 | 100.0% | 0 | 0.0% |

0156, and 0495 (Jung et al., 2007) and a total of 12 carp-derived microsatellite markers: MFW-2, 7, and 17 (Crooijmans et al., 1997) and Cca-02, 04, 12, 19, 22, 67, 86, and 91 (Yue et al., 2004). The polymorphism was observed in the 10 loci of GF17, GF29, MFW7, MFW17, CAL0428, CAL0174, CAL0192, Cca12, Cca86, and Cca91 among the above markers.

TABLE 14

Microsatellite Markers Used for DNA Analysis of Gamete of Goldfish Chimera into Which Haploid PGC Was Transplanted

| Marker Series | Number of Markers | Microsatellite Locus | Paper on Developed Fish Species | Xenogeneic Proliferation |
|---|---|---|---|---|
| GF | 5 | 1, 11, 17, 20, 29 | Goldfish Carassius auratus Zheng etal, 1995 | — |
| MFW | 3 | 2, 7, 17 | Colored Carp Cyprinus carp b L. Crooijmans etal, 1997 | Papoušk etal, 2008 |
| CAL | 9 | 0120, 0428, 04100, 0410, 0461, 0174, 0192, 0156, 0495 | Goldfish Carassius auratus Jung etal, 2007 | — |
| Coa | 8 | 02, 04, 12, 19, 22, 67, 86, 91 | Colored Carp Cyprinus carp b L. Yue etal, 2004 | Yue etal, 2004 |

2. Microsatellite Analysis in Goldfish

In this analysis, host parents' DNA and donor parents' DNA used for a chimera and DNA derived from the fin and sperm of the chimera were used as template DNA. A primer in which 5'-AGTCACGACGTTGTA-3' (SEQ ID NO: 7) was added to the 5' terminal end of the above primer sequence was used as a forward primer for a marker used for analysis. The PCR reaction and the analysis of genotype used an annealing temperature optimal for each primer set between 50° C. and 56° C.; PCR was performed by the M13-tailed method using a M13 primer: 5'-GCCAGTCACGACGTTGTA-3' (SEQ ID NO: 8) to which a fluorochrome: FAM, VIC, PET, or NED was added based on Morishima et al. Genetica 132, 227-241, (2008), electrophresis was carried out using ABI3030xl autosequencer (ABI), and the genotype was analyzed using GeneMapper program Ver 3.7 (ABI).

3. Analysis of Clonal Nature of Gametes from Goldfish Chimera

To determine that all of the sperms obtained from one chimeric individual were genetically uniform (clonal) in chimeric individuals identified for spermiation, a hybrid was prepared by fertilizing an egg produced by a cloned loach with a sperm obtained from the chimera to separate an individual expressing the morphology of the hybrid. Then, DNA was extracted from the hybrid and analyzed using the goldfish-derived microsatellite marker. Samples of a donor mother for chimera haploid germ cells, parents of the chimera host, and the fin of a chimera individual were also collected. DNA were extracted from these samples and subjected to RAPD analysis and microsatellite analysis.

4. Genetic Analysis of Sperm Derived from Chimera into Which Goldfish Haploid PGC was Transplanted The further detailed genetic analysis of sperms was carried out in a chimeric individual into which haploid PGC confirmed to be derived from a donor described above was transplanted. Parents' somatic cells from which a haploid donor was induced, parents' somatic cells from which a host individual was induced, and somatic cells and sperms of a chimeric individual were used as materials to extract DNA from these cells, and the resultant DNA was used for the analysis. Then, DNA of the parents' somatic cells from which a haploid donor was induced, the parents' somatic cells from which a host individual was induced, and the somatic cells and sperms of a chimeric individual were analyzed. The analysis used microsatellite markers reported for a goldfish and a carp (Table 14).

C. Result

Figure 23:
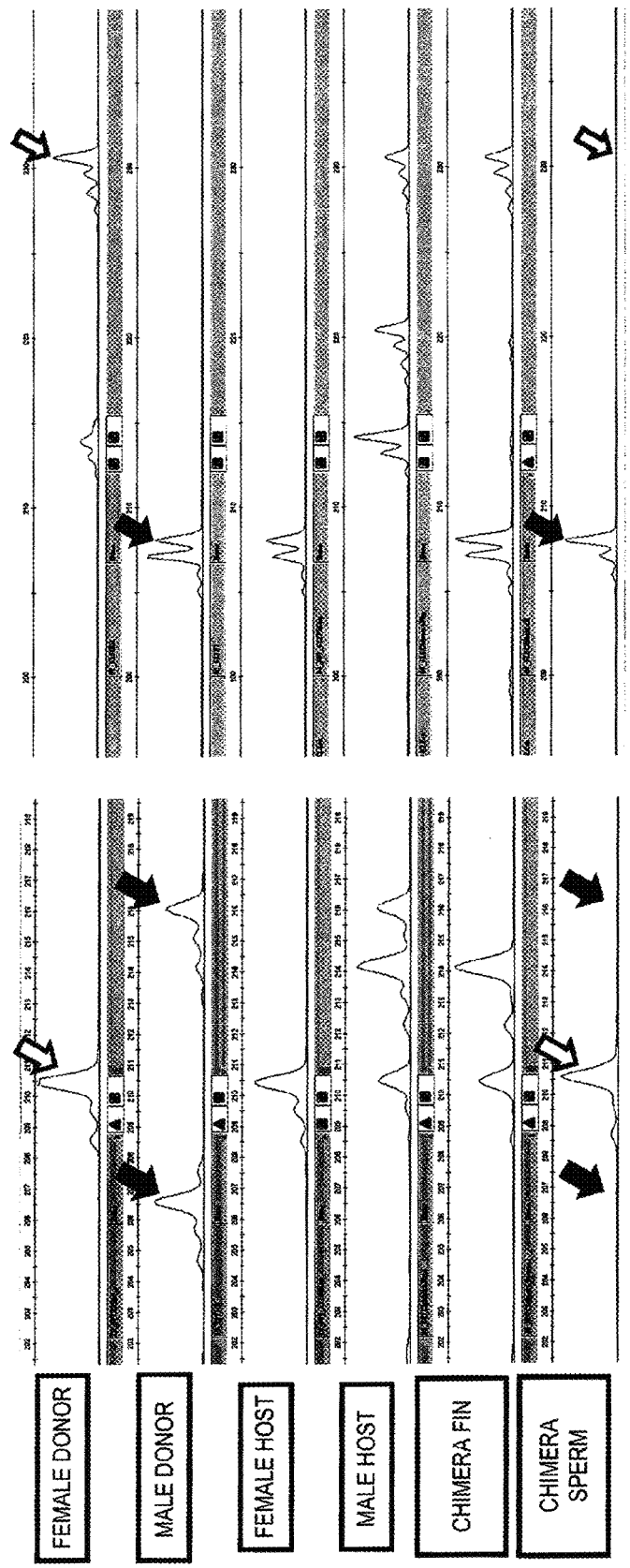
FIG. 23 is a conceptual diagram for the experiment of reconfirmation of gynogenesis in a germ line chimeric goldfish into which haploid PGC is transplanted. It was confirmed that a marker (open arrow) for the mother (female donor) appeared in the gamete of the germ line chimera and a marker (black arrow) for the father (male donor) did not appear. The left shows an example of no appearance of the male marker and the right shows an example of the appearance thereof.

1. Re-Verification of Gynogenesis of Chimeric Donor into which Goldfish Haploid PGC was Transplanted To determine whether the transplanted donor PGC was derived only from a female parent, it was determined whether microsatellite markers in the chimera sperm were derived only from the female and do not include such a marker derived from a male (FIG. 23). As a result, for 3 individuals other than 090613#4 individual, only female-derived loci were observed, demonstrating that gynogenesis occurred (Table 15).

TABLE 15

Result of Reconfirmation Experiment of Gynogenesis in Germ Line Chimera in Which Haploid PGC Was Transplanted in Goldfish

| | Confirmed Gynogenesis Haploid | |
|---|---|---|
| | Marker different between Donor Male and Female | Allele of Donor Male Observed in Sperm |
| 20090307 #4 | 3 | 0 |
| 20090307 #5 | 3 | 0 |
| 20090613 #4 | 3 | 1 |
| 20090622 | 1 | 0 |

Figure 24:
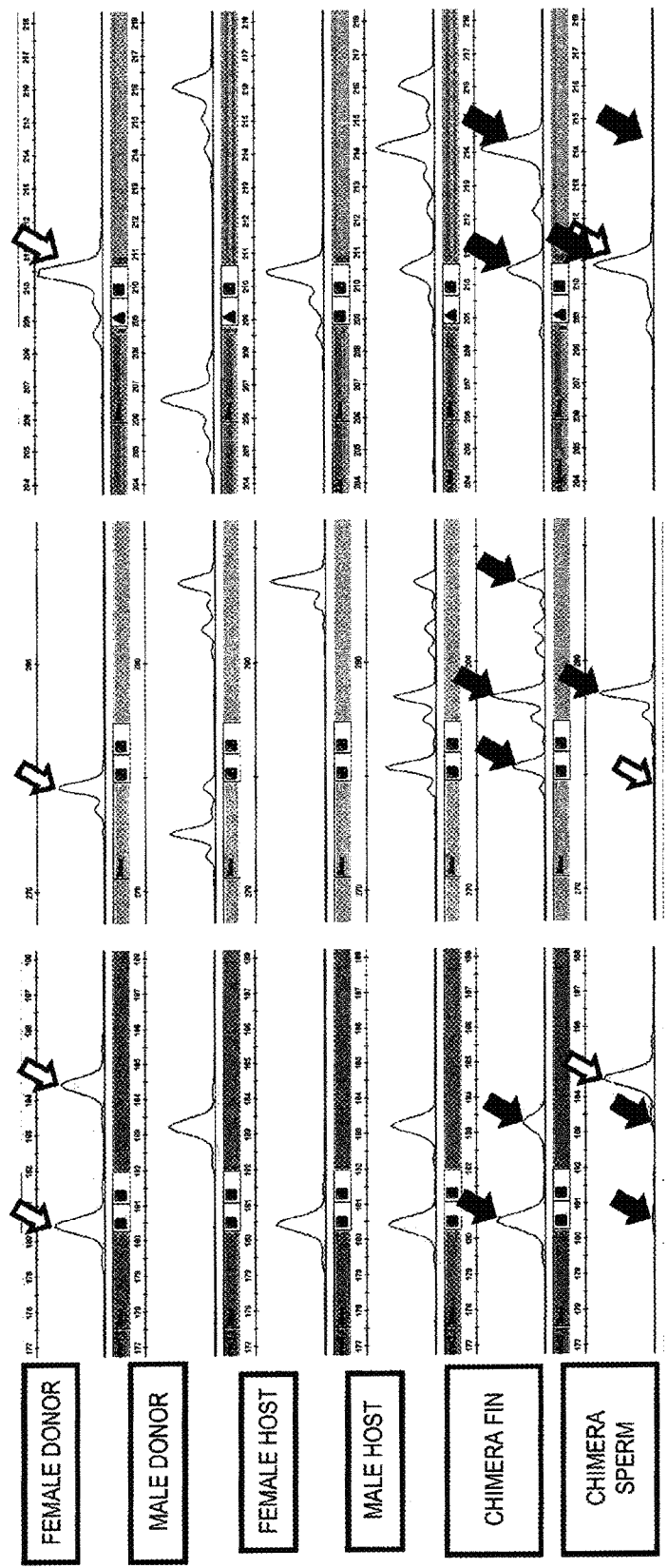
FIG. 24 is a conceptual diagram for the experiment of reconfirmation of the origin of PGC in a germ line chimeric goldfish into which haploid PGC is transplanted. It was confirmed that a marker (black arrow) for the somatic cell of the germ line chimera (the fin of the chimera) did not appear in the gamete of the germ line chimera and a marker (open arrow) for the mother (female donor) appeared. The left shows an example of no appearance of a marker for the host in the gamete of the chimera; the middle, an example of the appearance of only a marker for the host; and the right, an example in which the markers cannot be discriminated because of their overlap.

2. Presence or Absence of Involvement of Host Genome in Gamete of Chimera into which Goldfish Haploid PGC was Transplanted It was determined whether the chimera sperm contains a host-derived genome (FIG. 24). As a result, the 3 individuals of 090307#4, 090307#5, and 090622 each contained only markers for a donor female, while loci only for a host were observed in 090613#4 (Table 16). From this result, the sperms of the 3 individuals of 090307#4, 090307#5, and 090622 were each probably derived from a donor female. The sperm obtained from 090613#4 is probably derived from a host.

TABLE 16

Result Indicating That Gamete Derived from Germ Line Chimera in Which Haploid PGC Was Transplanted in Goldfish Was Not Derived from Host.

| | | Genome Organization of Sperm | | |
|---|---|---|---|---|
| | Number of Markers | Only Donor Female | Only Host | Both |
| 20090307 #4 | 8 | 2 | 0 | 6 |
| 20090307 #5 | 9 | 2 | 0 | 7 |
| 20090613 #4 | 8 | 0 | 2 | 6 |
| 20090622 | 10 | 4 | 0 | 6 |

Figure 25:
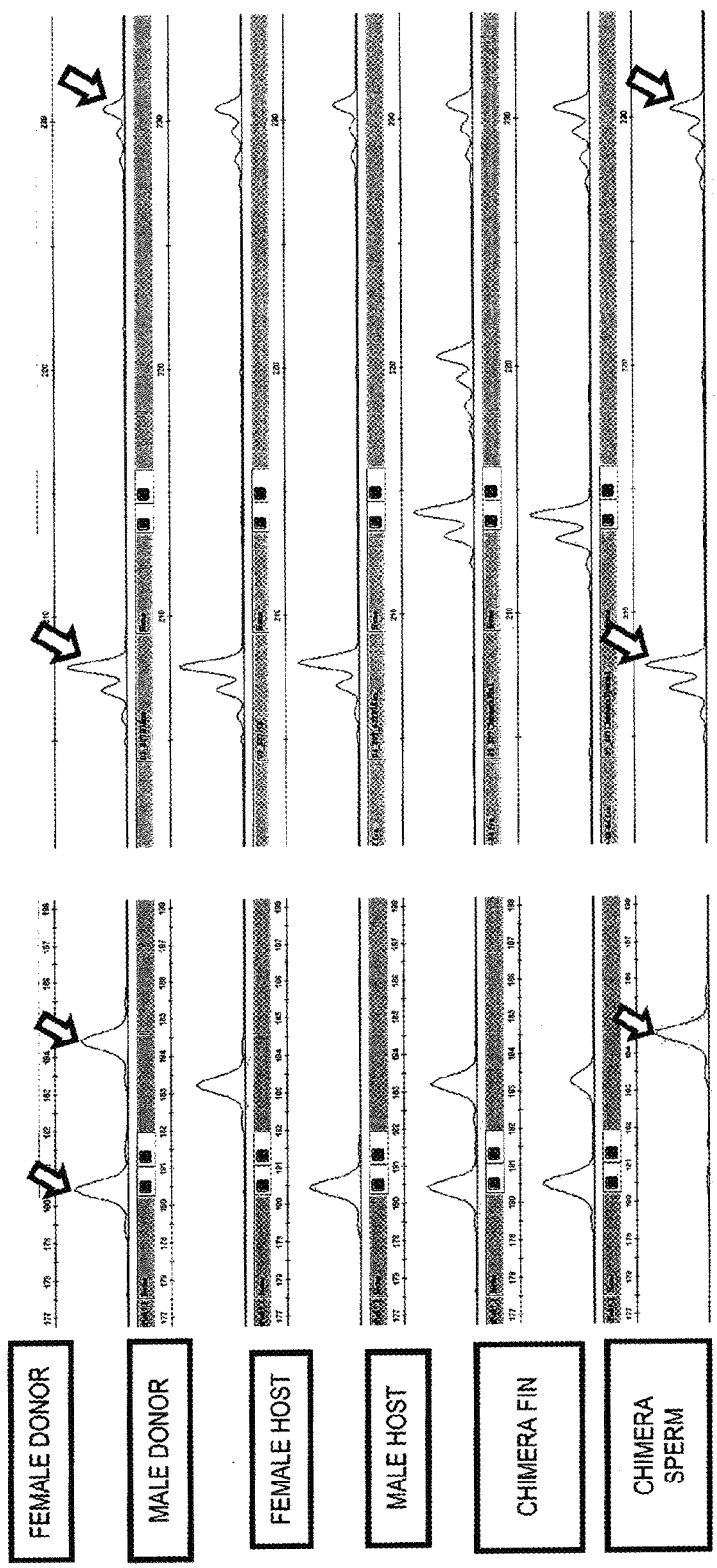
FIG. 25 is a conceptual diagram showing that the sperm derived from a germ line chimeric goldfish into which haploid PGC is transplanted is a clone. It was confirmed that heterogeneous markers (open arrows) appeared in a female donor and only one of them appeared in the gamete of the germ line chimera without exception. The left shows the appearance of only one marker thereof and the right shows the appearance of both markers. Only one of the markers should have appeared because it was a marker for a haploid from the mother.

3. Determination of Genetic Identity of Sperm of Chimera into which Goldfish Haploid PGC was Transplanted When a chimera forms sperms derived from haploid PGCs, the sperms derived from one litter need to have only one donor-derived allele in all microsatellite marker loci and be cloned sperms having no genetic variations between the sperms (FIG. 25). Accordingly, the marker type of the sperms produced by the chimera was examined using microsatellite markers for which a mother of the donor has heterozygous loci. As a result, it was shown that in sperms derived from the 2 individuals of 090307#4 and 090622, there was only an allele of one of donor parents (hemi-clonal-type) in all of the marker loci used (Table 17). For 090307#5, heterozygous loci was found in 3 out of 5 loci. This showed that the sperms of the 2 individuals of 090307#4 and 989622 were likely to be derived from haploid PGC and clonal.

TABLE 17

Result of Examining Whether Microsatellite Marker Observed in Heterozygous in Donor ♀ of Germ Line Chimera in Which Haploid PGC Was Transplanted in Goldfish Is Homozygous in Gamete of Germ Line Chimera

| | Marker for Which | Marker Type of Sperm Genome | |
|---|---|---|---|
| | Donor ♀ Was Hetero | Homo-Type | Hetero-Type |
| 20090307 #4 | 5 | 5 | 0 |
| 20090307 #5 | 5 | 2 | 3 |
| 20090622 | 6 | 6 | 0 |

The Case of Zebrafish *Danio rerio*

A. Material and Method

1. The zebrafish, *Danio rerio* was used as a material to produce a haploid-diploid germ line chimera (1n-2n) using a haploid as a donor and a normal diploid as a host by a developmental engineering method as described below. The 1n-2n was produced to examine whether haploid PGCs migrated to the genital ridge and proliferate as germ cells in a diploid host individual subjected to sterilization treatment by knock-down with the dead-end antisense morpholino oligonucleotide (for a zebrafish, SEQ ID NO: 9; 5'-GCTGGGCATCCATGTCTC-CGACCAT-3') and whether functional gametes were formed in their gonads. To determine whether the resultant offspring is derived from the donor PGC, by pigment in the offspring when in the future it is examined whether functional gametes are formed or not, a golden strain as a color mutant (recessive character) or recombinant individual was used as a donor.

2. Test Fish

In the present invention, the zebrafish *Danio rerio* and the goldfish *Carassius auratus* (male) reared in Field Science Center for Northern Biosphere, Hokkaido University were used as materials.

3. Collection of Egg and Sperm

Zebrafish were housed by separating the two sexes in a spawning water tank in a constant temperature room set at 16 L-8 D the day prior to egg collection. To obtain eggs for donors, female individuals were mixed with males immediately after switching lighting on at the egg collection day; a female individual identified for spawning was taken up; and the abdomen was pressed to collect eggs on Saran Wrap. For diploid embryos for hosts, female and male parent fishes were mixed immediately after switching lighting on at the egg collection day to induce spawning to provide fertilized eggs. Goldfish sperms were injected with hCG the day prior to sperm collection to induce spermiation. The goldfish sperms were collected in a hematocrit capillary tube, diluted in a goldfish artificial seminal fluid, and used in genetic inactivation.

4. Genetical Inactivation of Sperm

Ultraviolet irradiation was used for the genetical inactivation of eggs and sperms. A box-shaped apparatus in the upper part of which two ultraviolet germicidal lamps (GL15W, from National) were placed was used. The irradiation dose of ultraviolet rays for inactivating sperms was set to 60 mJ/cm$^2$. In gynogenesis, haploid sperms derived from a diploid goldfish were used. The reason is that the use of goldfish sperms can remove fertilized eggs obtained from sperms having escaped from the ultraviolet irradiation in gynogenesis of zebrafish because they become a hybrid susceptible to death.

5. Production of Haploid Donor and Diploid Host

After inseminating zebrafish eggs with ultraviolet-irradiated goldfish sperms, a gynogenetic haploid group of donor was produced by a method which involves scattering the resultant in a plastic petri dish filled with a fertilization solution at 28.5° C. for fertilization. The fertilization solution used was a tap water containing 0.2% urea and 0.24% NaCl. A diploid group was also produced as host by harvesting naturally spawned eggs. In an embryo used as a host, sterility was induced by inhibiting the differentiation of PGC by the microinjection of dndMO (SEQ ID NO: 9; 5'-GCTGGGCATCCATGTCTCCGACCAT-3') at the 1- to 4-cell stage after fertilization. The morphology of larval fishes from the haploid donor was observed and the occurrence rate of normal larval fishes and the number of appearance of larval fishes showing malformations such as a haploid syndrome were investigated. The stage of development was according to the report of Kimmel et al. (1995).

6. Removal of Egg Chorion and Culture of Dechorionated Egg

The haploid donor embryo and the diploid host embryo were treated with Ringer's solution for freshwater fishes (128 mM NaCl, 2.8 mM KCl, 1.9 mM CaCl$_2$, pH 7.0) containing 0.1% trypsin to remove the egg chorion. The dechorionated eggs were cultured to the somitogenesis stage in a glass petri dish whose bottom face was subjected to coating treatment with about 1% agarose, filled with a primary culture (Ringer's solution for freshwater fishes; 128 mM NaCl, 2.8 mM KCl, 1.9 mM CaCl$_2$, pH 7.0, containing 1.6% chicken egg white, 0.01% penicillin, and streptomycin) at 20° C. Thereafter, the dechorionated eggs were transferred to a secondary culture (a 1.8 mM CaCl$_2$, 1.8 mM MgCl$_2$ solution containing 0.01% penicillin and streptomycin) and cultured to hatching.

7. Measurement of Ploidy of Donor Embryo

To examine the success or failure of genetical inactivation of a sperm or an egg, the ploidy of the donor embryo used in producing the chimera was investigated using a flow cytometer (Partec Ploidy Analyser, Model PA). The donor embryo was placed in 150 µl of solution A (a nuclear isolation solution) for Cystain DNA 2 step kit (Partec) and allowed to stand for 20 minutes, and cells were mixed and dissociated by vortex. Thereafter, the specimen was filtered with a 50-µm mesh (Cell Trics 50 µm, Partec), to which solution B (a stain solution containing 4',6-diamidino-2-phenylindole (DAPI)) at a volume of 5 times that of the solution A was added after removing cell debris to measure the relative DNA content by flow cytometry. Here, the DNA content of the fin of the normal zebrafish was used as a standard for the diploid DNA content (2C), and the DNA content of the haploid sperm of the zebrafish was used as a standard for the haploid DNA content (1C).

8. Production of Germ Line Chimera in Zebrafish

To distinguish between the success and failure of a germ line chimera, the gynogenetic haploid donor used was a golden lineage and a recombinant lineage and the host used was a wild-type or golden lineage. The recombinant lineage used here is "GFP/RFP double transgenic strain" in which all cells are labeled with green fluorescence (GFP) and germ cells are labeled with red fluorescence (RFP). All host embryos were microinjected with 100 µM dnd MO between the 1-cell stage and the 4-cell stage for sterilization. When the golden was used as a donor, the microinjection of 300 ng/µl GFP-nos1 3'UTR mRNA was performed between the 1-cell stage and the 4-cell stage to visualize PGCs.

A. Result

Figure 26:
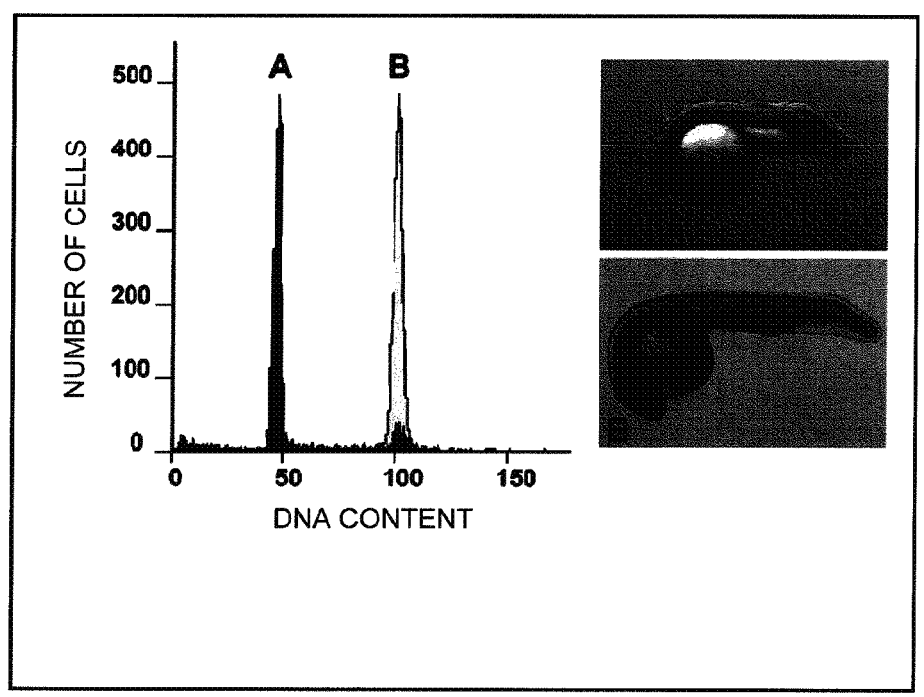
FIG. 26 is a drawing confirming the haploidy of a donor embryo used in a 1n-2n chimeric derivative of a zebrafish by FCM. A: the donor haploid, B: a diploid of a control group.

1. Blastomeres in the periphery of the blastoderm of a donor embryo at the blastula stage were aspirated with a fine glass needle and each transplanted into the blastoderm of a host embryo at the same developmental stage (BT chimera). Blastomeres from one individual could be transplanted to about 10 hosts. All of the embryos as used donors were cultured to the early somitogenesis stage and confirmed to be haploid using a flow cytometer (FIG. 26).

2. Dynamic State of Haploid PGC in Zebrafish BT Chimera 475 chimeric individuals were produced, and donor-derived PGCs were confirmed to be transplanted into 66 individuals thereof. In these individuals, the number of PGCs transplanted ranged from 5 to 14, but the donor PGCs were found to reach the gonad formation region in almost all of the embryos (Table 18). When a recombinant embryo was used as a donor, PGCs fluorescence in the chimera could be observed provided that cells were present. When the characteristic was used to identify the dynamic state of donor PGCs with time, the disappearance of the donor PGCs was identified at around 14 days of development in 5 of the 13 individuals observed. In these embryos, GFP fluorescence in the donor somatic cells simultaneously transplanted could be continuously observed; thus, the above disappearance is suggested to be PGCs-specific. In other individuals, the proliferation of the donor PGCs was identified. In these individuals, RFP fluorescence in PGCs was identified even at the stage of at least 30 days after fertilization.

TABLE 18

Normal Development Rate and Germ Line Chimera Induction Rate in Zebrafish 1n-2n Chimera Induced by BT Method

| Test Group | Total Number | Normal | PGCs Gonad Region | Ectopic |
|---|---|---|---|---|
| BT Chimera | 475 | 364 (76.6%) | 63 (17.3%) | 3 (0.8%) |
| Host Control | 78 | 58 (74.3%) | | |

3. Origin of Gamete in Zebrafish 1 n-2n BT Chimera

Figure 27:
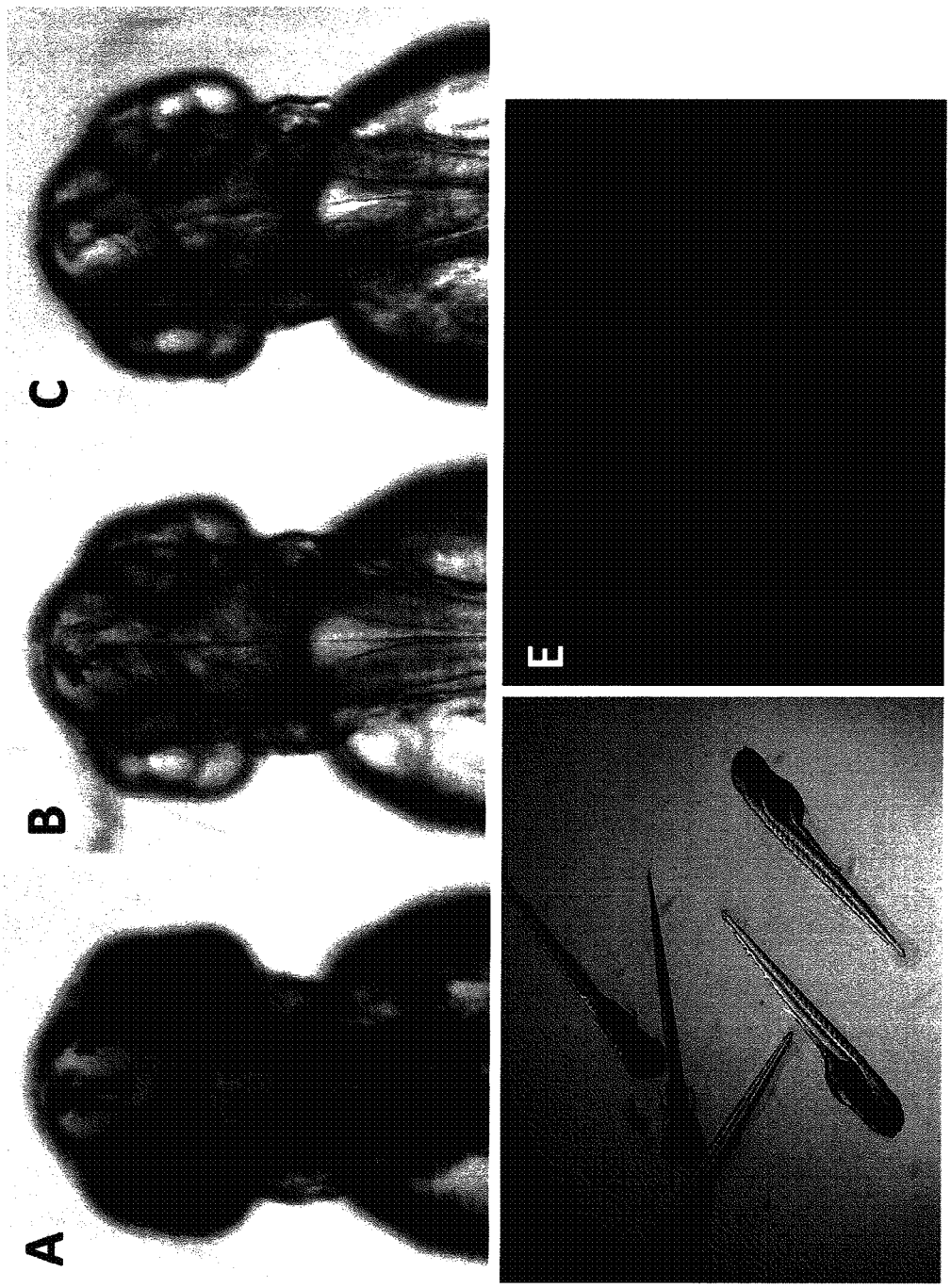
FIG. 27 is a series of photographs showing the phenotypes of the offspring obtained by the crossing with a diploid chimeric zebrafish individual into which golden lineage haploid PGCs and recombinant lineage haploid PGCs are transplanted. A: a wild-type lineage 3-day old larval fish, B: a golden lineage 3-day old larval fish, and C: a golden female× golden 1n-wild-type 2n male chimeric 3-day old larval fish. Note the concentration of chromatophore in the head. The chimera offspring took on the phenotype of the golden lineage which is a donor. D: the bright-field image of a golden female×recombinant 1n-golden 2n chimera offspring and E: the dark-field image. All offspring had GFP fluorescence derived from donor 1n PGCs.

Five of the golden lineage (1n)→wild-type lineage (2n) chimeric individuals produced matured and could be subjected to a crossing experiment. These 5 individuals were obtained by using a golden lineage as a donor for transplantation into sterilized wild-type lineage. All of these chimeras had male external morphology. When they were crossed with females of the golden lineage, several hundred or more fertilized eggs were obtained from one of the resultant individuals, and all offspring thereof had a golden lineage phenotype (FIG. 27). Similarly, 3 of recombinant lineage (1n)→golden lineage (2n) chimeric individuals matured. All of these chimeras also had a male external morphology. When they were subjected to a crossing experiment with non-recombinant female individuals, 8 fertilized eggs were found among 138 eggs obtained from 1 individual thereof. When these fertilized eggs were cultured, the expression of the GFP fluorescence derived from the recombinant lineage was observed. If host (wild-type) germ cells remain, which results in fertilization, the resultant offspring should have a host lineage phenotype. However, in a crossing experiment using a chimera confirmed to have fertility, only the offspring having a donor lineage phenotype were obtained. From these results, it was probable that the chimera gametes were derived from the transplanted haploid PGCs.

Statistical Analysis

In this application, statistical significance was evaluated by Student's t-test, Kruskal-Wallis test, and Scheffe method. P values less than 0.05 were determined significant.

Discussion

The chimeric fish obtained by the present invention can result in the development of a new breeding technology using haploid PGC in a fish.

According to the present invention, it was first attempted to make sure in a loach that only donor-derived gametes were formed in a germ line chimera obtained by transplanting 2n donor PGCs into a 3n host sterilized by dndMO treatment. As a result, the sperm produced by 2n-3n had normal morphology and seemed to have a function as a sperm because it had motility. The normal diploid testis was composed of a cell population of 2n and 4n in addition to in sperms and spermatids; however, the 2n-3n developed testis was composed of a cell population of in and 3n, 1n, 2n, and 3n, or in, 2n, 3n, and 4n, and among these cell populations, a peak for in cells was high and peaks for 2n and 4n cells were low. In fishes, it is generally considered that 2n represents A- and B-type spermatogonial cells and secondary spermatocytes, 4n represents primary spermatocytes, and in represents spermatids and sperms (Kobayashi, Adachi, et al., (2002) Seishoku (Reproduction), "Gyorui Seirigaku No Kiso" (Basis for Fish Physiology), Kouseisha-koseikaku, Tokyo, pp 155-182). In normal diploid and 2n-3n, the whole stage of sperm formation (spermatogonial cells, spermatocytes, many spermatids and sperms) was histologically observed; thus, it is probable that 2n cells in the testis detected by a flow cytometer are A- and B-type spermatogonial cells and secondary spermatocytes, 4n cells are primary spermatocytes, and in cells for which a high peak was detected are spermatids or sperms. From these results, it can be determined that functional sperms were produced from 2n donor-derived PGC in the 2n-3n chimera.

The formation of 1n sperms having normal morphology was observed in some of the germ line chimeric (1n-3n) individuals produced by transplanting haploid loach PGCs into a dndMO-treated sterilized 3n host. A cell population of 1n, 2n and 3n, or 1n, 2n-3n and 4n, or 1n, 2n-3n and 6n was observed in the 1n-3n developed testis, and the composition of these cell populations was different from that in the 2n-3n testis. In a 1n-3n individual, the heights of peaks for 1n and 2n were comparable and smaller than a peak for 4n, and the peak for 4n was highest. In another 1n-3n individual, a peak for a 1n cell population likely to be sperms was highest; however, a peak for a 2n cell population was also detected to hold second place thereto with regard to height. The 2n cell population is a cell population having ploidy originally not derived from a donor or a host. From these results, it is probable that 1n-3n, the transplanted donor 1n PGCs became 2n germ cells, which reproduced and then entered meiosis, followed by forming 1n spermatids or sperms in addition to 4n and 2n spermatocytes. At the same time, because a 3n cell population observed in the testis is derived from 3n somatic cells and 6n cells correspond to those during the G2 period thereof, both cells are presumably host-derived.

In many tissue images of the loach 1n-3n testis, many spermatogonial cells having different sizes and a few spermatocytes were observed. Accordingly, when the diameter of the nuclei of A-type spermatogonial cells was measured, many such cells were found to have nuclear sizes comparable to those of normal diploid and 2n-3n A-type spermatogonial cells. However, the measurement results in 1n-3n also showed the presence of cells having large nuclei. It is reported that in a naturally cloned loach suggested to be potentially of crossbreed origin, endomitosis by chromosomal doubling before meiosis produces the formation of diploid cloned gametes (Non Patent Literature 9). In the study, it is suggested that in a crossbred animal or an animal of crossbreed origin, when chromosomes cannot be paired at meiosis because of their low homology, the doubling of the chromosome occurs spontaneously through an unexplained mechanism and sister chromosomes behave as if they were homologous chromosomes to each other, thereby potentially producing pseudo-meiosis and the formation of unreduced gametes. The large 1n-3n nuclei observed in the study probably suggested that chromosomal doubling potentially occurred by a plurality of endomitoses during the period of A-type spermatogonial cells. Since many spermatogonial cells were observed in the tissue image thereof, it seems that 2n cells in the 1n-3n testis were diploid spermatogonial cells produced as the result of the occurrence of the spontaneous doubling of donor-derived haploid PGCs, or secondary spermatocytes after their entrance into meiosis. Cells having a ploidy of 4n probably had the possibility of being A-type spermatogonial cells whose ploidy increased to 4n, produced by a plurality of endomitoses of donor PGCs, or primary spermatocytes having started meiosis after becoming 2n, because large A-type spermatogonial cells could be observed. When 1n-3n A-type spermatogonial cells during the period of a larval fish (1- to 2-month old) were measured for the diameter of their nuclei, they were found to be cells having smaller nuclei than those of 2n-3n; thus, in cells seen in the 1n-3n testis may be 1n cells resulting from the proliferation of donor-derived in PGCs per se, or in spermatids or 1n sperms produced by the meiosis of haploid PGCs doubled during the period of spermatogonial cells. From these results, it was probable that in a germ line chimera, haploid-derived PGCs double to 2n during a certain period before proliferating as 2n spermatogonial cells by mitosis, start meiosis after reproduction and chromosomal pairing, and form haploid sperms.

Following the loach, a goldfish was used as a material to transplant haploid PGC into a sterilized host to examine whether gametes were produced. When goldfish haploid PGC was transplanted, the use of a method involving transplanting numeral PGCs provided many germ line chimeras having PGCs having migrated to the genital ridge compared to the use of a method involving transplanting one PGC, as a matter of course. The donor PGC having migrated to the genital ridge started proliferation after about one month. Since a plurality of donor PGCs simultaneously increased in one individual, the timing of the proliferation of PGC has the possibility of being controlled by the host. When hCG was injected to a germ line chimera having reached a mature size to induce ovulation or spermiation, sperms having motility were obtained from a plurality of individuals. When the origin of the resultant gametes were determined using microsatellite markers, 2 of the 4 individuals examined were decided to originate from donor-derived haploid PGCs. Another one individual was probably derived from a triploid host, and for the remaining one individual, there was probably the failure of gynogenesis or the coexistence of a donor-derived gamete.

In addition, a zebrafish was used as a material to transplant haploid PGCs into a sterilized diploid host to examine whether gametes were produced. The transplanted haploid PGCs moved through diploid host embryos and established around the genital ridge formation region. The disappearance of donor haploid PGCs was observed in some individuals, but the proliferation of PGCs was observed in the other individuals. When chimeric individuals in which donor haploid PGCs established in the gonad were bred and used for a crossing experiment, next-generation offspring having donor phenotypes were obtained from a chimera obtained by transplanting haploid golden lineage PGCs and a chimera obtained by transplanting haploid transgenic lineage PGCs. In these individuals, haploid PGCs were each doubled to a diploid during development and differentiation, followed by the production of a haploid gamete. In other words, it is probable that the gamete has only alleles possessed by the donor haploid (hemizygous) and are genetically identical thereas. This indicates that haploid PGCs can be doubled to produce normal gametes in a zebrafish as well as a goldfish and a loath.

As shown in this study, germ line chimeras obtained by transplanting haploid PGCs produce donor-derived sperms in the 3 fish species of a loath, a goldfish, and a zebrafish. This indicates that haploid PGC has the ability to differentiate to a sperm. As described in the example for a goldfish, all haploid PGC-derived sperms are predicted to be genetic clones. Meanwhile, the proportion of individuals in which PGCs proliferated was low and particularly the proportion of individuals completely lacking germ cells was high, in 1n-3n compared to in 2n-3n. The identification of the reason is difficult; however, it is possible that the expression of a recessive deleterious gene inhibiting reproduction occurred because the chromosome exists in only one set (Non Patent Literature 1). However, in the testis in 1 of the total 15 1n-3n male fish individuals, the same whole stage of sperm formation (spermatogonial cells, spermatocytes, spermatids, and sperms) as that in 2n and 2n-3n was observed. This suggested that haploid PGCs performed normal sperm formation via a germ line chimera. The 1n-3n developed ovary proved to be composed of 1n and 3n cells. As a result of measuring the diameter of the nuclei of oogonia, 1n-3n had small oogonia compared to those of normal 2n, 3n not treated with dndMO and 2n-3n; thus, it was probable that 1n cells in the ovary were cells resulting from the direct proliferation of donor haploid-derived PGCs. The composition of the 1n-3n ovary suggested that haploid PGCs had the possibility of proliferating by mitosis, and performing meiosis after the spontaneous doubling of the chromosome even in female 1n-3n since many oocytes at the perinucleolus stage and a few oocytes at the yolk vesicle stage were observed in the 1n-3n ovary as in the control 2n, 3n not treated with dndMO and 2n-3n ovary.

The base of breeding is to select excellent characters for crossing over repeated generations. However, the production of a lineage can be shortened by using a phenomenon in which haploid PGCs are doubled to produce homozygous gametes (clonal gametes: genetically completely identical gametes). For a zebrafish, about 10 chimeric individuals can be produced from one donor embryo individual in the production of a chimera by the BT method. According to this method, up to 4 of 10 chimeric individuals become a germ line chimera having a plurality of haploid PGCs. The use of the SPT method using PGCs having proliferated to about 50 at the somitogenesis stage can produce a chimera having more "PGCs derived from one donor embryo individual" in principle. If 2 of these chimeric individuals were developed to two sexes and crossed, the resultant offspring all become clones having the same genetic composition. In other words, a clonal lineage can be produced without performing crossing requiring long time. Putting this method to practical use probably greatly impacts the field of breeding as well as the field of basic biology.

Sequence Listing Free Text

SEQ ID NO: 1; Antisense Morpholino oligonucleotide
SEQ ID NO: 2; Forward Primer
SEQ ID NO: 3; Reverse Primer
SEQ ID NO: 4; Forward Primer
SEQ ID NO: 5; Reverse Primer
SEQ ID NO: 6; Antisense Morpholino oligonucleotide
SEQ ID NO: 7; Forward Primer
SEQ ID NO: 8; M13 Primer
SEQ ID NO: 9; Antisense Morpholino oligonucleotide

The invention claimed is:

1. A method for acquiring a chimeric male fish having a haploid germ cell, said male fish being selected from the group consisting of loach, goldfish and zebrafish, comprising the steps of:
   a) genetically inactivating a goldfish or zebrafish egg or a goldfish or zebrafish sperm, followed by insemination to provide a haploid donor fertilized egg;
   b) obtaining a fertilized egg of a host goldfish or zebrafish; and
   c) transplanting donor primordial germ cells obtained from a haploid donor embryo developed from the haploid donor fertilized egg into a host embryo derived from the host fertilized egg, thereby acquiring the chimeric male fish having the haploid germ cells.

2. The method according to claim 1, wherein the genetic inactivation of an egg or a sperm is performed by ultraviolet irradiation or radiation irradiation.

3. The method according to claim 1, wherein the host fish is a sterile host fish obtained by the fertilization of a normal polyploid egg by a diploid sperm of a tetraploid fish.

4. The method according to claim 1, wherein the donor is a color mutant or a genetic recombinant.

5. The method according to claim 1, wherein the host fish is a sterile host fish sterilized by knocking down a dead end gene in the host fertilized egg.

6. The method according to claim 5, wherein the knocking down is injecting a dead end antisense morpholino oligonucleotide into the host fertilized egg.

7. The method according to claim 1, wherein the transplantation is carried out by a blastomere transplantation method, a single primordial germ cell transplantation method, a poly primordial germ cell transplantation method, or a blastoderm transplantation method.

8. The method according to claim 1, wherein the donor or host fertilized egg is obtained, followed by removing the membrane of the egg.

9. Genetically identical gametes from the chimeric fish having a haploid germ cell obtained by the method according to claim 1.

10. The method according to claim 1, wherein the host fish is a sterile individual.

* * * * *

```
                              SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: antisense morpholino oligonucleotide

<400> SEQUENCE: 1
gatctgctcc ttccattgcg tttgc                                           25

<210> SEQ ID NO 2
<211> LENGTH: 20
<212> TYPE: DNA
<213> ORGANISM: Artificial Sequence
<220> FEATURE:
<223> OTHER INFORMATION: forward primer

<400> SEQUENCE: 2
ctgaacctgc catggatgac                                                 20

<210> SEQ ID NO 3
<211> LENGTH: 24
<212> TYPE: DNA
<213> ORGANISM: Artificial Sequence
<220> FEATURE:
<223> OTHER INFORMATION: reverse primer

<400> SEQUENCE: 3
cttcacctcc tttataaccc tcac                                            24

<210> SEQ ID NO 4
<211> LENGTH: 23
<212> TYPE: DNA
<213> ORGANISM: Artificial Sequence
<220> FEATURE:
<223> OTHER INFORMATION: forward primer

<400> SEQUENCE: 4
ttacccacac cgtgcccatc tac                                             23

<210> SEQ ID NO 5
<211> LENGTH: 21
<212> TYPE: DNA
<213> ORGANISM: Artificial Sequence
<220> FEATURE:
<223> OTHER INFORMATION: reverse primer

<400> SEQUENCE: 5
taccgcaaga ctccataccc a                                               21

<210> SEQ ID NO 6
<211> LENGTH: 25
<212> TYPE: DNA
<213> ORGANISM: Artificial Sequence
<220> FEATURE:
<223> OTHER INFORMATION: antisense morpholino oligonucleotide

<400> SEQUENCE: 6
```

```
                                         -continued
tccatgccgc tgtccacctg tgatg                                          25

<210> SEQ ID NO 7
<211> LENGTH: 15
<212> TYPE: DNA
<213> ORGANISM: Artificial Sequence
<220> FEATURE:
<223> OTHER INFORMATION: forward primer

<400> SEQUENCE: 7
agtcacgacg ttgta                                                     15

<210> SEQ ID NO 8
<211> LENGTH: 18
<212> TYPE: DNA
<213> ORGANISM: Artificial Sequence
<220> FEATURE:
<223> OTHER INFORMATION: M13 primer

<400> SEQUENCE: 8
gccagtcacg acgttgta                                                  18

<210> SEQ ID NO 9
<211> LENGTH: 25
<212> TYPE: DNA
<213> ORGANISM: Artificial Sequence
<220> FEATURE:
<223> OTHER INFORMATION: antisense morpholino oligonucleotide

<400> SEQUENCE: 9
gctgggcatc catgtctccg accat                                          25
```